US012612396B1

(12) United States Patent
Talbot et al.

(10) Patent No.: US 12,612,396 B1
(45) Date of Patent: Apr. 28, 2026

(54) MODULATORS OF BETA CATENIN AND USES THEREOF

(71) Applicant: Dewpoint Therapeutics, Inc., Boston, MA (US)

(72) Inventors: Adam Talbot, Boston, MA (US); Thomas Durand-Reville, Boston, MA (US)

(73) Assignee: Dewpoint Therapeutics, Inc., Boston, MA (US)

( * ) Notice: Subject to any disclaimer, the term of this patent is extended or adjusted under 35 U.S.C. 154(b) by 0 days.

(21) Appl. No.: 19/394,235

(22) Filed: Nov. 19, 2025

Related U.S. Application Data

(60) Provisional application No. 63/722,839, filed on Nov. 20, 2024.

(51) Int. Cl.
*C07D 417/14* (2006.01)
*A61K 31/4439* (2006.01)

(52) U.S. Cl.
CPC ........ *C07D 417/14* (2013.01); *A61K 31/4439* (2013.01)

(58) Field of Classification Search
None
See application file for complete search history.

(56) References Cited

U.S. PATENT DOCUMENTS

2009/0227624 A1 * 9/2009 Dasgupta ............. A61K 31/454 514/307

FOREIGN PATENT DOCUMENTS

| | | | | |
|---|---|---|---|---|
| CN | 116621794 | A | 8/2023 | |
| WO | 2008/139845 | A1 | 11/2008 | |
| WO | 2010/150927 | A1 | 12/2010 | |
| WO | 2014/159234 | A1 | 10/2014 | |
| WO | 2020/061150 | A1 | 3/2020 | |
| WO | WO-2021092240 | A1 * | 5/2021 | .............. A61P 17/06 |

OTHER PUBLICATIONS

Ma et al., The Development and Application of KinomePro-DL: A Deep Learning Based Online Small Molecule Kinome Selectivity Profiling Prediction Platform. J Chem Inf Model. Oct. 14, 2024;64(19): 7273-7290.

Peng et al., The synthesis and antileukemic activity of 5-substituted thiazolyl urea derivatives. Bioorg Med Chem Lett. Jan. 1, 2025;115:130018, 6 pages.

STN Registry No. 1910480-86-2, Carbamic acid, N-[4-methyl-5-[(4-methyl-1-piperidinyl)methyl]-2-thiazolyl]-, phenyl ester. 1 page, May 15, 2016.

STN Registry No. 2461127-68-2, Urea, N-(phenylmethyl)-N'-[5-(tetrahydro-2H-pyran-4-yl)-2-thiazolyl]-. 1 page, Aug. 26, 2020.

STN Registry No. 2680867-32-5, Carbamic acid, N-[5-[(3-bromophenyl)methyl]-4-methyl-2-thiazolyl]-, phenylmethyl ester, 1 page, Aug. 25, 2021.

STN Registry No. 3009708-21-5, 1,4-Oxazepine-4(5H)-carboxzmide, tetrahydro-3-methyl-N-[5-(tetrahydro-2H-pyran-4- yl)-2-thiazolyl]-. 1 page, Dec. 1, 2023.

STN Registry No. 3011176-97-6, Urea, N-[(5-methyl-3-isoxazoly)methyl]-N'-[5-(tetrahydro-2H-pyran-4-yl)-2-thiazolyl]-. 1 page, Dec. 5, 2023.

STN Registry No. 3011519-02-8, Urea, N-(2-pyridinylmethyl)-N'-[5-(tetrahydro-2H-pyran-4-yl)-2-thiazolyl]-. 1 page, Dec. 5, 2023.

STN Registry No. 3011519-07-3, Urea, N-(3,5-dimethyl-4-isoxazolyl)-N'-[5-(tetrahydro-2H-pyran-4-yl)-2-thiazolyl]-. 1 page, Dec. 5, 2023.

STN Registry No. 3011562-20-9, Urea, N-[(2-methyl-3-pyridinyl) methyl]-N'-[5-(tetrahydro-2H-pyran-4-yl)-2-thiazolyl]-. 1 page, Dec. 5, 2023.

STN Registry No. 3011565-68-4, 7-Azabicyclo[2.2.1]heptane-7-carboxamide, N-[5-(tetrahydro-2H-pyran-4-yl)-2-thiazolyl]-. 1 page, Dec. 5, 2023.

STN Registry No. 3011968-97-8, 1-Pyrrolidinecarboxamide, 3-ethyl-3-methyl-N-[5-(tetrahydro-2H-pyran-4-yl)-2- thiazolyl]-. 1 page, Dec. 6, 2023.

STN Registry No. 3012038-72-8, 1-Pyrrolidinecarboxamide, 2,3,4,-trimethyl-N-[5-(tetrahydro-2H-pyran-4-yl)-2- thiazolyl]-. 1 page, Dec. 6, 2023.

STN Registry No. 3012066-96-2, 1-Pyrrolidinecarboxamide, 2-(1-methyl-1H-pyrazol-4-yl)-N-[5-(tetrahydro-2H-pyran-4- yl)-2-thiazolyl]-. 1 page, Dec. 6, 2023.

STN Registry No. 3012085-59-2, 4-Morpholinecarboxamide, 2-methoxy-N-[5-(tetrahydro-2H-pyran-4-yl)-2-thiazolyl]-. 1 page, Dec. 6, 2023.

STN Registry No. 3019160-75-6, Pyrazolo[4,3-c]azepine-5(1H)-carboxamide, octahydro-1-methyl-N-[5-(tetrahydro-2H- pyran-4-yl)-2-thiazolyl]-. 1 page, Dec. 17, 2023.

(Continued)

*Primary Examiner* — Jeffrey S Lundgren
*Assistant Examiner* — Michael J Schmitt
(74) *Attorney, Agent, or Firm* — McCarter & English, LLP; Michael J. DeGrazia; James M. Alburger

(57) ABSTRACT

Provided are compounds of the Formula I:

(I)

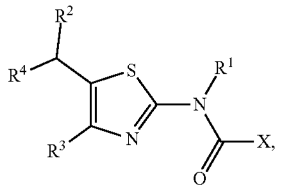

or pharmaceutically acceptable salts thereof, which are useful for the modulation of beta catenin condensates and in the treatment of a variety of conditions or diseases associated therewith.

4 Claims, 3 Drawing Sheets

(56) References Cited

OTHER PUBLICATIONS

STN Registry No. 3021221-18-8, Urea, N-(1-cyclobutyl-4-pyrazolidinyl)-N'-[5-(tetrahydro-2H-pyran-4-yl)-2-thiazolyl]-. 1 page, Dec. 20, 2023.
International Search Report and Written Opinion for Application No. PCT/US2025/056115, dated Feb. 12, 2026, 14 pages.

* cited by examiner

MODULATORS OF BETA CATENIN AND USES THEREOF

RELATED APPLICATIONS

This application claims priority to U.S. Provisional Application No. 63/722,839, filed on Nov. 20, 2024. The entire contents of the foregoing application are expressly incorporated herein by reference.

BACKGROUND

Biomolecular condensates are ubiquitous spatiotemporal organizers of biology, compartmentalizing and integrating a wide variety of regulatory pathways within cells. See Banani, S. F. et al. *Nat Rev Mol Cell Bio* 18, 285-298 (2017); and Hyman, A. A. et al. *Annu Rev Cell Dev Bi* 30, 39-58 (2014). Aberrant condensates, or condensatopathies, act as central nodes of dysfunction in disease, representing a new class of targets for drug discovery. See Alberti, S. et al. *Nat Rev Mol Cell Bio* 22, 196-213 (2021); Boija, A. et al. *Cancer Cell* 39, 174-192 (2021); Mitrea, D. M. et al. *Nat Rev Drug Discov* 1-22 (2022); Martin, E. W. et al. *J. Mol. Biol.* 168380 (2023); and Patel, A. et al. *Frontiers Mol Biosci* 9, 1007744 (2022). This new perspective expands the target space and enables new strategies for pursuing targets historically considered ‘undruggable’; these strategies include but are not limited to modifying the condensates these targets associate to, or targeting structural states that are selectively adopted by the ‘undruggable’ target inside the condensate. See Mitrea, D. et al. *Nat Rev Drug Discov* 1-22 (2022). Due to their integrative role, dysfunction of condensates leads to complex defects in multiple biological processes, explaining the root cause of complex diseases, such as cancer and neurodegeneration. This central role in pathophysiology also opens opportunities to discover broad-acting drugs that are active across large patient populations with a shared condensatopathy but of diverse genetic background.

Beta catenin is a validated anti-neoplastic target, known to be a driver of over-proliferation and aberrant transcriptional programming in a broad spectrum of cancers, including, but not limited to colorectal, breast, skin and pancreatic cancer. See Liu, J. et al. *Signal Transduct Target Ther*. (2022); and Zhang, Y. et al. *J Hematol Oncol* 13, 165 (2020). The cancer-driving activity of beta catenin is attributed to its constitutively active transcriptional promoting function, which results from several mutations and other aberrations along the dysregulated Wnt-pathway. Transcriptionally active beta catenin drives the expression of dozens of genes including NOTUM, MYC, AXIN2 and LEF1. See Nusse, R. et al. *Nature* 519, 163 (2015) and Herbst, A. et al. *BMC Genomics* 15, 74 (2014). Thus, what is needed is novel small molecules that modulate beta catenin’s aberrant transcriptional activation and cell proliferation through its sequestration into nuclear condensates.

SUMMARY

Provided herein are compounds having the Formula I:

(I)

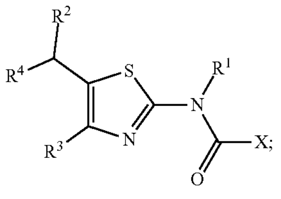

and pharmaceutically acceptable salts and compositions thereof, wherein $R^1$, $R^2$, $R^3$, $R^4$, and X are as described herein. In one aspect, the described compounds of Formula I and pharmaceutically acceptable salts thereof modulate beta catenin (e.g., sequester beta catenin in nuclear condensates), and are useful in a variety of therapeutic applications such as, for example, in treating cancer. See for example the cancer cell-line derived xenograft study and related data shown in the exemplification section below.

Pharmaceutical compositions comprising the described compounds and pharmaceutically acceptable salts of the described compounds, as well as methods for their preparation are also included.

DETAILED DESCRIPTION

1. General Description of Compounds

Figure 1:
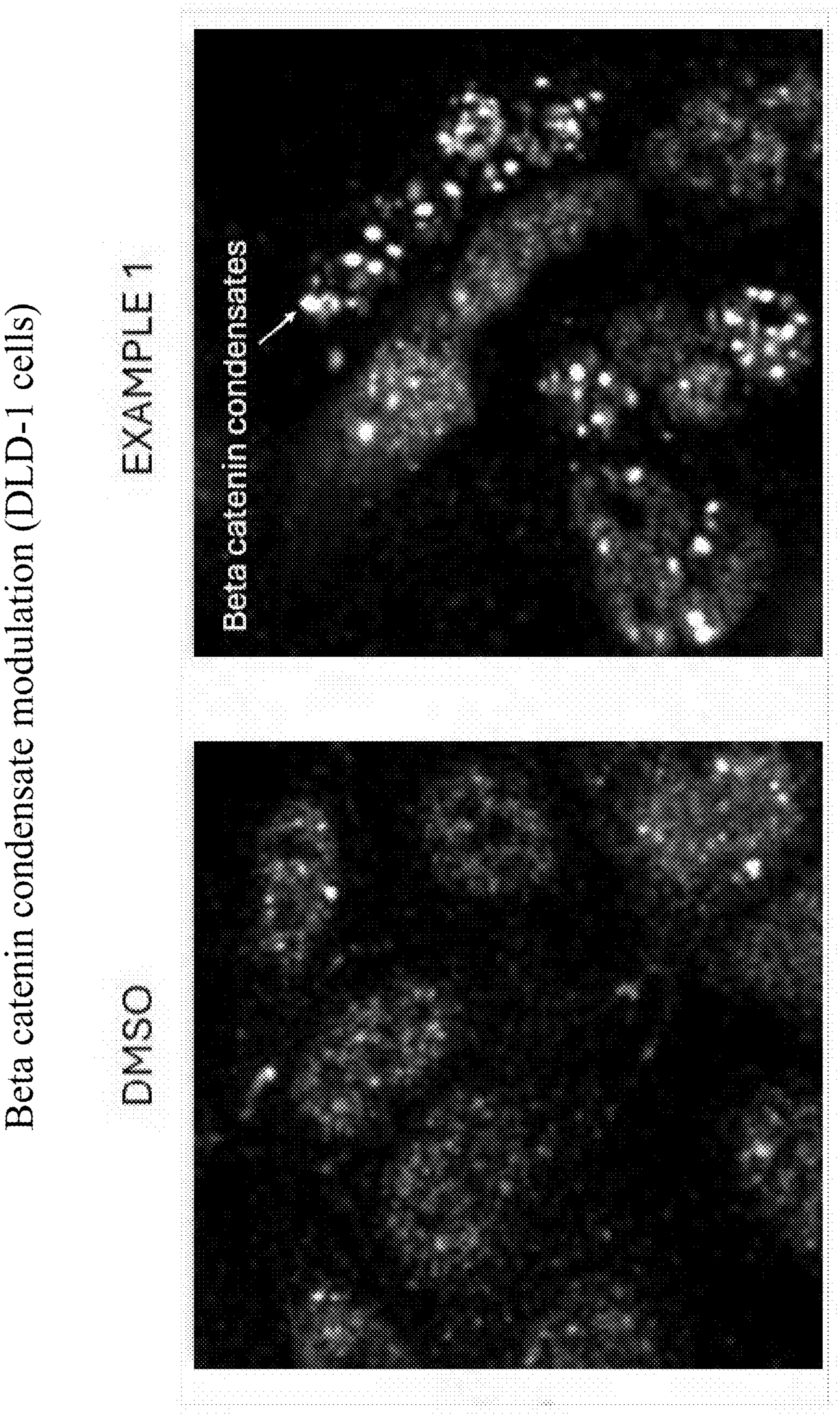
FIG. 1 shows the beta catenin condensate modulation in DLD-1 cells treated with Example 1 or DMSO.

In a first embodiment, provided herein are compounds having the Formula I:

(I)

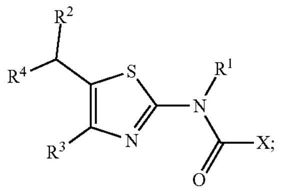

or a pharmaceutically acceptable salt thereof, wherein:

$R^1$ is hydrogen, $(C_1\text{-}C_4)$alkyl, or $(C_1\text{-}C_4)$alkylene[OP(O)$(OH)_2$];

$R^2$ is aryl, heteroaryl, heterocyclyl, or cycloalkyl, each of which are optionally substituted with 1 to 3 groups selected from $R^{1A}$;

$R^3$ is hydrogen, $(C_1\text{-}C_4)$alkyl, halo, or $(C_1\text{-}C_4)$alkylene$(C_1\text{-}C_4$alkoxy);

or $R^2$ and $R^3$ are taken together to form $C_5$cycloalkyl substituted with phenyl;

X is —$OR^6$ or —$NR^7R^8$;

$R^4$ is $(C_1\text{-}C_4)$alkyl, $(C_1\text{-}C_4)$alkyl, halo$(C_1\text{-}C_4)$alkyl, or heterocyclyl when X is —$NR^7R^8$, or $R^4$ is hydrogen, $(C_1\text{-}C_4)$alkyl, halo$(C_1\text{-}C_4)$alkyl, or heterocyclyl when X is —$OR^6$;

or $R^2$ and $R^4$ are taken together to form heterocyclyl;

$R^6$ is cycloalkyl, heterocyclyl, $(C_1\text{-}C_4)$alkylene$(C_1\text{-}C_4$alkoxy), $(C_1\text{-}C_4)$alkylene[aryl], $(C_1\text{-}C_4)$alkylene[heteroaryl], or $(C_1\text{-}C_4)$alkylene[cycloalkyl], wherein the aryl is substituted with 1 to 3 groups selected from $R^{2A}$ and the heteroaryl is optionally substituted with 1 to 3 groups selected from $R^{2A}$;

$R^7$ is H;

$R^8$ is cycloalkyl, heterocyclyl, $(C_1\text{-}C_4)$alkylene$(C_1\text{-}C_4$alkoxy), $(C_1\text{-}C_4)$alkylene[aryl], $(C_1\text{-}C_4)$alkylene

[heteroaryl], or ($C_1$-$C_4$)alkylene[cycloalkyl], wherein the cycloalkyl is optionally substituted with 1 to 3 groups selected from $R^{2A}$;

or $R^7$ and $R^8$ are taken together to form heterocyclyl or heteroaryl, each of which is optionally substituted with 1 to 3 groups selected from $R^{2A}$;

each $R^{1A}$ is independently selected from halo, cyano, ($C_1$-$C_4$)alkyl, hydroxy($C_1$-$C_4$)alkyl, hydroxy[halo($C_1$-$C_4$)alkyl], cyano($C_1$-$C_4$)alkyl, halo($C_1$-$C_4$)alkyl, ($C_1$-$C_4$)alkoxy, deuterated($C_1$-$C_4$)alkoxy, ($C_1$-$C_4$)alkoxyO($C_1$-$C_4$)alkyl, ($C_1$-$C_4$)alkoxyO[deuterated($C_1$-$C_4$)alkyl], halo($C_1$-$C_4$)alkoxy, ($C_1$-$C_4$)alkoxyO[halo($C_1$-$C_4$)alkyl], oxo, hydroxy, —O[hydroxy($C_1$-$C_4$)alkyl], —O[cycloalkyl], —O[heterocyclyl], —O[aryl], —O[heteroaryl], ($C_1$-$C_4$)alkylene[cycloalkyl], ($C_1$-$C_4$)alkylene[aryl], ($C_1$-$C_4$)alkylene[heterocyclyl], ($C_1$-$C_4$)alkylene[heteroaryl], —O($C_1$-$C_4$)alkylene[$NR^aR^b$], —O($C_1$-$C_4$)alkylene[$NR^aC(O)R^b$], —O($C_1$-$C_4$)alkylene[cycloalkyl], —O($C_1$-$C_4$)alkylene[aryl], —O($C_1$-$C_4$)alkylene[heterocyclyl], —O($C_1$-$C_4$)alkylene[heteroaryl], cycloalkyl, heterocyclyl, aryl, heteroaryl, ($C_1$-$C_4$)alkylene($C_1$-$C_4$)alkoxy, ($C_1$-$C_4$)alkylene[deuterated($C_1$-$C_4$)alkoxy], ($C_1$-$C_4$)alkylene[halo($C_1$-$C_4$)alkoxy], ($C_1$-$C_4$)alkoxyO[cycloalkyl], ($C_1$-$C_4$)alkoxyO[heterocyclyl], ($C_1$-$C_4$)alkoxyO[heteroaryl], ($C_1$-$C_4$)alkoxyO[phenyl], —C(O)[heterocyclyl], —$SR^a$, —$S(O)R^a$, —$SO_2R^a$, —$S(O)(NR^a)R^b$, —$NR^bSO_2R^b$, —$SO_2NR^a$, —$C(O)R^a$, —$C(O)OR^a$, —$C(O)NR^aR^b$, —$NR^aC(O)R^b$, —$NR^aC(O)NR^b$, —$NR^aR^b$, —NH($C_1$-$C_4$)alkylene[heterocyclyl], and ($C_1$-$C_4$)alkylene$NR^aR^b$, where each occurrence of cycloalkyl, heterocyclyl, aryl, and heteroaryl alone, or as part of another group, is optionally substituted with 1 to 3 groups selected from halo, oxo, ($C_1$-$C_4$)alkyl, halo($C_1$-$C_4$)alkyl, hydroxy($C_1$-$C_4$)alkyl, ($C_1$-$C_4$)alkoxy, halo($C_1$-$C_4$)alkoxy, hydroxy, —$NH_2$, —NH($C_1$-$C_4$)alkyl, —N(($C_1$-$C_4$)alkyl)$_2$, cycloalkyl, heterocyclyl, aryl, heteroaryl, and CN;

each $R^{2A}$ is independently selected from halo, ($C_1$-$C_4$)alkyl, halo($C_1$-$C_4$)alkyl, hydroxy($C_1$-$C_4$)alkyl, deuterated($C_1$-$C_4$)alkyl, ($C_1$-$C_4$)alkoxy, halo($C_1$-$C_4$)alkoxy, deuterated($C_1$-$C_4$)alkoxy, ($C_1$-$C_4$)alkylene($C_1$-$C_4$)alkoxy, ($C_1$-$C_4$)alkylene[deuterated($C_1$-$C_4$)alkoxy], ($C_1$-$C_4$)alkylene[halo($C_1$-$C_4$)alkoxy], oxo, —O[cycloalkyl], CN, hydroxy, S(O)($C_1$-$C_4$)alkyl, —S(O)$_2$($C_1$-$C_4$)alkyl, hydroxy, cycloalkyl, heterocyclyl, aryl, heteroaryl, ($C_1$-$C_4$)alkylene[cycloalkyl], ($C_1$-$C_4$)alkylene[aryl], ($C_1$-$C_4$)alkylene[heterocyclyl], ($C_1$-$C_4$)alkylene[heteroaryl], —$C(O)R^{a1}$, —$C(O)OR^{a1}$, —$C(O)NR^aR^b$, —$NR^{a1}C(O)R^{b1}$, —$NR^{a1}C(O)NR^{b1}$, wherein said heterocyclyl, aryl, heteroaryl, and cycloalkyl are each optionally substituted with 1 to 3 groups selected from halo, ($C_1$-$C_4$)alkyl, halo($C_1$-$C_4$)alkyl, ($C_1$-$C_4$)alkoxy, halo($C_1$-$C_4$)alkoxy, and CN;

each $R^a$, $R^{a1}$, $R^b$, and $R^{b1}$ is each independently selected from hydrogen, ($C_1$-$C_4$)alkyl, halo($C_1$-$C_4$)alkyl, ($C_1$-$C_4$)alkylene($C_1$-$C_4$)alkoxy, ($C_1$-$C_4$)alkylene$NH_2$, ($C_1$-$C_4$)alkyleneNH(($C_1$-$C_4$alkyl), ($C_1$-$C_4$)alkyleneN(($C_1$-$C_4$alkyl)$_2$, cycloalkyl, and heterocyclyl, wherein the cycloalkyl and heterocyclyl are each optionally substituted with ($C_1$-$C_4$)alkyl, hydroxy, or hydroxy($C_1$-$C_4$)alkyl.

2. Definitions

Unless otherwise defined, all technical and scientific terms used herein have the same meaning as commonly understood by one of ordinary skill in the art to which this disclosure pertains. The terminology used in the description is for describing particular embodiments only and is not intended to be limiting of the disclosure.

As used in the structure herein a hyphen (-) or squiggly line "~~~" indicates the point of attachment of the particular depicted structure or substituent group to the appropriate atom(s) in the remainder of the molecule.

The articles "a" and "an" as used herein and in the appended claims are used herein to refer to one or to more than one (e.g., to at least one) of the grammatical object of the article unless the context clearly indicates otherwise. By way of example, "an element" means one element or more than one element.

The term "alkyl," when used alone or as part of a substituent group, refers to a straight- or branched-chain hydrocarbon group having from 1 to 12 carbon atoms ("$C_1$-$C_{12}$"), for example 1 to 6 carbons atoms ("$C_1$-$C_6$"), or 1 to 4 carbons atoms ("$C_1$-$C_4$") in the group. Examples of alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentyl, amyl, neopentyl, 3-methyl-2-butanyl, tertiary amyl), hexyl ($C_6$) (e.g., n-hexyl), heptyl ($C_7$) (e.g., n-heptyl), octyl ($C_8$) (e.g., n-octyl), and the like. In some embodiments, the alkyl group is a $C_1$-$C_6$alkyl; in other embodiments, it is a $C_1$-$C_4$alkyl; and in other embodiments, it is a $C_1$-$C_3$alkyl.

As used herein, the term "alkenyl" refers to a straight- or branched-chain group having from 2 to 12 carbon atoms ("$C_2$-$C_{12}$") in the group, wherein the group includes at least one carbon-carbon double bond. Examples of alkenyl groups include vinyl (—CH=CH$_2$; $C_2$alkenyl), allyl (—CH$_2$—CH=CH$_2$; $C_3$alkenyl), propenyl (—CH=CHCH$_3$; $C_3$alkenyl), isopropenyl (—C(CH$_3$)=CH$_2$; $C_3$alkenyl), butenyl (—CH=CHCH$_2$CH$_3$; $C_4$alkenyl), sec-butenyl (—C(CH$_3$)=CHCH$_3$; $C_4$alkenyl), iso-butenyl (—CH=C(CH$_3$)$_2$; $C_4$alkenyl), 2-butenyl (—CH$_2$CH=CHCH$_3$; $C_4$alkyl), pentenyl (—CH=CHCH$_2$CH$_2$CH$_3$; $C_5$alkenyl), and the like.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

The term "cycloalkyl" when used alone or as part of a substituent group refers to cyclic-containing, saturated or partially unsaturated hydrocarbon groups having from 3 to 10 carbon atoms ("$C_3$-$C_{10}$"), for example from 3 to 7 carbon atoms ("$C_3$-$C_7$"). Examples of cycloalkyl groups include cyclopropyl ($C_3$), cyclobutyl ($C_4$), cyclopentyl ($C_5$), cyclohexyl ($C_6$), cycloheptyl ($C_7$), and the like. In some embodiments, the cycloalkyl group is a $C_{3-4}$cycloalkyl; in other embodiments, it is a $C_3$-$C_6$cycloalkyl; and in other embodiments, it is $C_3$-$C_8$cycloalkyl.

The term "alkylene" refers to a straight- or branched-chain group having from 2 to 12 carbon atoms ("$C_2$-$C_{12}$") in the group which is further substituted by a separate group. Examples of alkylene include ($C_1$-$C_4$)alkylene[heterocyclyl], which is a $C_1$-$C_4$alkyl substituted with a heterocyclyl, ($C_1$-$C_4$)alkylene[aryl], which is a $C_1$-$C_4$alkyl substituted with an aryl, ($C_1$-$C_4$)alkylene[cycloalkyl], which is a $C_1$-$C_4$alkyl substituted with a cycloalkyl, and ($C_1$-$C_4$)alkylene[heteroaryl], which is a $C_1$-$C_4$alkyl substituted with a heteroaryl.

The term "halo" or "halogen," as used by itself or as part of another group refers to a fluorine, chlorine, bromine, or iodine atom.

As used herein, the term "haloalkyl" and "haloalkenyl" refer to an alkyl or alkenyl group, respectively, wherein one or more of the hydrogen atoms has been replaced with one or more halogen atoms which may be the same or different.

The term "alkoxy" as used by itself or as part of another group refers to an oxygen radical attached to an alkyl group by a single bond. Examples of alkoxyl groups include methoxy ($OCH_3$), ethoxy ($OCH_2CH_3$), propoxy (e.g., —$O^n$Pr, —$O^i$Pr), or butoxy (e.g., —$O^n$Bu, —$O^i$Bu, —$O^s$Bu, —$O^t$Bu), and the like. In other embodiments, the alkoxy group is a $C_{1-6}$alkoxy. In further embodiments, the alkoxy group is a $C_{1-4}$alkoxy. In further embodiments, the alkoxy group is a $C_{1-3}$alkoxy.

As used herein, the term "haloalkoxy" refers to an alkoxy group wherein one or more of the hydrogen atoms has been replaced with one or more halogen atoms which may be the same or different.

A "deuterated" alkyl or alkoxy group means that one or more hydrogen atoms is replaced with deuterium. The deuterium enrichment at any one of the sites where hydrogen has been replaced by deuterium is at least 50%, 75%, 85%, 90%, 95%, 98% or 99%. Deuterium enrichment is a mole percent and is obtained by dividing the number of deuterium atoms at all sites of enrichment with the number of hydrogen plus deuterium atoms at all of the sites of enrichment. For example, a compound with two deuterated methyl groups has a 98.0% enrichment when 98.0% of the hydrogen atoms on the two methyl groups have been replaced with deuterium.

The term "aryl" used alone or as part of a larger moiety refers to, unless otherwise specified, a 6- or 10-membered aromatic hydrocarbon ring. An aryl group may be mono- or bi-cyclic, e.g., phenyl or naphthyl.

The term "heteroaryl" used alone or as part of a larger moiety refers to, unless otherwise specified, a 5- to 12-membered aromatic radical containing 1-4 heteroatoms selected from N, O, and S. A heteroaryl group may be mono- or bi-cyclic. Monocyclic heteroaryl includes, for example, thienyl, furanyl, pyrrolyl, imidazolyl, pyrazolyl, triazolyl, tetrazolyl, oxazolyl, isoxazolyl, triazinyl, tetrazinyl, oxadiazolyl, thiazolyl, isothiazolyl, thiadiazolyl, pyridyl, pyridazinyl, pyrimidinyl, pyrazinyl, etc. Bi-cyclic heteroaryls include groups in which a monocyclic heteroaryl ring is fused to one or more aryl or heteroaryl rings. Nonlimiting examples include indolyl, imidazopyridinyl, benzooxazolyl, benzooxodiazolyl, indazolyl, benzimidazolyl, benzthiazolyl, quinolyl, quinazolinyl, quinoxalinyl, pyrrolopyridinyl, pyrrolopyrimidinyl, pyrazolopyridinyl, thienopyridinyl, thienopyrimidinyl, indolizinyl, purinyl, naphthyridinyl, and pteridinyl. It will be understood that when specified, optional substituents on a heteroaryl group may be present on any substitutable position.

The term "heterocyclyl" means, unless otherwise specified, a 5- to 12-membered saturated or partially unsaturated heterocyclic ring containing 1 to 4 heteroatoms independently selected from N, O, and S. It can be monocyclic, bicyclic (e.g., a bridged, fused, or spiro bicyclic ring), or tricyclic. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. A heterocyclyl group may be mono- or bicyclic. The term "heterocyclyl" also includes, e.g., unsaturated heterocyclic radicals fused to another unsaturated heterocyclic radical or aryl or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position.

The term "spiro" refers to two rings that shares one ring atom (e.g., carbon).

The term "fused" refers to two rings that share two adjacent ring atoms with one another.

The term "bridged" refers to two rings that share three ring atoms with one another.

The term "optionally substituted," as used herein to describe a chemical moiety defined herein, means that the moiety may, but is not required to be, substituted with one or more suitable functional groups or other substituents as provided herein.

As used herein, the term "oxo" refers to a "=O" functional group.

As used herein, the term "substituted" means that an atom or group of atoms has replaced hydrogen as the substituent attached to another group.

The term "about" when used in combination with a numeric value or range of values means the value or range of values may deviate to an extent deemed reasonable to one of ordinary skill in the art.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including supercritical fluid chromatography (SFC), chiral high-pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, IN 1972).

Exemplary compounds of the disclosure including a chiral center may be depicted herein as having particular stereochemistries, but for which absolute stereochemistry has not been obtained. Absolute configurations can be obtained using methods known in the art.

As used herein, the term "stereoisomers" refers to compounds which have identical chemical constitution and connectivity but differ with regard to the arrangement of the atoms or groups in space, e.g., enantiomers or diastereomers.

As discussed in more detail below, the enantiomers of certain compounds were resolved. Unless otherwise noted, the enantiomer which showed a greater potency in the DLD-1 cell viability and immunofluorescence assays was arbitrarily assigned the "R" stereochemistry, and the less potent enantiomer was arbitrarily assigned the "S" stereochemistry. The absolute configuration of the enantiomers can be verified by means known to those in the art such as by NMR and/or X-ray crystallography. Nonetheless, when the stereochemical configuration at a chiral center in a compound having one or more chiral centers is depicted by its chemical name (e.g., where the configuration is indicated in the chemical name by "R" or "S") or structure (e.g., the configuration is indicated by dashed or wedge bonds), the enrichment of the indicated configuration relative to the opposite configuration is greater than 50%, 60%, 70%, 80%, 90%, 99% or 99.9%, preferably greater than 90%. "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When a disclosed compound is named or depicted by structure without indicating stereochemistry, it is understood that the name or the structure encompasses one of the possible stereoisomers or geometric isomers free of the others, or a mixture of the encompassed stereoisomers or geometric isomers.

It will be understood that certain compounds disclosed herein may exist in tautomeric forms. Such forms are included as part of the present disclosure. Thus, when a compound herein is represented by a structural formula or designated by a chemical name herein, all tautomeric forms which may exist for the compound are encompassed by the structural formula.

When the compounds described herein contain olefinic double bonds or other centers of geometric asymmetry, and unless specified otherwise, it is intended that they include both E and Z geometric isomers.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

As used herein, the terms "treatment," "treat," and "treating" refer to reversing, alleviating, delaying the onset of, or inhibiting the progress of a disease or disorder, or one or more symptoms thereof, as described herein. In some aspects, treatment may be administered after one or more symptoms have developed, i.e., therapeutic treatment. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

In some embodiments, the pharmaceutically acceptable salt of a compound described herein is a mono or di-sodium salt e.g., when $R^1$ is $(C_1\text{-}C_4)$alkylene$[OP(O)(OH)_2]$.

"Pharmaceutically acceptable" means approved or approvable by a regulatory agency of the Federal or a state government or the corresponding agency in a country other than the United States, or that is listed in the U.S. Pharmacopoeia or other generally recognized pharmacopoeia for use in animals, e.g., in humans.

The term "effective amount" or "therapeutically effective amount" refers to an amount of a compound described herein that is sufficient to achieve the desired therapeutic effect (such as treatment of a condition recited herein) under the conditions of administration.

The use of any and all examples, or exemplary language (e.g., "such as" and "e.g.") provided herein, is intended to better illustrate the disclosure and is not a limitation on the scope of the disclosure unless otherwise claimed. Phrases such as "in one aspect", "in one embodiment", "in another aspect", "in another embodiment", "in embodiments", and the like should not be construed as indicating that such elements occur or exist in isolation or that such elements are not shared by other aspects or embodiments of the disclosure. Rather, it should be understood that all aspects and embodiments may be freely combined with any and all other aspects and embodiments of the disclosure as described herein. No language in the specification should be construed as indicating that any non-claimed element is essential to the practice of the disclosure.

3. Compounds

As part of a second embodiment, for the compounds of Formula I, or a pharmaceutically acceptable salt thereof, $R^1$ is hydrogen or $(C_1\text{-}C_4)$alkylene$[OP(O)(OH)_2]$, and wherein the remaining variables are as described above for Formula I. Alternatively, as part of the second embodiment, for the compounds of Formula I, or a pharmaceutically acceptable salt thereof, $R^1$ is hydrogen, and wherein the remaining variables are as described above for Formula I.

As part of a third embodiment, for the compounds of Formula I, or a pharmaceutically acceptable salt thereof, $R^3$ is hydrogen, $—CH_3$, or $—CH_2OCH_3$, and wherein the remaining variables are as described above for Formula I or the second embodiment. Alternatively, as part of the third embodiment, for the compounds of Formula I, or a pharmaceutically acceptable salt thereof, $R^3$ is hydrogen, and wherein the remaining variables are as described above for Formula I or the second embodiment.

As part of a fourth embodiment, for the compounds of Formula I, or a pharmaceutically acceptable salt thereof, $R^4$ is $—CH_3$, $—CF_3$, $—CH_2F$, $—CHF_2$, $—OCH_3$, or

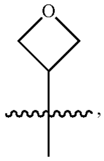 [SMILES: *C1COC1], and wherein the remaining variables are as described above for Formula I or the second or third embodiment. Alternatively, as part of the fourth embodiment, for the compounds of Formula I, or a pharmaceutically acceptable salt thereof, $R^4$ is $—CH_3$

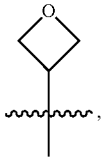 [SMILES: *C1COC1], and wherein the remaining variables are as described above for Formula I or the second or third embodiment.

As part of a fifth embodiment, for the compounds of Formula I, or a pharmaceutically acceptable salt thereof, X is O and $R^4$ is hydrogen, and wherein the remaining variables are as described above for Formula I or the second or third embodiment.

As part of a sixth embodiment, for the compounds of Formula I, or a pharmaceutically acceptable salt thereof, $R^2$ is aryl, heteroaryl, or heterocyclyl, each of which are optionally substituted with 1 to 3 groups selected from $R^{1A}$, and wherein the remaining variables are as described above for Formula I or any one of the second to fifth embodiments. Alternatively, as part of the sixth embodiment, for the compounds of Formula I, or a pharmaceutically acceptable salt thereof, $R^2$ is phenyl, pyridinyl, pyrimidyl, pyrazinyl, benzimidazolyl, pyrazolyl, or dihydrobenzooxazolyl, each of which is optionally substituted with 1 to 3 groups selected from $R^{1A}$, and wherein the remaining variables are as described above for Formula I or any one of the second to fifth embodiments. Alternatively, as part of the sixth embodiment, for the compounds of Formula I, or a pharmaceutically acceptable salt thereof, $R^2$ is:

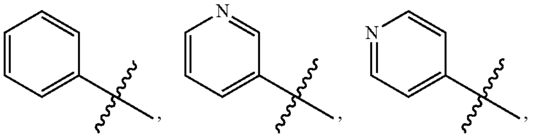

-continued

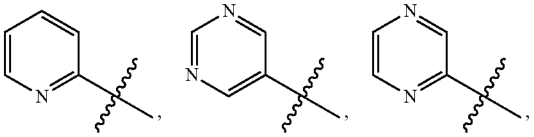

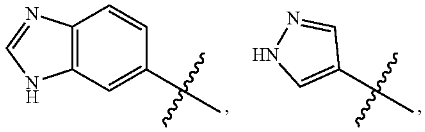 or

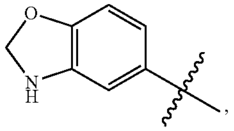

each of which is optionally substituted with 1 to 3 groups selected from $R^{1A}$, and wherein the remaining variables are as described above for Formula I or any one of the second to fifth embodiments. Alternatively, as part of the sixth embodiment, for the compounds of Formula I, or a pharmaceutically acceptable salt thereof, $R^2$ is:

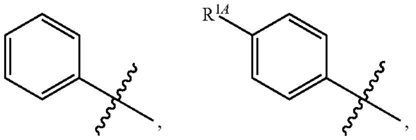

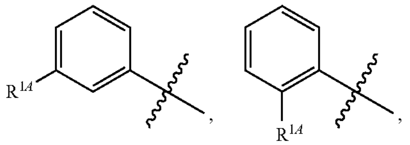

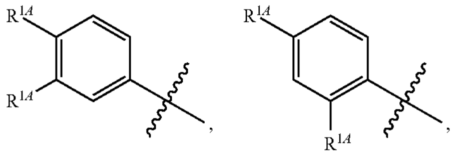

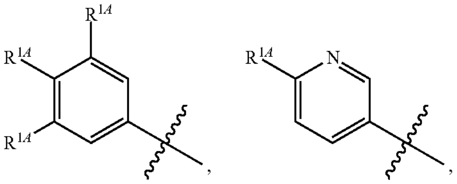

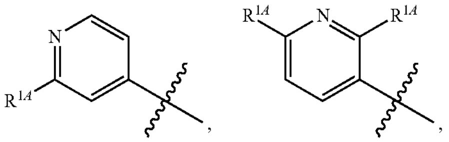

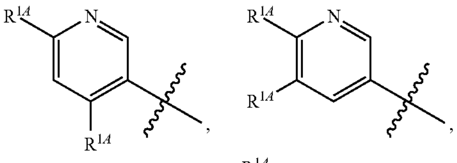

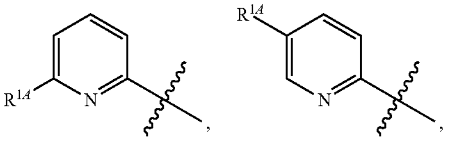

-continued

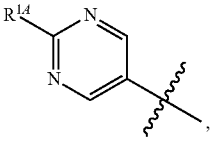, 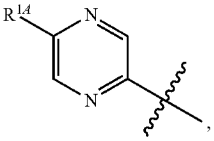,

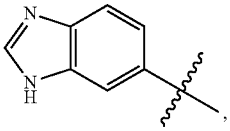, 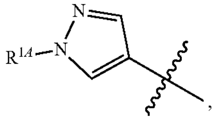, or

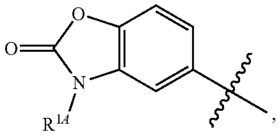, and wherein the remaining variables are as described above for Formula I or any one of the second to fifth embodiments.

As part of a seventh embodiment, for the compounds of Formula I, or a pharmaceutically acceptable salt thereof, each $R^{1A}$ is independently halo, $(C_1\text{-}C_4)$alkyl, halo$(C_1\text{-}C_4)$alkyl, hydroxy$(C_1\text{-}C_4)$alkyl, $(C_1\text{-}C_4)$alkyleneN$R^aR^b$, cyano, hydroxy, $(C_1\text{-}C_4)$alkoxy, deuterated$(C_1\text{-}C_4)$alkoxy, halo$(C_1\text{-}C_4)$alkoxy, —O[hydroxy$(C_1\text{-}C_4)$alkyl], $(C_1\text{-}C_4)$alkoxyO$(C_1\text{-}C_4)$alkyl, —O$(C_1\text{-}C_4)$alkylene[N$R^aR^b$], —O$(C_1\text{-}C_4)$alkylene[N$R^a$C(O)$R^b$], —O[cycloalkyl], —O[heterocyclyl], —O$(C_1\text{-}C_4)$alkylene[heterocyclyl], —N$R^aR^b$, —N$R^a$C(O)$R^b$, —S$R^a$, —S(O)(N$R^a$)$R^b$, —C(O)N$R^aR^b$, or heterocyclyl, wherein the heterocyclyl is optionally substituted with hydroxy or hydroxy$(C_1\text{-}C_4)$alkyl, and wherein the remaining variables are as described above for Formula I or any one of the second to sixth embodiments.

As part of an eighth embodiment, for the compounds of Formula I, or a pharmaceutically acceptable salt thereof, $R^a$ and $R^b$ are each independently hydrogen, $(C_1\text{-}C_4)$alkyl, $(C_1\text{-}C_4)$alkylene$(C_1\text{-}C_4)$alkoxy, $(C_1\text{-}C_4)$alkylene$NH_2$, or heterocyclyl, and wherein the remaining variables are as described above for Formula I or any one of the second to seventh embodiments.

As part of a ninth embodiment, for the compounds of Formula I, or a pharmaceutically acceptable salt thereof, each $R^{1A}$ is independently —F, —Cl, —$CH_3$, —$CF_3$, —$CH_2OH$, —$CH_2CH_2CH_2NH_2$, CN, hydroxy, —$OCH_3$, —$OCD_3$, —$OCHF_2$, —$OCF_3$, —$OCH_2CH_3$, —$OCH(CH_3)_2$, —$OCH_2CH_2OH$, —$OCH_2CH_2OCH_3$, —$OCH_2CH_2NH_2$, —$OCH_2CH_2N(CH_3)_2$, —$OCH_2CH_2CH_2NH_2$, —$OCH_2CH_2CH_2NHC(O)CH_3$, —$OCH_2CH_2CH_2CH_2NH_2$, —$OCH_2CH_2CH_2CH_2N(CH_3)_2$, —$NH_2$, —$N(CH_3)$, —$N(CH_3)CH_2CH_2OCH_3$, —$NHCH_2CH_2OCH_3$, —$NHCH_2CH_2CH_2NH_2$, —$NHCH_2CH_2CH_2CH_2NH_2$, —$NHC(O)CH_3$, —$SCH_2CH_2CH_2NH_2$, —$S(O)(NH)CH_2CH_2CH_2NH_2$,

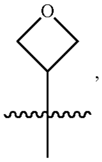, 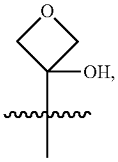, 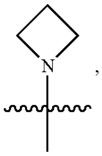, 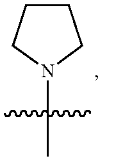,

-continued

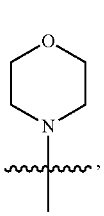, 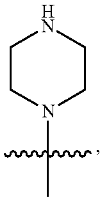, 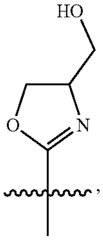, 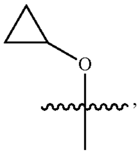,

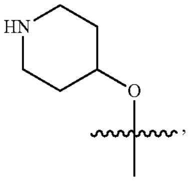, 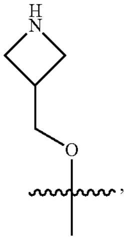, or 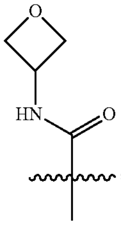, and wherein the remaining variables are as described above for Formula I or any one of the second to eighth embodiments.

As part of a tenth embodiment, for the compounds of Formula I, or a pharmaceutically acceptable salt thereof, X is —O$R^6$, and wherein the remaining variables are as described above for Formula I or any one of the second to ninth embodiments.

As part of an eleventh embodiment, for the compounds of Formula I, or a pharmaceutically acceptable salt thereof, $R^6$ is $(C_1\text{-}C_4)$alkylene$(C_1\text{-}C_4$alkoxy), $(C_1\text{-}C_4)$alkylene[aryl], or $(C_1\text{-}C_4)$alkylene[heteroaryl], wherein the aryl is substituted by $R^{2A}$, and the heteroaryl is pyridinyl, oxazolyl, pyrazolyl, imidazolyl, triazolyl, or oxadiazolyl, each of which is optionally substituted by $R^{2A}$, and wherein the remaining variables are as described above for Formula I or any one of the second to tenth embodiments. Alternatively, as part of the eleventh embodiment, for the compounds of Formula I, or a pharmaceutically acceptable salt thereof, $R^6$ is —$CH_2CH_2OCH_3$, —$CH_2CH_2CH_2OCH_3$,

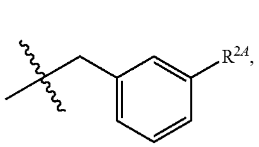, 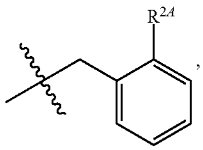,

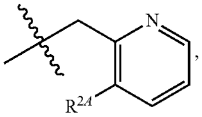, 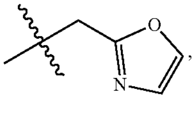,

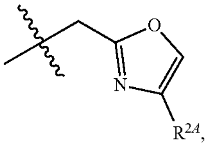, 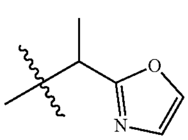,

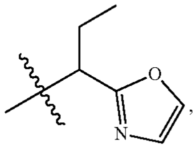, 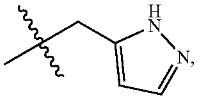,

-continued

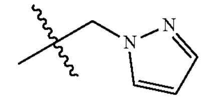, 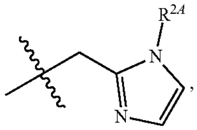, 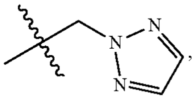, 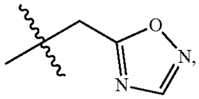, or 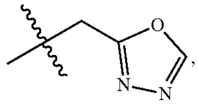, and wherein the remaining variables are as described above for Formula I or any one of the second to tenth embodiments.

As part of a twelfth embodiment, for the compounds of Formula I, or a pharmaceutically acceptable salt thereof, each $R^{2A}$ is independently $(C_1\text{-}C_4)$alkyl, halo$(C_1\text{-}C_4)$alkyl, or $(C_1\text{-}C_4)$alkoxy, and wherein the remaining variables are as described above for Formula I or any one of the second to eleventh embodiments. Alternatively, as part of the twelfth embodiment, for the compounds of Formula I, or a pharmaceutically acceptable salt thereof, each $R^{2A}$ is independently $—CH_3$, $—CF_3$, $—OCH_3$, and wherein the remaining variables are as described above for Formula I or any one of the second to eleventh embodiments.

As part of a thirteenth embodiment, for the compounds of Formula I, or a pharmaceutically acceptable salt thereof, X is $—NR^7R^8$, and wherein the remaining variables are as described above for Formula I or any one of the second to ninth embodiments.

As part of a fourteenth embodiment, for the compounds of Formula I, or a pharmaceutically acceptable salt thereof, $R^7$ is H and $R^8$ is cyclobutyl, oxetanyl, $(C_1\text{-}C_4)$alkylene[aryl], or $(C_1\text{-}C_4)$alkylene[heteroaryl], wherein the heteroaryl is oxazolyl, and wherein the cyclobutyl is optionally substituted by $R^{2A}$, and wherein the remaining variables are as described above for Formula I or any one of the second to ninth or thirteenth embodiments. Alternatively, as part of the fourteenth embodiment, for the compounds of Formula I, or a pharmaceutically acceptable salt thereof, $R^7$ is H and $R^8$ is:

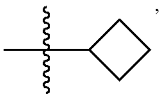, 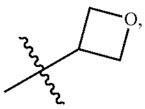, 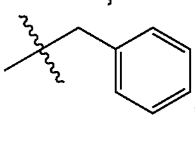, or 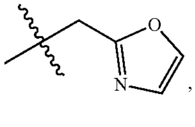, wherein the cyclobutyl is optionally substituted by 1 $R^{2A}$, and wherein the cyclobutyl is optionally substituted by $R^{2A}$, and wherein the remaining variables are as described above for Formula I or any one of the second to ninth or thirteenth embodiments. Alternatively, as part of the fourteenth embodiment, for the compounds of Formula I, or a pharmaceutically acceptable salt thereof, $R^7$ is H and $R^8$ is:

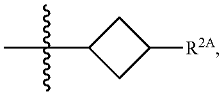, 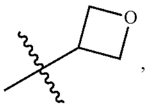, 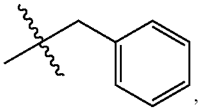, or 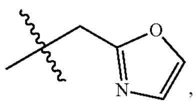, and wherein the remaining variables are as described above for Formula I or any one of the second to ninth or thirteenth embodiments. Alternatively, as part of the fourteenth embodiment, for the compounds of Formula I, or a pharmaceutically acceptable salt thereof, $R^7$ and $R^8$ are taken together to form heterocyclyl optionally substituted with 1 or 3 $R^{2A}$, and wherein the remaining variables are as described above for Formula I or any one of the second to ninth or thirteenth embodiments. Alternatively, as part of the fourteenth embodiment, for the compounds of Formula I, or a pharmaceutically acceptable salt thereof, $R^7$ and $R^8$ are taken together to form azetidinyl, pyrrolidinyl, azabicyclohexanyl, azaspiroheptanyl, oxaazaspiroheptanyl, oxaazaspirooctanyl, or oxadiazaspirononanyl, each of which is optionally substituted with 1 or 2 $R^{2A}$, and wherein the remaining variables are as described above for Formula I or any one of the second to ninth or thirteenth embodiments. Alternatively, as part of the fourteenth embodiment, for the compounds of Formula I, or a pharmaceutically acceptable salt thereof, $R^7$ and $R^8$ are taken together to form:

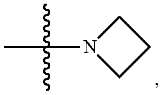, 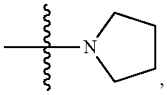, 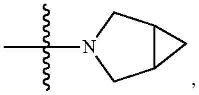, 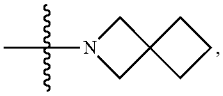, 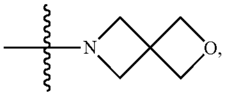, 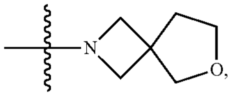, 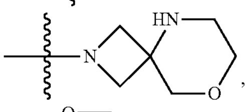, or 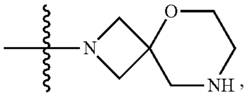, each of which is optionally substituted with 1 or 2 $R^{2A}$, and wherein the remaining variables are as described above for Formula I or any one of the second to ninth or thirteenth embodiments. Alternatively, as part of the fourteenth embodiment, for the compounds of Formula I, or a pharmaceutically acceptable salt thereof, $R^7$ and $R^8$ are taken together to form:

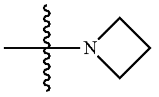, 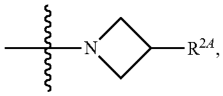, 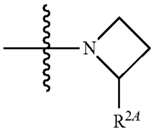, 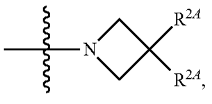,

-continued

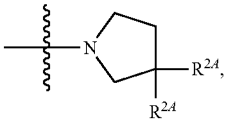
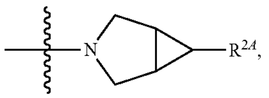
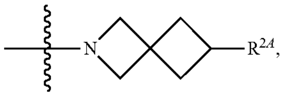
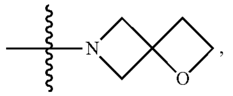
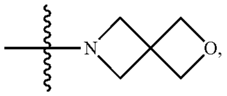
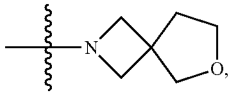
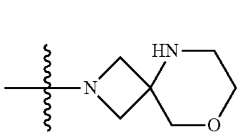
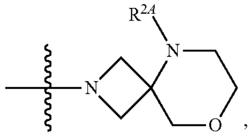
or
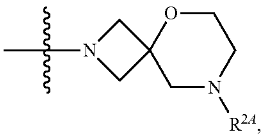

and wherein the remaining variables are as described above for Formula I or any one of the second to ninth or thirteenth embodiments.

As part of a fifteenth embodiment, for the compounds of Formula I, or a pharmaceutically acceptable salt thereof, each $R^{2A}$ is independently halo, $(C_1-C_4)$alkyl, halo$(C_1-C_4)$alkyl, $(C_1-C_4)$alkylene$(C_1-C_4)$alkoxy, $(C_1-C_4)$alkylene[deuterated$(C_1-C_4)$alkoxy], $(C_1-C_4)$alkylene[halo$(C_1-C_4)$alkoxy], hydroxy, $(C_1-C_4)$alkoxy, halo$(C_1-C_4)$alkoxy, deuterated$(C_1-C_4)$alkoxy, —O[cycloalkyl], cyano, $—S(O)_2(C_1-C_4)$alkyl, aryl, or heteroaryl, wherein the heteroaryl is optionally substituted with $(C_1-C_4)$alkyl or $(C_1-C_4)$alkoxy, and wherein the remaining variables are as described above for Formula I or any one of the second to ninth, thirteenth, or fourteenth embodiments. Alternatively, as part of the fifteenth embodiment, for the compounds of Formula I, or a pharmaceutically acceptable salt thereof, each $R^{2A}$ independently is —F, $—CH_3$, $—CHF_2$, $—CF_3$, $—CF_2CH_3$, $—CH_2OCH_3$, $—CH_2OCD_3$, $—CH(CH_3)OCH_3$, $—C(CH_3)_2OCH_3$, $—CH_2OCF_3$, hydroxy, $—OCH_3$, $—OCD_3$, $—OCHF_2$,

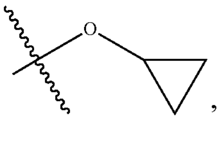 [SMILES: *OC1CC1], cyano, $—S(O_2)CH_3$, phenyl,

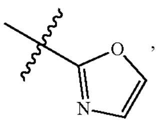,
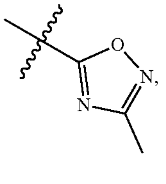
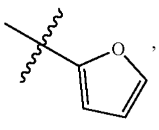,

-continued

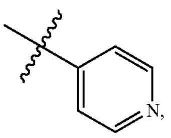
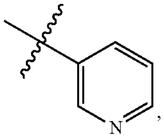
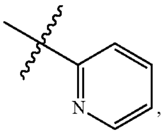
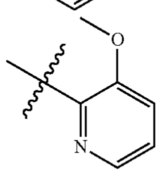, or
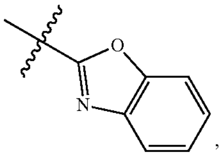, and wherein the remaining variables are as described above for Formula I or any one of the second to ninth, thirteenth, or fourteenth embodiments.

As part of a sixteenth embodiment, the compounds of Formula I have the structural Formula II:

(II)

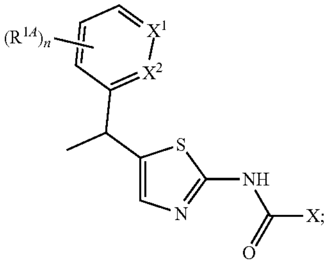

or a pharmaceutically acceptable salt thereof, wherein:

one of $X^1$ or $X^2$ is N, and the other is CH;

n is 1 or 2;

each $R^{1A}$ is independently halo, $(C_1-C_4)$alkyl, halo$(C_1-C_4)$alkyl, $(C_1-C_4)$alkoxy, deuterated$(C_1-C_4)$alkoxy, halo$(C_1-C_4)$alkoxy, or —O[cycloalkyl];

X is $—OR^6$;

$R^6$ is $(C_1-C_3)$alkylene[heteroaryl], wherein the heteroaryl is optionally substituted with 1 to 3 groups selected from $R^{2A}$, and wherein the remaining variables are as described above for Formula I.

As part of a seventeenth embodiment, for the compounds of Formula II, or a pharmaceutically acceptable salt thereof, $X^1$ is N and $X^2$ is CH, and wherein the remaining variables are as described above for Formula II.

As part of an eighteenth embodiment, for the compounds of Formula I or II, or a pharmaceutically acceptable salt thereof, each $R^{1A}$ is independently —Cl, $—CH_3$, $—CF_3$, $—OCH_3$, $—OCH_2CH_3$, $—OCH(CH_3)_2$, —O-cyclopropyl, $—OCHF_2$, $—OCF_3$, or $—OCD_3$, and wherein the remaining variables are as described above for Formula I or II or the sixteenth or seventeenth embodiment. Alternatively, as part of the eighteenth embodiment, for the compounds of Formula I or II, or a pharmaceutically acceptable salt thereof, each $R^{1A}$ is independently $(C_1-C_4)$alkoxy, and wherein the remaining variables are as described above for Formula I or II or the sixteenth or seventeenth embodiment.

As part of a nineteenth embodiment, for the compounds of Formula I or II, or a pharmaceutically acceptable salt thereof, n is 1, and wherein the remaining variables are as described above for Formula I or II or any one of the sixteenth to eighteenth embodiments.

As part of a twentieth embodiment, for the compounds of Formula I or II, or a pharmaceutically acceptable salt thereof, $R^6$ is $(C_1-C_3)$alkylene[5- to 6-membered heteroaryl], wherein the 5- to 6-membered heteroaryl is optionally substituted with 1 to 3 groups selected from $R^{2A}$, and wherein the remaining variables are as described above for Formula I or II or any one of the sixteenth to nineteenth embodiments. Alternatively, as part of the twentieth embodiment, for the compounds of Formula I or II, or a pharmaceutically acceptable salt thereof, $R^6$ is $(C_1-C_3)$alkylene [oxazolyl], wherein the oxazolyl is optionally substituted with 1 to 3 groups selected from $R^{2A}$, and wherein the remaining variables are as described above for Formula I or II or any one of the sixteenth to nineteenth embodiments.

As part of a twenty-first embodiment, for the compounds of Formula I or II, or a pharmaceutically acceptable salt thereof, each $R^{2A}$ is independently $(C_1-C_4)$alkyl or halo$(C_1-C_4)$alkyl, and wherein the remaining variables are as described above for Formula I or II or any one of the sixteenth to twentieth embodiments.

As part of a twenty-second embodiment, for the compounds of Formula I or II, or a pharmaceutically acceptable salt thereof, $R^6$ is $-CH_2$[oxazole-2-yl], and wherein the remaining variables are as described above for Formula I or II or any one of the sixteenth to twenty-first embodiments.

As part of a twenty-third embodiment, the compounds of Formula I or II have the structural Formula III:

(III)

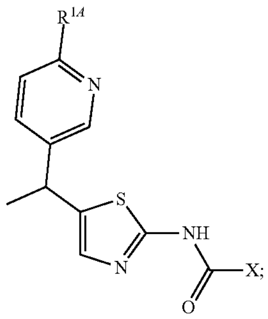

or a pharmaceutically acceptable salt thereof, and wherein the remaining variables are as described above for Formula I or II or any one of the sixteenth to twenty-second embodiments.

As part of a twenty-fourth embodiment, the compounds of Formula I, II, or III have the structural Formula IIIa:

(IIIa)

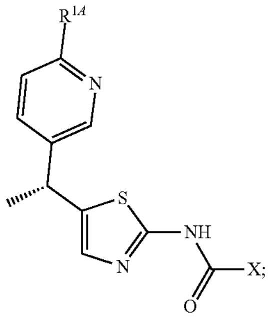

or a pharmaceutically acceptable salt thereof, and wherein the remaining variables are as described above for Formula I, II, or III or any one of the sixteenth to twenty-third embodiments.

As part of a twenty-fifth embodiment, the for the compounds of Formula I, II, III, or IIIa, or a pharmaceutically acceptable salt thereof, $R^{1A}$ is $-OCH_3$, and wherein the remaining variables are as described above for Formula I, II, III, or IIIa, or any one of the sixteenth to twenty-fourth embodiments.

As part of the twenty-sixth embodiment, the compounds of Formula I is any one of Examples 1 to 164, or a pharmaceutically acceptable salt thereof.

Additional compounds are described and exemplified herein, and are included in the present disclosure. Pharmaceutically acceptable salts thereof as well as the neutral forms of such compounds are included.

4. Uses, Formulation and Administration

The compounds and compositions described herein are generally useful for modulating the activity of beta catenin. In some aspects, the compounds, pharmaceutical acceptable salts, and pharmaceutical compositions described herein sequester beta catenin in nuclear condensates. In some aspects, the compounds, pharmaceutical acceptable salts, and pharmaceutical compositions described herein modulate beta catenin condensates.

In some aspects, the compounds and pharmaceutical compositions described herein are useful in treating a disease or condition associated with beta catenin function. Thus, provided herein are methods of treating a disease or condition associated with beta catenin function, comprising administering to a subject in need thereof, a therapeutically effective amount of a compound described herein, or a pharmaceutically acceptable salt thereof, or a pharmaceutical composition comprising a disclosed compound or pharmaceutically acceptable salt thereof. In some aspects, the compounds and pharmaceutical compositions described herein are useful in treating a disease or condition associated with the modulation of beta catenin condensates. Thus, provided herein are methods of treating a disease or condition associated with the modulation of beta catenin condensates, comprising administering to a subject in need thereof, a therapeutically effective amount of a compound described herein, or a pharmaceutically acceptable salt thereof, or a pharmaceutical composition comprising a disclosed compound or pharmaceutically acceptable salt thereof.

Also provided is the use of a compound described herein, or a pharmaceutically acceptable salt thereof, or a pharmaceutical composition comprising a disclosed compound or pharmaceutically acceptable salt thereof, for the manufacture of a medicament for treating a disease or condition associated with beta catenin function. Also provided is a compound described herein, or a pharmaceutically acceptable salt thereof, or a pharmaceutical composition comprising a disclosed compound or pharmaceutically acceptable salt thereof, for use in treating a disease or condition associated with beta catenin. Also provided is the use of a compound described herein, or a pharmaceutically acceptable salt thereof, or a pharmaceutical composition comprising a disclosed compound or pharmaceutically acceptable salt thereof, for the manufacture of a medicament for treating a disease or condition associated with the modulation of beta catenin condensates. Also provided is a compound described herein, or a pharmaceutically acceptable salt thereof, or a pharmaceutical composition comprising a disclosed compound or pharmaceutically acceptable salt thereof, for use in treating a disease or condition associated with the modulation of beta catenin condensates.

In one aspect, the disease or condition associated with beta catenin or the modulation of beta catenin condensates is cancer. In embodiments, the cancer is bladder cancer, breast cancer, colorectal cancer, endometrial cancer, gastric cancer, head and neck cancer, leukemia, liver cancer, lung cancer, ovarian cancer, pancreatic cancer, or a solid tumor. In embodiments, the breast cancer is triple negative breast cancer. In embodiments, the leukemia is chronic lymphocytic leukemia or acute myeloid leukemia. In embodiments, the lung cancer is non-small cell lung cancer.

In some aspects, the compounds, pharmaceutical acceptable salts, and pharmaceutical compositions described herein modulate the function of beta catenin. In some aspects, modulating beta catenin comprises modulating beta catenin partitioning into condensates. In some aspects, modulating beta catenin comprises modulating transcription of beta catenin-dependent genes. In some aspects, modulating beta catenin comprises modulating beta catenin association with chromatin. In some aspects, modulating beta catenin comprises modulating beta catenin interaction network. In some aspects, modulating beta catenin comprises modulating beta catenin posttranscriptional modification status. In some aspects, modulating beta catenin comprises modulating direct and indirect regulators of beta catenin and the WNT pathway. In some aspects, modulating beta catenin comprises modulating the cell cycle.

In certain aspects, a pharmaceutical composition described herein is formulated for administration to a patient in need of such composition. Pharmaceutical compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the pharmaceutical compositions described herein may be aqueous or oleaginous suspension. These suspensions may be formulated according to techniques known in the art using suitable dispersing or wetting agents and suspending agents.

In some aspects, the pharmaceutical compositions are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the pharmaceutical composition.

EXEMPLIFICATION

While there is described herein a number of embodiments, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Intermediate Synthesis

1-(6-(Trifluoromethoxy)pyridin-3-yl)ethan-1-one

Step 1

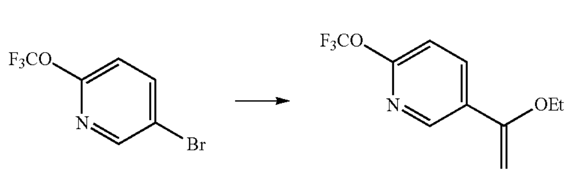 [SMILES: FC(F)(F)Oc1ccc(Br)cn1 ; C=C(OCC)c1ccc(OC(F)(F)F)nc1]

$Pd(PPh_3)_2Cl_2$ (1.02 g, 1.45 mmol) was added to a solution of tributyl(1-ethoxyvinyl)stannane (7.84 g, 21.7 mmol) and 5-bromo-2-(trifluoromethoxy)pyridine (3.50 g, 14.5 mmol) in DMF (30 mL). The resulting mixture was stirred at 100° C. for 16 h. Saturated aqueous potassium fluoride solution (40 mL) was added and the mixture was extracted into EtOAc (3×40 mL). The combined organic extracts were washed with brine (2×20 mL), dried over anhydrous sodium sulfate and concentrated in vacuo to afford 5-(1-ethoxyvinyl)-2-(trifluoromethoxy)pyridine (3 g, crude) as a yellow oil.

Step 2

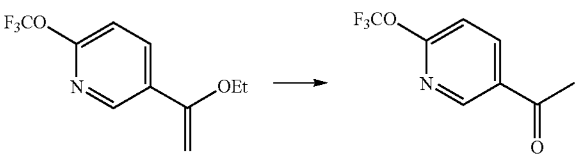 [SMILES: C=C(OCC)c1ccc(OC(F)(F)F)nc1 ; CC(=O)c1ccc(OC(F)(F)F)nc1]

Aqueous hydrochloric acid (2.0 M, 32.2 mL, 64.2 mmol) was added to a solution of 5-(1-ethoxyvinyl)-2-(trifluoromethoxy)pyridine (3 g crude from step 1) in THF (30 mL) and the resulting mixture was stirred at 20° C. for 2 h. Saturated aqueous sodium bicarbonate solution (100 mL) was added and the mixture was extracted into EtOAc (2×50 mL). The combined organic extracts were dried over anhydrous sodium sulfate and concentrated in vacuo. Purification by flash column chromatography on silica (EtOAc:PE, 0:1 to 1:5) afforded 1-(6-(trifluoromethoxy)pyridin-3-yl)ethan-1-one (2.60 g, 88% over two steps) as a yellow oil; ES-MS $[M+H]^+$: 206.2.

The following intermediate was prepared in an analogous manner. All intermediates are commercially available unless noted.

| Name | Structure | Intermediates | ES-MS [M + H]$^+$ |
|---|---|---|---|
| 1-(2-(difluoromethoxy)pyrimidin-5-yl)ethan-1-one | 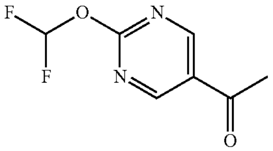 | requiring synthesis 5-bromo-2-(difluoromethoxy) pyrimidine | 189.0 |

5-Bromo-2-(difluoromethoxy)pyrimidine

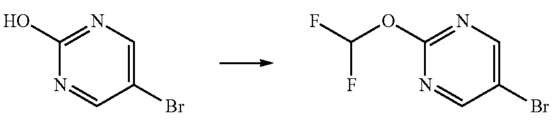 [SMILES: Oc1ncc(Br)cn1 ; FC(F)Oc1ncc(Br)cn1]

Diethyl (bromodifluoromethyl)phosphonate (50.2 g, 188 mmol) was added to a solution of 5-bromopyrimidin-2-ol (25.0 g, 143 mmol) and potassium fluoride (25.0 g, 430 mmol) in acetonitrile (250 mL). The reaction mixture was stirred at 25° C. for 12 h, then diluted with water (500 mL) and extracted into EtOAc (2×500 mL). The combined organic extracts were washed with brine (500 mL), dried over anhydrous sodium sulfate and then concentrated in vacuo. Purification by flash column chromatography on silica (THF:PE, 0:1 to 1:4) afforded 5-bromo-2-(difluoromethoxy)pyrimidine (6.50 g, 28.9 mmol) as a yellow oil; ES-MS [M+H]$^+$: 227.0.

1-(6-(Methoxy-d3)pyridin-3-yl)ethan-1-one

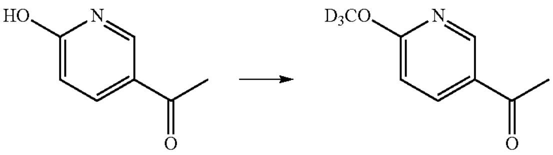

Iodomethane-d3 (15.9 g, 109 mmol) was added to a solution of 1-(6-hydroxypyridin-3-yl)ethan-1-one (10.0 g, 72.9 mmol) and silver oxide (33.8 g, 146 mmol) in acetonitrile (100 mL). The resulting mixture was stirred at 80° C. for 2 h, then filtered and concentrated in vacuo. Purification by flash column chromatography on silica (EtOAc:PE, 0:1 to 1:4) afforded 1-(6-(methoxy-d3)pyridin-3-yl)ethan-1-one (4.20 g, 37%) as a white solid; ES-MS [M+H]$^+$: 155.3.

1-(6-Methoxy-5-(trifluoromethyl)pyridin-3-yl)ethan-1-one

Step 1

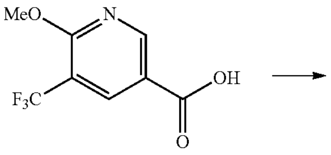

-continued

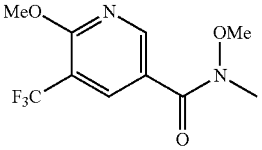

Methoxy(methyl)amine hydrochloride (2.51 g, 25.8 mmol) was added to a solution of 6-methoxy-5-(trifluoromethyl)nicotinic acid (3.80 g, 17.2 mmol) and HATU (9.80 g, 25.8 mmol) in DMF (30 mL). The reaction mixture was stirred at 25° C. for 1 h, then diluted with water (100 mL) and extracted into EtOAc (3×100 mL). The combined organic extracts were washed with brine (2×200 mL), dried over anhydrous sodium sulfate and concentrated in vacuo. Purification by flash column chromatography on silica (EtOAc:PE, 0:1 to 35:65) afforded N,6-dimethoxy-N-methyl-5-(trifluoromethyl)nicotinamide (5.60 g, 81%) as a yellow oil; ES-MS [M+H]$^+$: 265.0.

Step 2

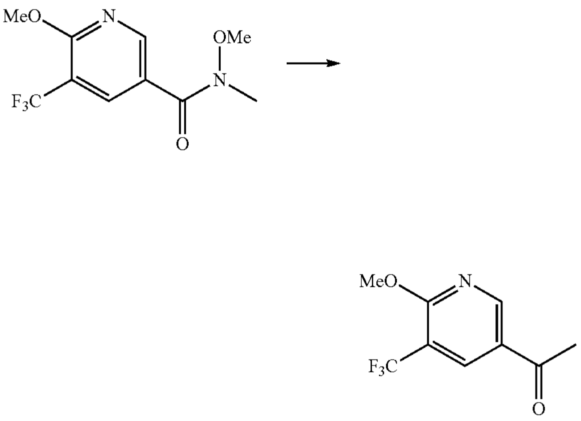

Methylmagnesium bromide (3.0 M in THF, 10.6 mL, 31.8 mmol) was added to a solution of N,6-dimethoxy-N-methyl-5-(trifluoromethyl)nicotinamide (5.60 g, 21.2 mmol) in THF (100 mL) at 0° C. The reaction mixture was stirred at 0° C. for 1 h, then quenched by addition of saturated aqueous ammonium chloride solution (100 mL) and extracted into EtOAc (3×100 mL). The combined organic extracts were dried over anhydrous sodium sulfate and concentrated in vacuo. Purification by flash column chromatography on silica (EtOAc:PE, 0:1 to 1:4) afforded 1-(6-methoxy-5-(trifluoromethyl)pyridin-3-yl)ethan-1-one (4.0 g, 84%) as a white solid; ES-MS [M+H]$^+$: 220.0.

The following intermediate was prepared in an analogous manner:

| Name | Structure | Starting materials | $^1$H NMR |
| --- | --- | --- | --- |
| (4-chlorophenyl)(oxetan-3-yl)methanone | 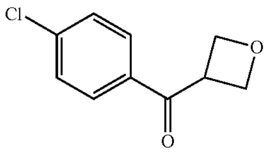 [SMILES: O=C(c1ccc(Cl)cc1)C1COC1] | Step 1: oxetane-3-carboxylic acid<br>Step 2: 4-chlorophenylmagnesium bromide | $\delta_H$(400 MHz; $CDCl_3$); 7.75 (2H, d, J 8.5 Hz), 7.48 (2H, d, J 8.5 Hz), 5.05-4.93 (4H, m), 4.72-4.52 (1H, m) |

1-(6-Methoxy-4-methylpyridin-3-yl)ethan-1-one

Step 1

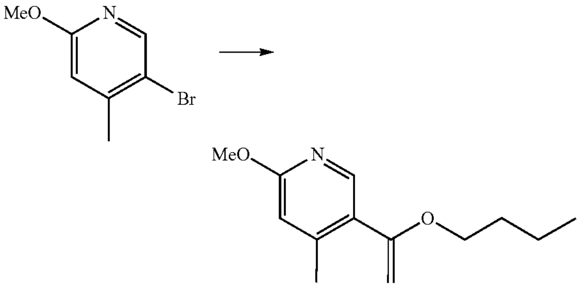

$Pd(PPh_3)_2Cl_2$ (625 mg, 0.89 mmol) was added to a solution of 5-bromo-2-methoxy-4-methylpyridine (9.00 g, 44.5 mmol), butyl vinyl ether (5.80 g, 57.9 mmol) and potassium carbonate (18.5 g, 133.6 mmol) in DMF (100 mL) and water (5 mL). The resulting mixture was stirred at 100° C. for 12 h. Water (150 mL) was added and the mixture was extracted into EtOAc (3×50 mL). The combined organic extracts were washed with brine (50 mL), dried over anhydrous sodium sulfate and concentrated in vacuo to afford 5-(1-butoxyvinyl)-2-methoxy-4-methylpyridine (9.20 g, crude) as a yellow oil.

Step 2

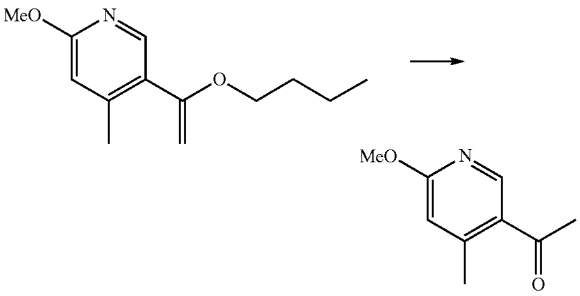

Aqueous hydrochloric acid (3.0 M, 50.0 mL, 150 mmol) was added to a solution of 5-(1-butoxyvinyl)-2-methoxy-4-methylpyridine (9.20 g crude from step 1) in THF (50 mL) and the resulting mixture was stirred at 25° C. for 2 h. Saturated aqueous sodium carbonate solution (100 mL) was added and the mixture was extracted into EtOAc (3×50 mL). The combined organic extracts were dried over anhydrous sodium sulfate and concentrated in vacuo. Purification by flash column chromatography on silica (EtOAc:PE, 0:1 to 10:1) afforded 1-(6-methoxy-4-methylpyridin-3-yl)ethan-1-one (3.70 g, 54% over two steps) as a yellow solid; $\delta_H$ (400 MHz; $CDCl_3$); 8.66 (1H, s), 6.59 (1H, s), 3.98 (3H, s), 2.58 (3H, s), 2.55 (3H, s).

(4-(Trifluoromethyl)oxazol-2-yl)methanol

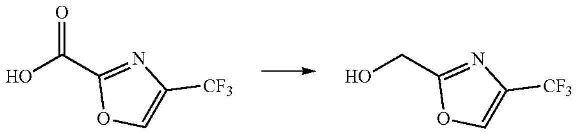 [SMILES: O=C(O)c1nc(C(F)(F)F)co1 ; OCc1nc(C(F)(F)F)co1]

Borane tetrahydrofuran complex (1.0 M in THF, 3.31 mL, 3.31 mmol) was added to a solution of 4-(trifluoromethyl) oxazole-2-carboxylic acid (200 mg, 1.10 mmol) in THF (2 mL) at 0° C. and the resulting mixture was stirred at 25° C. for 16 h. Water (2 mL) was added at 0° C. and the mixture was extracted into EtOAc (3×10 mL). The combined organic extracts were washed with brine (10 mL), dried over anhydrous sodium sulfate and concentrated in vacuo to afford (4-(trifluoromethyl)oxazol-2-yl)methanol (130 mg, 70%) as a white solid; $\delta_H$ (400 MHz; $CDCl_3$); 8.00 (1H, m), 4.81 (2H, m).

1-(Oxazol-2-yl)propan-1-ol

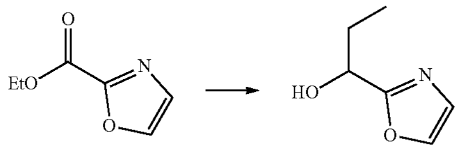

Ethylmagnesium bromide (3.0 in $Et_2O$, 13.2 mL, 39.6 mmol) was added dropwise to a solution of ethyl oxazole-2-carboxylate (2.00 g, 14.2 mmol) and titanium(IV) isopropoxide (5.86 mL, 19.8 mmol) in THF (90 mL) at 0° C. The resulting mixture was stirred at 25° C. for 16 h. Water (30 mL) was added and precipitates were removed by filtration. The filtrate was extracted into EtOAc (3×40 mL). The combined organic extracts were washed with brine (40 mL), dried over anhydrous sodium sulfate and concentrated in vacuo. Purification by flash column chromatography on silica (EtOAc:PE, 0:1 to 1:0) afforded 1-(oxazol-2-yl)propan-1-ol (370 mg, 2.91 mmol) as an orange oil; $\delta_H$ (400 MHz; DMSO-d6) 8.02 (1H, s), 7.14 (1H, s), 5.64 (1H, m), 4.51 (1H, m), 1.86-1.69 (2H, m), 0.84 (3H, m).

(1-((2-(Trimethylsilyl)ethoxy)methyl)-1H-1,2,4-triazol-3-yl)methanol

Step 1

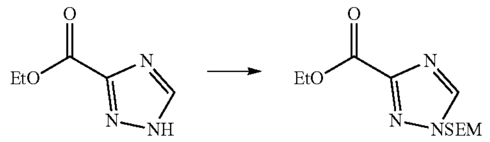 [SMILES: CCOC(=O)c1nc[nH]n1 ; CCOC(=O)c1ncn(COCC[Si](C)(C)C)n1]

A solution of ethyl 1H-1,2,4-triazole-3-carboxylate (1.00 g, 7.09 mmol) in DMF (25 mL) was added dropwise to a suspension of sodium hydride (60% dispersion in oil, 340 mg, 8.50 mmol) in DMF (9 mL) at 0° C. and the resulting mixture was stirred at this temperature for 30 min. 2-(Trimethylsilyl)ethoxymethyl chloride (1.30 g, 7.79 mmol) was added at 0° C. and the reaction mixture was stirred at 25° C. for 1 h. Saturated aqueous ammonium chloride solution (50 mL) was added at 0° C. and the mixture was extracted into EtOAc (3x25 mL). The combined organic extracts were washed with brine (80 mL), dried over anhydrous sodium sulfate and then concentrated in vacuo. Purification by flash column chromatography on silica (EtOAc:PE, 0:1 to 1:4) afforded ethyl 1-((2-(trimethylsilyl)ethoxy)methyl)-1H-1,2,4-triazole-3-carboxylate as a colorless oil; $\delta_H$ (400 MHz; $CDCl_3$); 8.01 (1H, s), 5.91 (2H, s), 4.49 (2H, m), 3.71-3.60 (2H, m), 1.45 (3H, m), 0.95-0.89 (2H, m), −0.03 (9H, s).

Step 2

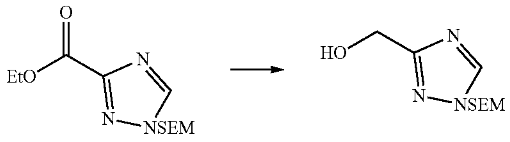 [SMILES: CCOC(=O)c1ncn(COCC[Si](C)(C)C)n1 ; C[Si](C)(C)CCOCn1cnc(CO)n1]

Lithium borohydride (2.0 M in THF, 3.32 mL, 6.64 mmol) was added to a solution of ethyl 1-((2-(trimethylsilyl)ethoxy)methyl)-1H-1,2,4-triazole-3-carboxylate (300 mg, 1.11 mmol) in THF (8 mL) at 0° C. and the resulting mixture was stirred at 20° C. for 2 h. Saturated aqueous ammonium chloride solution (50 mL) was added at 0° C. and the mixture was extracted into EtOAc (3x25 mL). The combined organic extracts were washed with brine (30 mL), dried over anhydrous sodium sulfate and then concentrated in vacuo to afford (1-((2-(trimethylsilyl)ethoxy)methyl)-1H-1,2,4-triazol-3-yl)methanol as a colorless oil; $\delta_H$-(400 MHz; $CDCl_3$); 7.83 (1H, s), 5.56 (2H, s), 4.85 (2H, s), 3.64-3.58 (2H, m), 0.95-0.85 (2H, m), −0.03 (9H, s).

3-(Azetidin-1-yl)-4-chlorobenzaldehyde

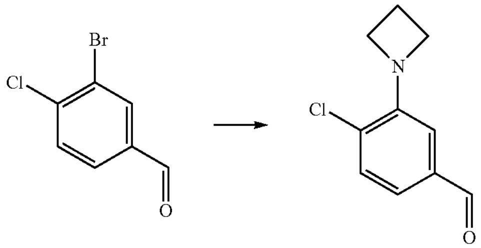 [SMILES: O=Cc1ccc(Cl)c(Br)c1 ; O=Cc1ccc(Cl)c(N2CCC2)c1]

Azetidine hydrochloride (1.28 g, 13.7 mmol) was added to a mixture of 3-bromo-4-chlorobenzaldehyde (2.00 g, 9.11 mmol), cesium carbonate (8.91 g, 27.3 mmol), $Pd_2(dba)_3$ and BINAP (1.13 g, 1.82 mmol) in toluene (40 mL). The reaction mixture was stirred at 80° C. for 12 h, then diluted with water (20 mL) and extracted into EtOAc (2x20 mL). The combined organic extracts were dried over anhydrous sodium sulfate and then concentrated in vacuo. Purification by flash column chromatography on silica (EtOAc:PE, 0:1 to 1:10) afforded 3-(azetidin-1-yl)-4-chlorobenzaldehyde (1.40 g, 74%) as a yellow oil; ES-MS $[M+H]^+$: 196.2.

The following intermediate was prepared in an analogous manner:

| Name | Structure | Starting material | ES-MS $[M + H]^+$ |
|---|---|---|---|
| benzyl 4-(2-chloro-5-formylphenyl)piperazine-1-carboxylate | 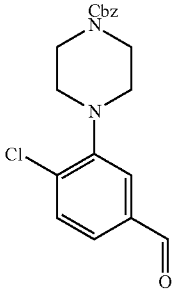 [SMILES: O=Cc1ccc(Cl)c(N2CCN(C(=O)OCc3ccccc3)CC2)c1] | benzyl piperazine-1-carboxylate | 359.1 |

1-(4-((Triisopropylsilyl)oxy)phenyl)ethan-1-one

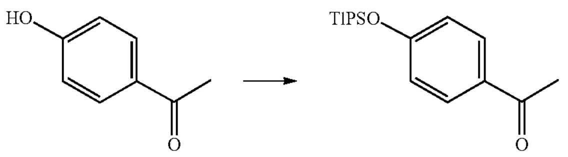

Triisopropylsilyl chloride (7.79 g, 40.4 mmol) was add to a solution of 1-(4-hydroxyphenyl)ethan-1-one (5.00 g, 36.7 mmol) and imidazole (5.50 g, 80.8 mmol) in dichloromethane (50 mL). The reaction mixture was stirred at 25° C. for 3 h, then diluted with water (500 mL) and extracted into EtOAc (2×300 mL). The combined organic extracts were dried over anhydrous sodium sulfate and then concentrated in vacuo. Purification by flash column chromatography on silica (EtOAc:PE, 0:1 to 1:19) afforded 1-(4-((triisopropylsilyl)oxy)phenyl)ethan-1-one (10.2 g, 95%) as a white solid; $\delta_H$ (400 MHz; DMSO-d6) 7.95-7.83 (2H, m), 7.01-6.85 (2H, m), 2.50 (3H, s), 1.29-1.23 (3H, m), 1.05 (18H, d, J 7.3 Hz).

1-(4-chloro-3-((2-methoxyethyl)(methyl)amino)phenyl)ethan-1-one

Step 1

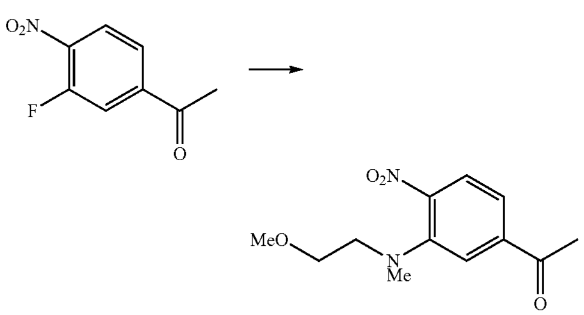

2-Methoxy-N-methylethan-1-amine (6.33 g, 71.0 mmol) was added to a solution of 1-(3-fluoro-4-nitrophenyl)ethan-1-one (10.0 g, 54.6 mmol) and potassium carbonate (22.6 g, 164 mmol) in acetonitrile (100 mL). The resulting mixture was stirred at 80° C. for 2 h, then filtered and concentrated in vacuo to afford 1-(3-((2-methoxyethyl)(methyl)amino)-4-nitrophenyl)ethan-1-one (10.0 g, crude) as a brown oil; ES-MS $[M+H]^+$: 253.2.

Step 2

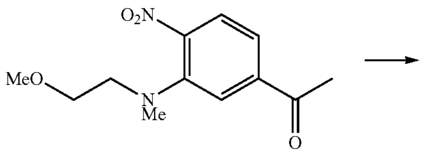

-continued

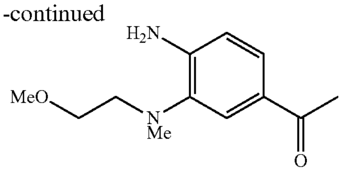

Iron (5.98 g, 107 mmol) and ammonium chloride (5.73 g, 107 mmol) were added to a solution of 1-(3-((2-methoxyethyl)(methyl)amino)-4-nitrophenyl)ethan-1-one (10.0 g, crude from Step 1) in ethanol (100 mL) and water (20 mL). The reaction mixture was stirred at 80° C. for 2 h, then filtered and concentrated in vacuo. Purification by flash column chromatography on silica (EtOAc:PE, 0:1 to 1:1) afforded 1-(4-amino-3-((2-methoxyethyl)(methyl)amino)phenyl)ethan-1-one (7.00 g, 88%) as a yellow solid; $\delta_H$ (400 MHz; DMSO-d6) 7.54-7.45 (2H, m), 6.65 (1H, d, J 8.3 Hz), 5.83 (2H, s), 3.47 (2H, m), 3.29 (3H, s), 2.88 (2H, m), 2.65 (3H, s), 2.40 (3H, s).

Step 3

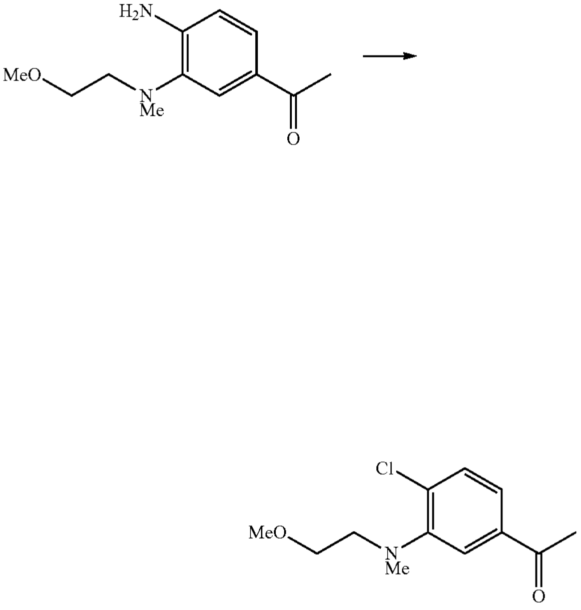 [SMILES: COCCN(C)c1cc(C(C)=O)ccc1N ; COCCN(C)c1cc(C(C)=O)ccc1Cl]

Tert-Butyl nitrite (2.09 g, 20.2 mmol) and copper(I) chloride (2.18 g, 16.2 mmol) were added to a solution of 1-(4-amino-3-((2-methoxyethyl)(methyl)amino)phenyl)ethan-1-one (3.0 g, 13.5 mmol) om acetonitrile (20 mL). The reaction mixture was stirred at 65° C. for 2 h, then quenched with saturated aqueous ammonium chloride solution (20 mL) and extracted into EtOAc (2×20 mL). The combined organic extracts were dried over anhydrous sodium sulfate and then concentrated in vacuo. Purification by flash column chromatography on silica (EtOAc:PE, 0:1 to 1:2) afforded 1-(4-chloro-3-((2-methoxyethyl)(methyl)amino)phenyl)ethan-1-one (1.20 g, 37%) as a yellow oil; ES-MS $[M+H]^+$: 242.2.

The following intermediate was prepared in an analogous manner:

| Name | Structure | Starting material | ES-MS [M + H]$^+$ |
| --- | --- | --- | --- |
| 1-(4-chloro-3-morpholinophenyl)ethan-1-one | 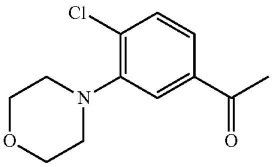 [SMILES: CC(=O)c1ccc(Cl)c(N2CCOCC2)c1] | morpholine | 240.1 |

2-(Azetidin-3-yl)benzo[d]oxazole TFA Salt

Step 1

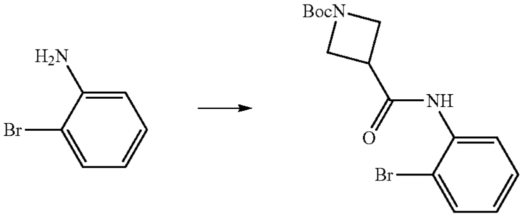 [SMILES: Nc1ccccc1Br ; CC(C)(C)OC(=O)N1CC(C(=O)Nc2ccccc2Br)C1]

EDC (1.67 g, 8.72 mmol) was added to a solution of 1-(tert-butoxycarbonyl)azetidine-3-carboxylic acid (1.29 g, 6.39 mmol), 2-bromoaniline (1.00 g, 5.81 mmol), DIPEA (3.04 mL, 17.4 mmol) and DMAP (71 mg, 0.58 mmol) in dichloromethane (10 mL). The reaction mixture was stirred at 25° C. for 2 h, then diluted with water (10 mL) and extracted into dichloromethane (3×10 mL). The combined organic extracts were washed with brine (30 mL), dried over anhydrous sodium sulfate and then concentrated in vacuo. Purification by flash column chromatography on silica (EtOAc:PE, 0:1 to 3:7) afforded tert-butyl 3-((2-bromophenyl)carbamoyl)azetidine-1-carboxylate (600 mg, 28%) as a yellow solid; $\delta_H$ (400 MHz; DMSO-d6) 9.65 (1H, s), 7.66 (1H, d, J 7.9 Hz), 7.57 (1H, br d, J 7.7 Hz), 7.42-7.34 (1H, m), 7.21-7.10 (1H, m), 4.09-3.88 (4H, m), 3.62-3.52 (1H, m), 1.39 (9H, s).

Step 2

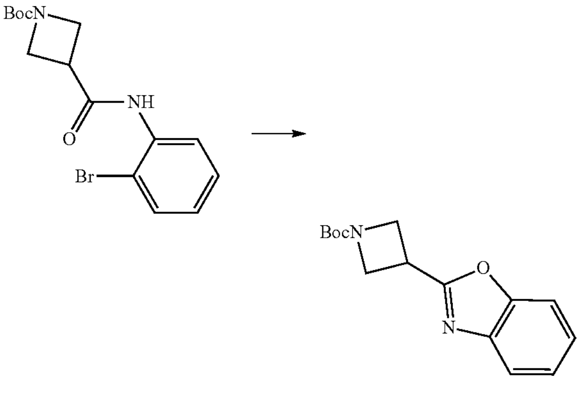

1,10-Phenanthroline (50 mg, 0.28 mmol) was added to a mixture of copper(I) iodide (26 mg, 0.14 mmol), cesium carbonate (917 mg, 2.82 mmol) and tert-butyl 3-((2-bromophenyl)carbamoyl)azetidine-1-carboxylate (500 mg, 1.41 mmol) in DMF (10 mL). The reaction mixture was stirred at 110° C. for 2 h, then diluted with water (20 mL) and extracted into EtOAc (3×10 mL). The combined organic extracts were washed with brine (30 mL), dried over anhydrous sodium sulfate and then concentrated in vacuo. Purification by flash column chromatography on silica (EtOAc:PE, 0:1 to 3:7) afforded tert-butyl 3-(benzo[d]oxazol-2-yl)azetidine-1-carboxylate (200 mg, 51%) as a yellow oil; $\delta_H$ (400 MHz; DMSO-d6) 7.77-7.68 (2H, m), 7.44-7.33 (2H, m), 4.29 (2H, br s), 4.22-4.09 (3H, m), 1.40 (9H, s).

Step 3

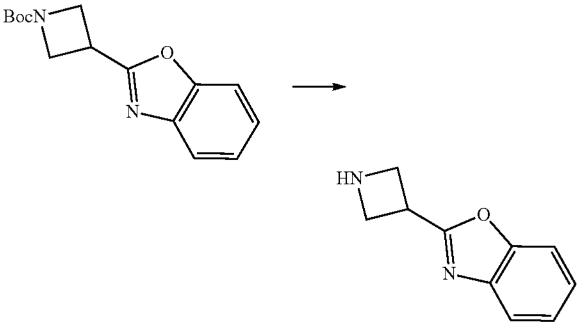

TFA salt

TFA (0.30 mL, 4.04 mmol) was added to a solution of tert-butyl 3-(benzo[d]oxazol-2-yl)azetidine-1-carboxylate (150 mg, 0.55 mmol) in dichloromethane (0.5 mL). The reaction mixture was stirred at 20° C. for 1 h, then concentrated in vacuo to afford 2-(azetidin-3-yl)benzo[d]oxazole TFA salt (200 mg, 0.49 mmol) as a yellow oil; $\delta_H$ (400 MHz; DMSO-d6) 7.82-7.63 (2H, m), 7.44-7.29 (2H, m), 4.18 (1H, m), 3.99-3.73 (4H, m).

3-Methoxy-3-(methoxymethyl)azetidine

Step 1

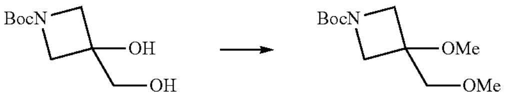 [SMILES: CC(C)(C)OC(=O)N1CC(O)(CO)C1 ; COCC1(OC)CN(C(=O)OC(C)(C)C)C1]

Sodium hydride (60% dispersion in oil, 30 mg, 0.75 mmol) was added to a solution of tert-butyl 3-hydroxy-3-(hydroxymethyl)azetidine-1-carboxylate (50 mg, 0.25 mmol) in THF (1 mL) at 0° C. The mixture was stirred at 25° C. for 30 min, then iodomethane (48 μL, 0.77 mmol) was added and stirring was continued at 25° C. for another 1 h. Saturated aqueous ammonium chloride solution (20 mL) was added and the mixture was extracted into EtOAc (3×20 mL). The combined organic extracts were dried over anhydrous sodium sulfate and then concentrated in vacuo to afford tert-butyl 3-methoxy-3-(methoxymethyl)azetidine-1-carboxylate (57 mg, crude) as a yellow oil; $\delta_H$ (400 MHz; $CDCl_3$) 3.92 (2H, d, J 9.4 Hz), 3.79 (2H, d, J 9.4 Hz), 3.59 (2H, s), 3.43 (3H, s), 3.33 (3H, s), 1.45 (9H, s).

Step 2

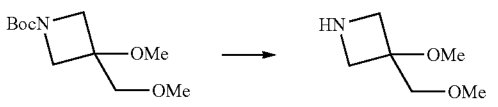 [SMILES: COCC1(OC)CN(C(=O)OC(C)(C)C)C1 ; COCC1(OC)CNC1]

TFA (0.20 mL, 2.69 mmol) was added to a solution of tert-butyl 3-methoxy-3-(methoxymethyl)azetidine-1-carboxylate (56 mg, crude) in dichloromethane (0.5 mL). The reaction mixture was stirred at 25° C. for 1 h, then diluted with water (50 mL) and extracted into EtOAc (2×50 mL). The combined organic extracts were concentrated in vacuo to afford 3-methoxy-3-(methoxymethyl)azetidine (30 mg, crude) as a yellow oil.

The following intermediates were prepared in an analogous manner:

| Name | Structure | $^1$H NMR of Step 1 product |
|---|---|---|
| 3-((methoxy-d3)methyl) azetidine TFA salt* | 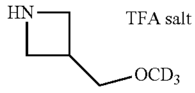 TFA salt | tert-butyl 3-((methoxy-d3)methyl) azetidine-1-carboxylate; $\delta_H$(400 MHz; $CDCl_3$) 4.03-3.94 (2H, m), 3.70-3.60 (2H, m), 3.51 (2H, d, J 6.8 Hz), 2.80-2.69 (1H, m), 1.50-1.41 (9H, m) |
| 3-(methoxy-d3) azetidine TFA salt* | 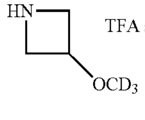 TFA salt | tert-butyl 3-(methoxy-d3)azetidine-1-carboxylate: $\delta_H$(400 MHz; DMSO-$d_6$) 4.16-4.08 (1H, m), 4.01-3.93 (2H, m), 3.63 (2H, br d, J 5.9 Hz), 1.37 (9H, s) |
| 3-fluoro-3-((methoxy-d3)methyl) azetidine TFA salt* | 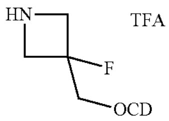 TFA salt | — |

* Aqueous workup replaced with concentration in vacuo in final step to afford TFA salt 6-Methoxy-3-azabicyclo[3.1.0]hexane HCl salt Step 1

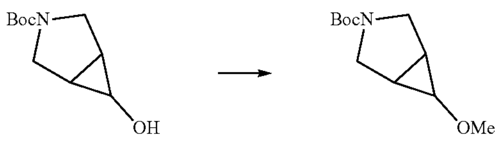 [SMILES: CC(C)(C)OC(=O)N1CC2C(O)C2C1 ; COC1C2CN(C(=O)OC(C)(C)C)CC21]

Sodium hydride (60% dispersion in oil, 161 mg, 4.02 mmol) was added to a solution tert-butyl 6-hydroxy-3-azabicyclo[3.1.0]hexane-3-carboxylate (400 mg, 2.01 mmol) in THF (4 mL) at 0° C. The mixture was stirred at 0° C. for 30 min, then iodomethane (187 μL, 3.01 mmol) was added and stirring was continued at 25° C. for another 16 h. Saturated aqueous ammonium chloride solution (10 mL) was added at 0° C. and the mixture was extracted into EtOAc (3×10 mL). The combined organic extracts were washed with brine (10 mL), dried over anhydrous sodium sulfate and then concentrated in vacuo. Purification by flash column chromatography on silica (EtOAc:PE, 0:1 to 7:13) afforded tert-butyl 6-methoxy-3-azabicyclo[3.1.0]hexane-3-carboxylate (230 mg, 54%) as a colorless oil; $\delta_H$ (400 MHz; $CDCl_3$) 3.59-3.48 (2H, m), 3.42-3.36 (2H, m), 3.35 (3H, s), 2.94 (1H, s), 1.70-1.66 (2H, m), 1.44 (9H, s).

Step 2

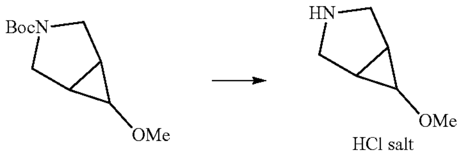 [SMILES: COC1C2CN(C(=O)OC(C)(C)C)CC21 ; COC1C2CNCC21]

HCl salt

HCl (2M in dioxane, 2.3 mL, 4.6 mmol) was added to tert-butyl 6-methoxy-3-azabicyclo[3.1.0]hexane-3-carboxylate (230 mg, 1.08 mmol). The reaction mixture was stirred at 25° C. for 2 h, then concentrated in vacuo to afford 6-methoxy-3-azabicyclo[3.1.0]hexane HCl salt (160 mg, crude) as a light pink solid; $\delta_H$ (400 MHz; DMSO-d6) 9.61 (1H, br d, J 2.8 Hz), 9.31 (1H, br s), 3.33 (1H, s), 3.22 (7H, s), 1.86 (2H, s).

2-(3-Methylazetidin-3-yl)oxazole TFA salt

Step 1

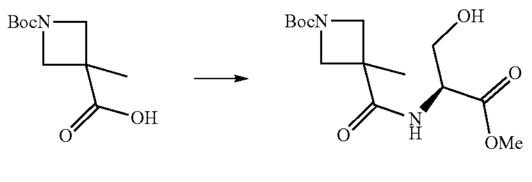 [SMILES: CC(C)(C)OC(=O)N1CC(C)(C(=O)O)C1 ; COC(=O)[C@H](CO)NC(=O)C1(C)CN(C(=O)OC(C)(C)C)C1]

BOP—Cl (12.8 g, 50.2 mmol) was added to a solution of 1-(tert-butoxycarbonyl)-3-methylazetidine-3-carboxylic acid (9.00 g, 41.8 mmol), methyl L-serinate hydrochloride (7.81 g, 50.2 mmol) and triethylamine (17.5 mL, 125 mmol) in dichloromethane (150 mL). The reaction mixture was stirred at 25° C. for 2 h, then diluted with water (30 mL) and extracted into EtOAc (3×30 mL). The combined organic extracts were dried over anhydrous sodium sulfate and then concentrated in vacuo. Purification by flash column chromatography on silica (EtOAc:PE, 0:1 to 1:0) afforded tert-butyl (S)-3-((3-hydroxy-1-methoxy-1-oxopropan-2-yl)carbamoyl)-3-methylazetidine-1-carboxylate (5.30 g, 40%) as a yellow oil; ES-MS [M−$^t$Bu+H]$^+$: 261.0.

Step 2

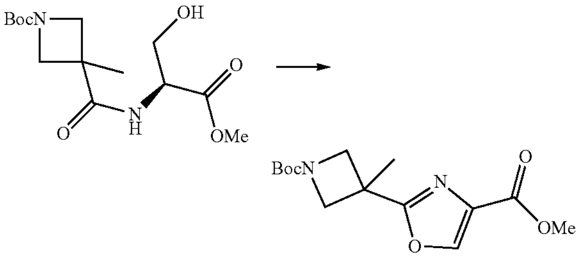

Bis(2-methoxyethyl)aminosulfur trifluoride (2.85 g, 12.9 mmol) was added to a solution of tert-butyl (S)-3-((3-hydroxy-1-methoxy-1-oxopropan-2-yl)carbamoyl)-3-methylazetidine-1-carboxylate (3.70 g, 11.7 mmol) in dichloromethane (70 mL) at −20° C. The reaction mixture was stirred at 0° C. for 4 h, then diluted with water (30 mL) and extracted into EtOAc (3×50 mL). The combined organic extracts were dried over anhydrous sodium sulfate and then concentrated in vacuo. Purification by flash column chromatography on silica (EtOAc:PE, 0:1 to 1:3) afforded methyl 2-(1-(tert-butoxycarbonyl)-3-methylazetidin-3-yl)oxazole-4-carboxylate (1.40 g, 4.72 mmol) as a white solid; $\delta_H$ (400 MHz; $CDCl_3$) 8.21 (1H, s), 4.44-4.33 (2H, m), 3.93 (3H, s), 3.90-3.84 (2H, m), 1.76 (3H, s), 1.45 (9H, s).

Step 3

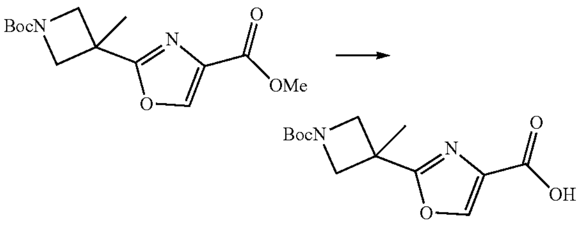

Lithium hydroxide (566 mg, 23.6 mmol) was added to a solution of methyl 2-(1-(tert-butoxycarbonyl)-3-methylazetidin-3-yl)oxazole-4-carboxylate (1.40 g, 4.72 mmol) in THF (15 mL) and water (5 mL). The reaction mixture was stirred at 25° C. for 2 h, then concentrated in vacuo. Water (20 mL) was added and the pH adjusted to ~5 by addition of 1.0 M $HCl_{(aq)}$. The mixture was extracted into EtOAc (3×20 mL) and the combined organic extracts were dried over anhydrous sodium sulfate and then concentrated in vacuo to afford 2-(1-(tert-butoxycarbonyl)-3-methylazetidin-3-yl)oxazole-4-carboxylic acid (1.20 g, 90%) as a white solid; ES-MS [M−$^t$Bu+H]$^+$: 227.1.

Step 4

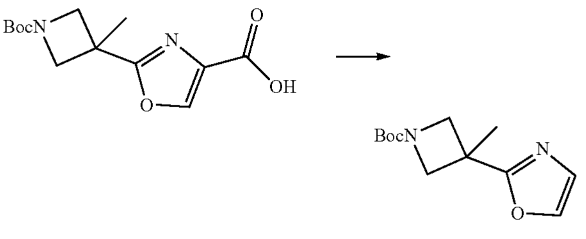

Silver carbonate (488 mg, 1.77 mmol) was added to a solution of 2-(1-(tert-butoxycarbonyl)-3-methylazetidin-3-yl)oxazole-4-carboxylic acid (250 mg, 0.89 mmol) and acetic acid (10 μL, 0.18 mmol) in DMSO (10 mL). The reaction mixture was stirred at 140° C. for 4 h, then filtered and washed with EtOAc. The filtrate was diluted with water (40 mL) and extracted into EtOAc (3×40 mL). The combined organic extracts were washed with brine (2×40 mL), dried over anhydrous sodium sulfate and then concentrated in vacuo. Purification by flash column chromatography on silica (EtOAc:PE, 0:1 to 1:3) afforded tert-butyl 3-methyl-3-(oxazol-2-yl)azetidine-1-carboxylate (70 mg, 29%) as a yellow oil; ES-MS [M−$^t$Bu+H]$^+$: 183.1.

Step 5

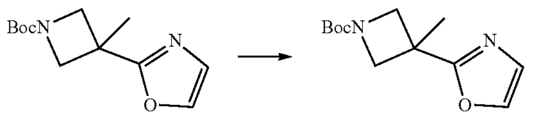

TFA salt

TFA (0.11 mL, 1.47 mmol) was added to a solution of tert-butyl 3-methyl-3-(oxazol-2-yl)azetidine-1-carboxylate (70 mg, 0.29 mmol) in dichloromethane (3 mL). The reaction mixture was stirred at 25° C. for 2 h, then concentrated in vacuo to afford 2-(3-methylazetidin-3-yl)oxazole TFA salt (70 mg, crude).

Benzyl 8-oxa-2,5-diazaspiro[3.5]nonane-5-carboxylate

Step 1

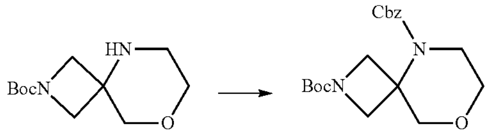 [SMILES: CC(C)(C)OC(=O)N1CC2(COCCN2)C1 ; CC(C)(C)OC(=O)N1CC2(COCCN2C(=O)OCc2ccccc2)C1]

Benzyl chloroformate (329 mg, 1.93 mmol) was added to a solution of tert-butyl 8-oxa-2,5-diazaspiro[3.5]nonane-2-carboxylate (400 mg, 1.75 mmol) and pyridine (0.21 mL, 2.63 mmol) in dichloromethane (5 mL). The reaction mixture was stirred at 20° C. for 2 h, then diluted with water (5 mL) and extracted into EtOAc (2×5 mL). The combined organic extracts were dried over anhydrous sodium sulfate and then concentrated in vacuo. Purification by flash column chromatography on silica (EtOAc:PE, 0:1 to 1:3) afforded 5-benzyl 2-(tert-butyl) 8-oxa-2,5-diazaspiro[3.5]nonane-2,5-dicarboxylate (400 mg, 63%) as a colorless oil; ES-MS $[M+H]^+$: 363.2.

Step 2

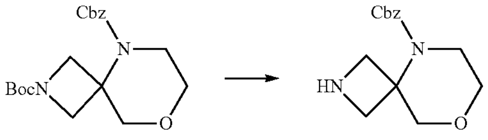 [SMILES: CC(C)(C)OC(=O)N1CC2(COCCN2C(=O)OCc2ccccc2)C1 ; O=C(OCc1ccccc1)N1CCOCC12CNC2]

TFA (1 mL) was added to a solution of 5-benzyl 2-(tert-butyl) 8-oxa-2,5-diazaspiro[3.5]nonane-2,5-dicarboxylate (350 mg, 0.97 mmol) in dichloromethane (2 mL). The reaction mixture was stirred at 20° C. for 2 h, then diluted with saturated aqueous sodium bicarbonate solution (10 mL) and extracted into dichloromethane (2×5 mL). The combined organic extracts were dried over anhydrous sodium sulfate and then concentrated in vacuo to afford benzyl 8-oxa-2,5-diazaspiro[3.5]nonane-5-carboxylate (350 mg, crude) as a colorless oil.

1-(Azetidin-3-yl)ethan-1-one TFA Salt

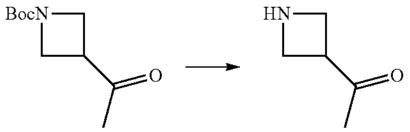

TFA (0.10 mL, 1.35 mmol) was added to a solution of tert-butyl 3-acetylazetidine-1-carboxylate (200 mg, 1.00 mmol) in dichloromethane (0.1 mL). The reaction mixture was stirred at 25° C. for 2 h, then concentrated in vacuo to afford 1-(azetidin-3-yl)ethan-1-one TFA salt (100 mg, crude) as a yellow oil.

1-(4-Chloro-3-((triisopropylsilyl)oxy)phenyl)ethan-1-one

Step 1

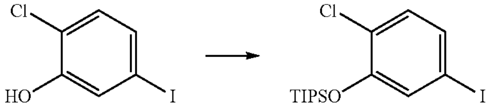

Triisopropylsilyl chloride (9.17 g, 47.6 mmol) was add to a solution of 2-chloro-5-iodophenol (11.0 g, 43.2 mmol) and imidazole (6.47 g, 95.1 mmol) in dichloromethane (10 mL). The reaction mixture was stirred at 25° C. for 3 h, then diluted with water (100 mL) and extracted into EtOAc (3×60 mL). The combined organic extracts were dried over anhydrous sodium sulfate and then concentrated in vacuo. Purification by flash column chromatography on silica (EtOAc: PE, 0:1 to 1:4) afforded (2-chloro-5-iodophenoxy) triisopropylsilane (16.0 g, 90%) as a white solid; $\delta_H$ (400 MHz; DMSO-d6) 7.27-7.21 (1H, m), 7.17-7.11 (2H, m), 1.26-1.14 (3H, m), 0.98 (18H, d, J 7.5 Hz).

Step 2

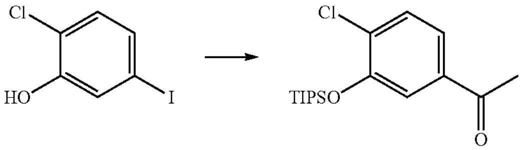

Isopropylmagnesium chloride lithium chloride complex (1.3 M solution in THF) was added to a solution of (2-chloro-5-iodophenoxy)triisopropylsilane (29.0 g, 70.6 mmol) and N-methoxy-N-methylacetamide (8.74 g, 84.7 mmol) in THF (300 mL) at 0° C. The reaction mixture was stirred at this temperature for 5 h, then quenched by addition of saturated aqueous ammonium chloride solution (200 mL). Water (100 mL) was added and the mixture was extracted into EtOAc (3×100 mL). The combined organic extracts were dried over anhydrous sodium sulfate and then concentrated in vacuo. Purification by flash column chromatography on silica (EtOAc:PE, 0:1 to 1:19) afforded 1-(4-chloro-3-((triisopropylsilyl)oxy)phenyl)ethan-1-one (20.2 g, 88%) as a white solid; $\delta_H$ (400 MHz; DMSO-d6) 7.59 (2H, d, J 0.7 Hz), 7.44 (1H, s), 2.55 (3H, s), 1.36-1.26 (3H, m), 1.08 (18H, d, J 7.5 Hz).

Phenyl (5-(1-(4-(oxetan-3-ylcarbamoyl)phenyl) ethyl)thiazol-2-yl)carbamate

Step 1

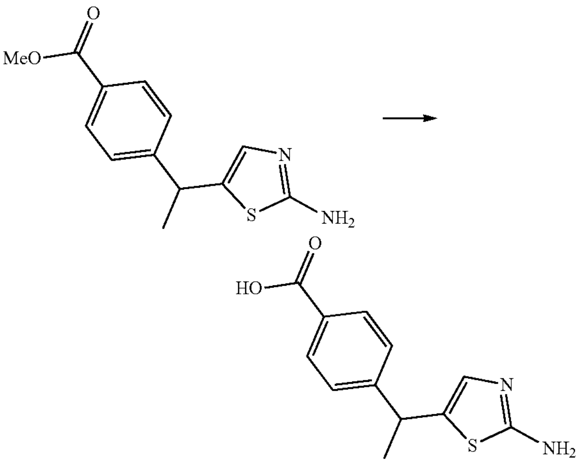

Lithium hydroxide (2.0 M, 3 mL, 6 mmol) was added to a solution of methyl 4-(1-(2-aminothiazol-5-yl)ethyl)benzoate* (1.00 g, 3.81 mmol) in methanol (8 mL) and the resulting mixture was stirred at 20° C. for 12 h. The mixture was adjusted to pH 7 using hydrochloric acid, then diluted with water (50 mL) and extracted into EtOAc (3×100 mL). The combined organic extracts were washed with brine (50 mL), dried over anhydrous sodium sulfate and then concentrated in vacuo to afford 4-(1-(2-aminothiazol-5-yl)ethyl) benzoic acid (1.00 g, crude); ES-MS $[M+H]^+$: 249.1.

*Prepared from methyl 4-acetylbenzoate using procedure C, Steps 1 and 2

Step 2

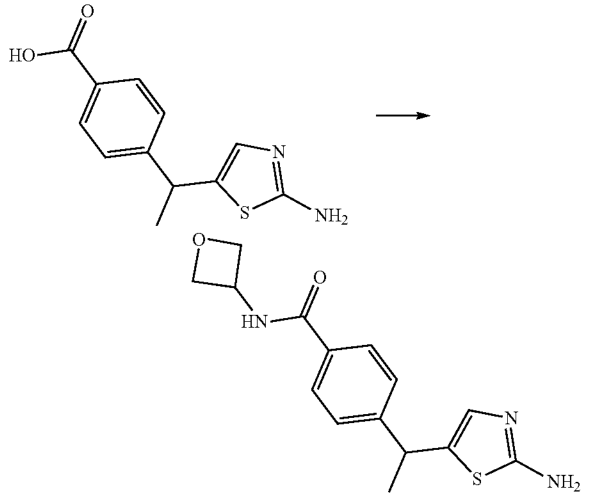

A mixture of 4-(1-(2-aminothiazol-5-yl)ethyl)benzoic acid (0.90 g, 3.62 mmol), oxetan-3-amine (450 mg, 6.16 mmol), HATU (2.07 g, 5.44 mmol) and DIPEA (1.80 mL, 10.3 mmol) in DMF (10 mL) was stirred at 20° C. for 2 h, then concentrated in vacuo and purified by preparative HPLC (column: Welch Ultimate XB_C18, 20-40 m; solvent: acetonitrile:water; gradient: 3:7→1:1) to afford 4-(1-(2-aminothiazol-5-yl)ethyl)-N-(oxetan-3-yl)benzamide (0.70 g, 60%) as a yellow solid; ES-MS $[M+H]^+$: 304.1.

Step 3

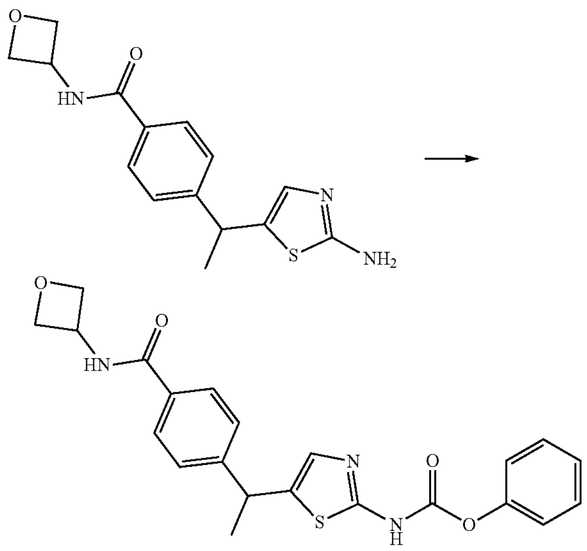

Phenyl (5-(1-(4-(oxetan-3-ylcarbamoyl)phenyl)ethyl)thiazol-2-yl)carbamate was prepared from 4-(1-(2-aminothiazol-5-yl)ethyl)-N-(oxetan-3-yl)benzamide according to procedure C, Step 3; ES-MS $[M+H]^+$: 424.2.

Phenyl (5-(1-(6-(oxetan-3-ylcarbamoyl)pyridin-3-yl) ethyl)thiazol-2-yl)carbamate Step 1

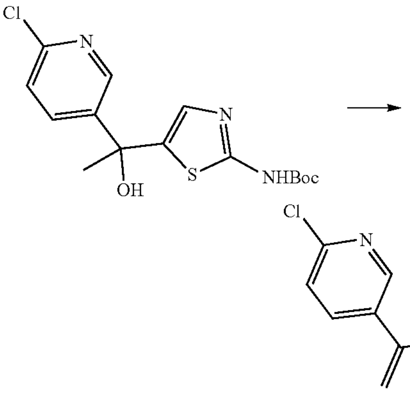

Triethylsilane (18.0 mL, 113 mmol) was added to a solution of tert-butyl (5-(1-(6-chloropyridin-3-yl)-1-hydroxyethyl)thiazol-2-yl)carbamate* (4.0 g, 11.2 mmol) and TFA (8.5 mL, 114 mmol) in DCE (50 mL) and the resulting mixture was stirred at 60° C. for 12 h, then concentrated in vacuo. Water (100 mL) then saturated aqueous sodium bicarbonate solution were added until the pH was ~7. The reaction mixture was extracted into dichloromethane (3×100 mL). The combined organic extracts were dried over anhydrous sodium sulfate and then concentrated in vacuo. Flash column chromatography on silica (EtOAc:PE, 0:1 to 1:1) afforded 5-(1-(6-chloropyridin-3-yl)vinyl)thiazol-2-amine (2.10 g, 75%) as a yellow solid; ES-MS $[M+H]^+$: 238.0.

*Prepared from 1-(6-chloropyridin-3-yl)ethan-1-one using procedure B, Step 1

Step 2

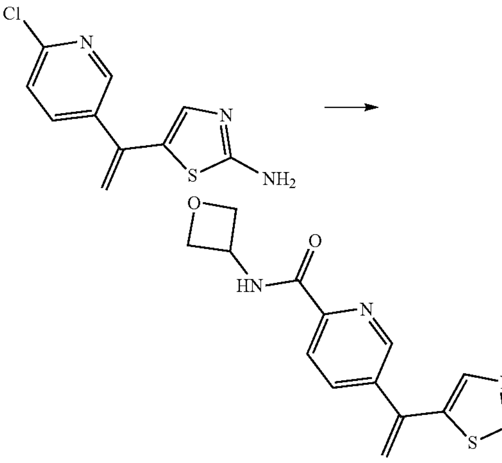

A mixture of 5-(1-(6-chloropyridin-3-yl)vinyl)thiazol-2-amine (2.50 g, 10.5 mmol), oxetan-3-amine (2.50 g, 34.2 mmol), Pd(dppf)$Cl_2$ (1.00 g, 1.37 mmol) and triethylamine (5.00 mL, 35.9 mmol) in DMF was stirred under carbon monoxide at 80° C. for 12 h. The reaction mixture was diluted with brine (150 mL), extracted into EtOAc (3×150 mL), dried over anhydrous sodium sulfate and then concentrated in vacuo. Purification by preparative HPLC (column: Welch Ultimate XB_C18, 20-40 m; solvent: acetonitrile: water; gradient: 3:7→1:1) afforded 5-(1-(2-aminothiazol-5-yl)vinyl)-N-(oxetan-3-yl)picolinamide (0.80 g, 18%) as a yellow solid; ES-MS $[M+H]^+$: 303.2.

Steps 3 and 4

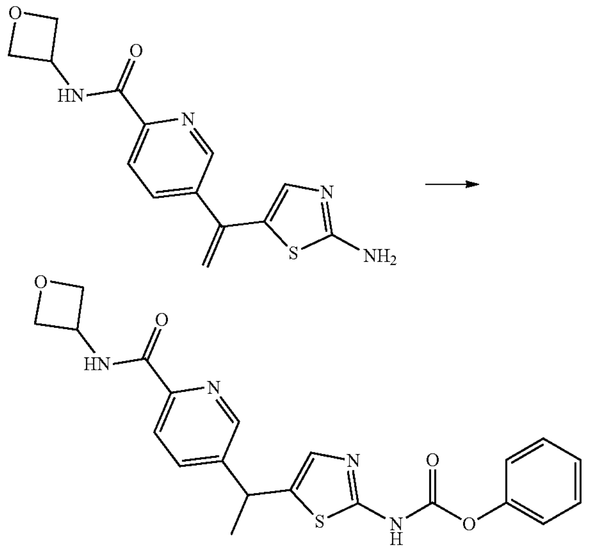

Phenyl (5-(1-(6-(oxetan-3-ylcarbamoyl)pyridin-3-yl)ethyl)thiazol-2-yl)carbamate was prepared from 5-(1-(2-aminothiazol-5-yl)vinyl)-N-(oxetan-3-yl)picolinamide according to procedure A, Steps 3 and 4; ES-MS $[M+H]^+$: 425.1.

3-(4-(1-(2-Aminothiazol-5-yl)ethyl)phenyl)oxetan-3-ol

Step 1

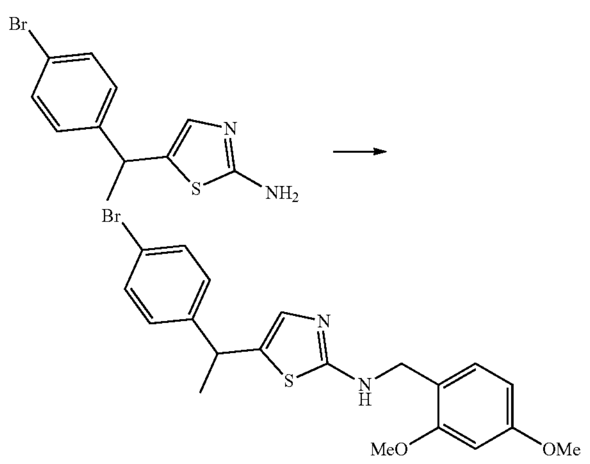

2,4-Dimethoxybenzaldehyde (2.30 g, 13.8 mmol) and acetic acid (1 mL, 17.5 mmol) were added to a solution of 5-(1-(4-bromophenyl)ethyl)thiazol-2-amine* (1.00 g, 3.53 mmol) in methanol (10 mL) at 0° C. The reaction mixture was stirred at this temperature for 30 min, then sodium cyanoborohydride (450 mg, 7.16 mmol) was added and stirring was continued at 25° C. for another 12 h. The mixture was diluted with water (20 mL) and extracted into EtOAc (3×20 mL). The combined organic extracts were dried over anhydrous sodium sulfate and then concentrated in vacuo. Flash column chromatography on silica (EtOAc: PE, 2:3 to 1:1) afforded 5-(1-(4-bromophenyl)ethyl)-N-(2,4-dimethoxybenzyl)thiazol-2-amine (800 mg, 51%) as a yellow oil; ES-MS $[M+H]^+$: 435.0.

*Prepared from 1-(4-bromophenyl)ethan-1-one using procedure C, steps 1 and 2

Step 2

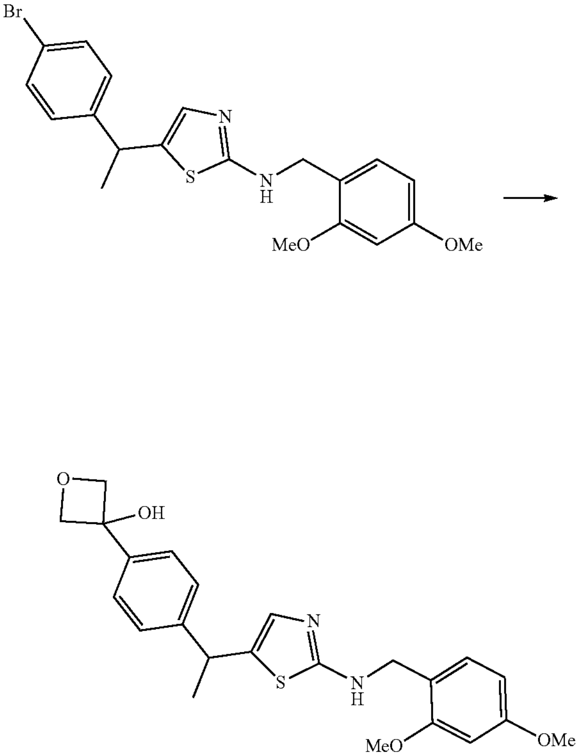

n-BuLi (2.5 M in THF, 1.00 mL, 2.50 mmol) was added dropwise to a solution of 5-(1-(4-bromophenyl)ethyl)-N-(2,4-dimethoxybenzyl)thiazol-2-amine (200 mg, 0.46 mmol) in THF (3 mL) at −60° C. and the resulting mixture was stirred at this temperature for 1 h. A solution of oxetan-3-one (70 mg, 0.97 mmol) in THF (2 mL) was added and stirring was continued at −60° C. for 1 h. The reaction mixture was quenched with saturated aqueous ammonium chloride solution (20 mL) and extracted into EtOAc (3×50 mL). The combined organic extracts were dried over anhydrous sodium sulfate and then concentrated in vacuo. Flash column chromatography on silica (EtOAc:PE, 9:1 to 1:0) afforded 3-(4-(1-(2-((2,4-dimethoxybenzyl)amino)thiazol-5-yl)ethyl)phenyl)oxetan-3-ol (85 mg, 43%) as a yellow oil; ES-MS $[M+H]^+$: 427.2.

Step 3

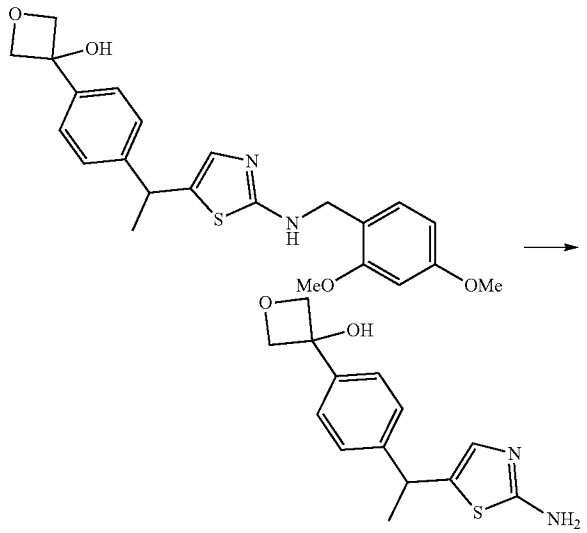

A solution of 3-(4-(1-(2-((2,4-dimethoxybenzyl)amino)thiazol-5-yl)ethyl)phenyl)oxetan-3-ol (85, 0.20 mmol) in TFA (1 mL) was stirred at 25° C. for 12 h. Saturated aqueous sodium bicarbonate solution (20 mL) was added and the mixture was extracted into EtOAc (2×20 mL). The combined organic extracts were dried over anhydrous sodium sulfate and then concentrated in vacuo to afford 3-(4-(1-(2-aminothiazol-5-yl)ethyl)phenyl)oxetan-3-ol (50 mg, crude); ES-MS $[M+H]^+$: 277.2.

Synthetic Procedure A

Example 1: Oxazol-2-ylmethyl (R)-(5-(1-(6-methoxypyridin-3-yl)ethyl)thiazol-2-yl)carbamate Example 2: Oxazol-2-ylmethyl (S)-(5-(1-(6-methoxypyridin-3-yl)ethyl)thiazol-2-yl)carbamate Step 1

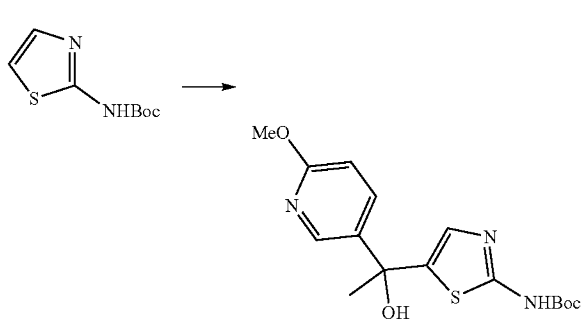

LDA (1.0 M in THF, 494.4 mL, 494 mmol) was added to a solution of tert-butyl thiazol-2-ylcarbamate (45.0 g, 225 mmol) in THF (900 mL) at −20° C. and stirred for 30 min at this temperature. A solution of 1-(6-methoxypyridin-3-yl)ethan-1-one (40.8 g, 270 mmol) in THF (800 mL) was added slowly and stirring was continued at −20° C. for 1 h. The reaction mixture was quenched by addition of saturated aqueous ammonium chloride solution (500 mL) at 0° C. Water was added (500 mL) and the mixture was extracted into EtOAc (3×300 mL). The combined organic extracts were washed with brine (500 mL), dried over anhydrous sodium sulfate and concentrated in vacuo. Flash column chromatography on silica (EtOAc:PE, 0:1 to 1:0) afforded tert-butyl (5-(1-hydroxy-1-(6-methoxypyridin-3-yl)ethyl)thiazol-2-yl)carbamate (55.0 g, 69%) as a white solid; ES-MS $[M+H]^+$: 352.1.

Step 2

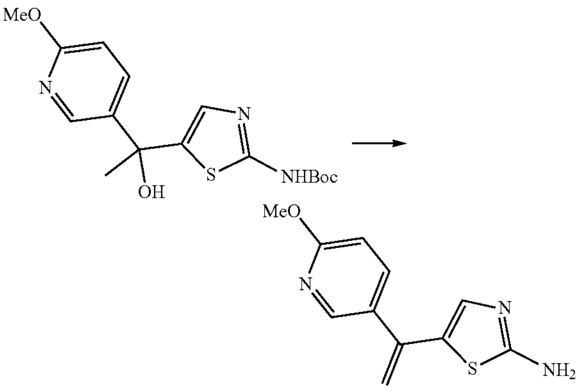

TFA (150 mL, 2.02 mol) was added to a solution of tert-butyl (5-(1-hydroxy-1-(6-methoxypyridin-3-yl)ethyl)thiazol-2-yl)carbamate (55.0 g, 157 mmol) in DCE (450 mL) and the resulting mixture was stirred at 80° C. for 6 h. Saturated aqueous sodium carbonate solution was then slowly added until the pH was ~8. Water (500 mL) was added and the mixture was extracted into EtOAc (3×1 L). The combined organic extracts were washed with brine (3 L), dried over anhydrous sodium sulfate and concentrated in vacuo. Trituration with EtOAc afforded tert-butyl (5-(1-(6-methoxypyridin-3-yl)vinyl)thiazol-2-yl)carbamate (36.0 g, 99%) as a white solid; ES-MS $[M+H]^+$: 234.0.

Step 3

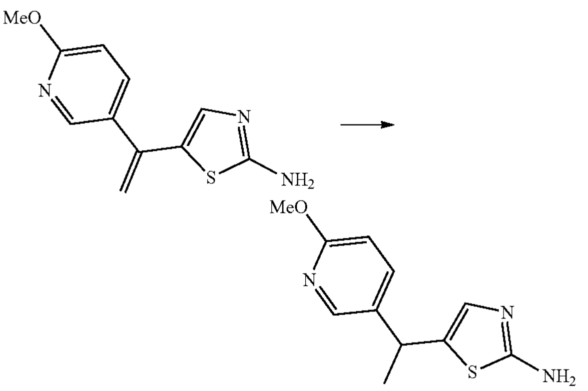

10% $Pd(OH)_2/C$ (3.20 g) was added to a solution of 5-(1-(6-methoxypyridin-3-yl)vinyl)thiazol-2-amine (32.0 g, 137 mmol) in methanol (600 mL). The resulting mixture was stirred under hydrogen (50 PSI) at 70° C. for 24 h, filtered through a pad of Celite eluting with methanol (30 mL), then concentrated in vacuo. Flash column chromatography on silica (EtOAc:PE, 0:1 to 7:3) afforded 5-(1-(6-methoxypyridin-3-yl)ethyl)thiazol-2-amine (12.5 g, 38%) as a yellow solid; ES-MS $[M+H]^+$: 236.1.

Step 4

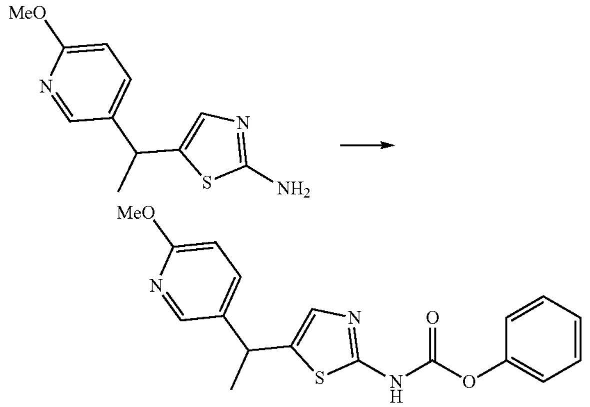

Phenyl chloroformate (7.44 mL, 58.4 mmol) was added to a solution of 5-(1-(6-methoxypyridin-3-yl)ethyl)thiazol-2-amine (12.5 g, 53.1 mmol) and pyridine (6.43 mL, 79.7 mmol) in THF (120 mL) at 0° C. The resulting mixture was stirred at 20° C. for 1 h, then concentrated in vacuo. Trituration with acetonitrile:water (1:2) afforded phenyl (5-(1-(6-methoxypyridin-3-yl)ethyl)thiazol-2-yl)carbamate (17.0 g, 90%) as a white solid; ES-MS $[M+H]^+$: 356.1.

Step 5

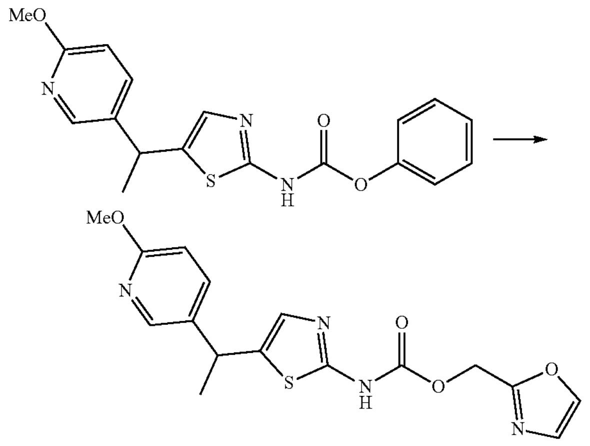

Sodium hydride (60% dispersion in oil, 3.83 g, 95.7 mmol) was added to a solution of oxazol-2-ylmethanol (9.48 g, 95.7 mmol) in THF (170 mL) at 0° C. The resulting mixture was stirred 0° C. for 30 min and then a solution of phenyl (5-(1-(6-methoxypyridin-3-yl)ethyl)thiazol-2-yl)carbamate (17.0 g, 47.8 mmol) in THF (100 mL) was added. The reaction mixture was stirred at 20° C. for 12 h, then poured into saturated aqueous ammonium chloride solution (50 mL). The mixture was extracted into EtOAc (3×100 mL) and the combined organic extracts were dried over anhydrous sodium sulfate and then concentrated in vacuo. Trituration with EtOAc afforded oxazol-2-ylmethyl (5-(1-(6-methoxypyridin-3-yl)ethyl)thiazol-2-yl)carbamate (14.7 g, 85%) as a white solid; ES-MS $[M+H]^+$: 361.1.

Step 6

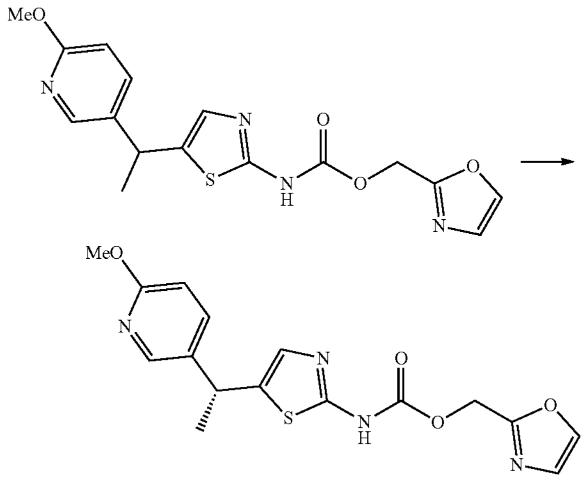

Example 1

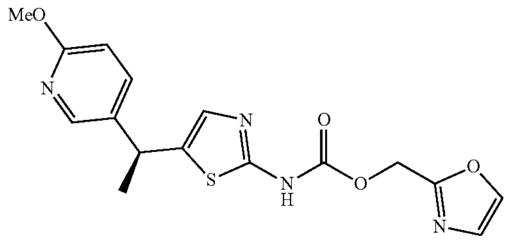

Example 2

Oxazol-2-ylmethyl (5-(1-(6-methoxypyridin-3-yl)ethyl)thiazol-2-yl)carbamate (14.7 g) was purified by preparative SFC (column: CHIRALCEL® OX-10/SFC 50×250 mm, 10 micron; $CO_2$:EtOH (0.1% $NH_4OH$) 60:40) to afford oxazol-2-ylmethyl (R)-(5-(1-(6-methoxypyridin-3-yl)ethyl)thiazol-2-yl)carbamate (6.17 g, 42%, Example 1) as a white solid; $\delta_H$ (400 MHz; DMSO-d6) 11.89 (1H, br s), 8.15 (1H, s), 8.10 (1H, d, J 2.4 Hz), 7.59 (1H, m), 7.25 (1H, s), 7.16 (1H, s), 6.77 (1H, d, J 8.4 Hz), 5.27 (2H, s), 4.31 (1H, m), 3.82 (3H, s), 1.59 (3H, d, J 6.8 Hz); ES-MS $[M+H]^+$: 361.1; $[\alpha]_D^{20}$−27.2 (c 0.47, DMSO) and oxazol-2-ylmethyl (S)-(5-(1-(6-methoxypyridin-3-yl)ethyl)thiazol-2-yl)carbamate (6.50 g, 44%, Example 2) as a white solid; $\delta_H$ (400 MHz; DMSO-d6) 11.89 (1H, br s), 8.15 (1H, s), 8.10 (1H, d, J 2.4 Hz), 7.59 (1H, m), 7.25 (1H, s), 7.16 (1H, s), 6.77 (1H, d, J 8.4 Hz), 5.27 (2H, s), 4.31 (1H, m), 3.82 (3H, s), 1.59 (3H, d, J 6.8 Hz); ES-MS $[M+H]^+$: 361.1; $[\alpha]_D^{20}$+27.1 (c 0.48, DMSO). The absolute stereochemistry of Example 1 was verified by X-ray crystallography.

Other examples prepared using synthetic procedure A are shown in the following table. All intermediates are commercially available unless noted (see 'Intermediate synthesis' section).

| Ex. No. | Name | Structure | Intermediates requiring synthesis | ES-MS [M + H]$^+$ | $[\alpha]_D^{20}$ |
|---|---|---|---|---|---|
| 3 | oxazol-2-ylmethyl (R)-(5-(1-(6-(difluoromethoxy) pyridin-3-yl)ethyl) thiazol-2-yl)carbamate | 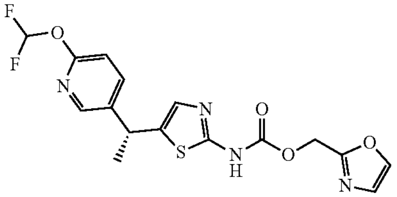 [SMILES: C[C@H](c1ccc(OC(F)F)nc1)c1cnc(NC(=O)OCc2ncco2)s1] | n/a | 397.1 | −23.1 (c 0.31, DMSO) |
| 4 | oxazol-2-ylmethyl (S)-(5-(1-(6-(trifluoromethoxy) pyridin-3-yl)ethyl) thiazol-2-yl)carbamate | 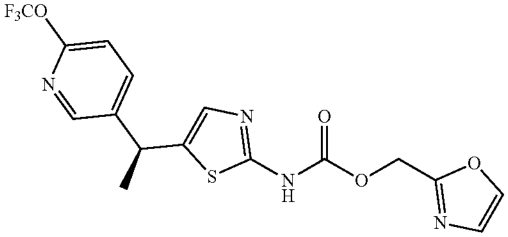 [SMILES: C[C@@H](c1ccc(OC(F)(F)F)nc1)c1cnc(NC(=O)OCc2ncco2)s1] | 1-(6-(trifluoromethoxy) pyridin-3-yl) ethan-1-one | 415.1 | +19.1 (c 0.33, DMSO) |
| 5 | oxazol-2-ylmethyl (R)-(5-(1-(6-(trifluoromethoxy) pyridin-3-yl)ethyl) thiazol-2-yl)carbamate | 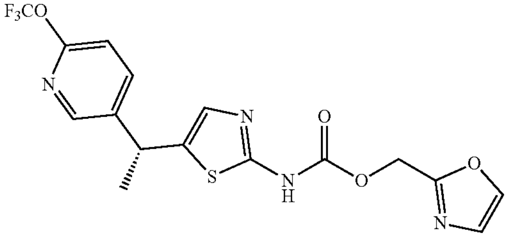 [SMILES: C[C@H](c1ccc(OC(F)(F)F)nc1)c1cnc(NC(=O)OCc2ncco2)s1] | 1-(6-(trifluoromethoxy) pyridin-3-yl) ethan-1-one | 415.1 | −19.2 (c 0.33, DMSO) |
| 6 | oxazol-2-ylmethyl (S)-(5-(1-(6-(methoxy-d3)pyridin-3-yl)ethyl) thiazol-2-yl)carbamate | 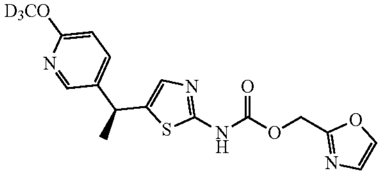 | 1-(6-(methoxy-d3)pyridin-3-yl)ethan-1-one | 364.1 | +28.9 (c 0.33, DMSO) |
| 7 | oxazol-2-ylmethyl (R)-(5-(1-(6-(methoxy-d3)pyridin-3-yl)ethyl) thiazol-2-yl)carbamate | 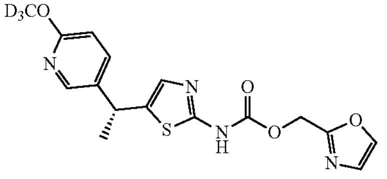 | 1-(6-(methoxy-d3)pyridin-3-yl)ethan-1-one | 364.1 | −30.1 (c 0.33, DMSO) |

Alternative, asymmetric synthesis of Example 1: Oxazol-2-ylmethyl (R)-(5-(1-(6-methoxypyridin-3-yl)ethyl)thiazol-2-yl)carbamate Step 1

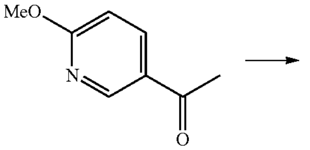

-continued

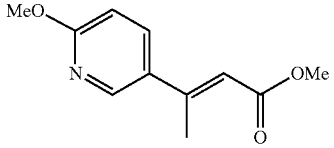

A mixture of potassium tert-butoxide (222 g, 1.98 mol) and methyl 2-(diethoxyphosphoryl)acetate (417 g, 1.98 mol) in THF (3 L) was stirred at 25° C. for 1 h. 1-(6-methoxy-pyridin-3-yl)ethan-1-one (150 g, 992 mmol) was then added and stirring was continued at 25° C. for an additional 12 h. Water (2 L) was added and the mixture was extracted into MTBE (3×1 L). The combined organic extracts were dried over anhydrous sodium sulfate and then concentrated in vacuo to afford methyl (E)-3-(6-methoxypyridin-3-yl)but-2-enoate (200 g, 55%) as a yellow solid; ES-MS [M+H]$^+$: 208.1.

Step 2

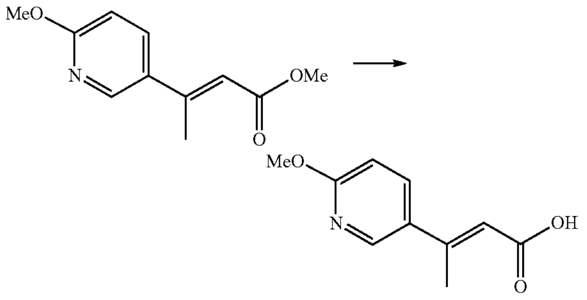

Sodium hydroxide (138 mg, 3.47 mol) was added to a solution of methyl (E)-3-(6-methoxypyridin-3-yl)but-2-enoate (240 g, 1.16 mol) in water (1.25 L) and ethanol (1.25 L). The reaction mixture was stirred at 25° C. for 12 h then concentrated in vacuo to remove ethanol and extracted into MTBE (3×1 L). The aqueous phase was separated and $HCl_{(aq)}$ (2.0 M) was added to adjust the pH to 5-6. The precipitate was filtered, then triturated with MTBE (1.25 mL, 25° C., 12 h) to afford (E)-3-(6-methoxypyridin-3-yl)but-2-enoic acid (95.0 g, 42%) as a white solid; $\delta_H$ (400 MHz; DMSO-d6) 8.38 (1H, d, J 2.40 Hz), 7.93 (1H, dd, J 8.6, 2.6 Hz), 6.84 (1H, d, J 8.6 Hz), 6.12 (1H, d, J 1.2 Hz), 3.88 (3H, s), 2.47 (3H, s).

Step 3

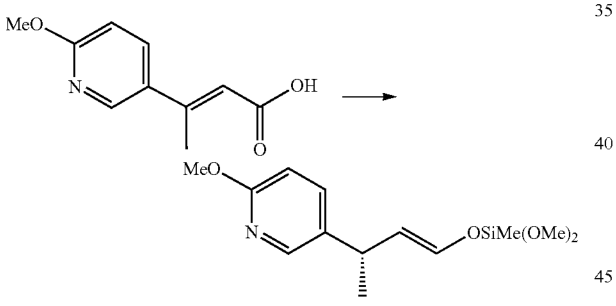

Methyldimethoxysilane (286 g, 2.69 mol) was added to a mixture of copper(II) acetate (1.30 g, 7.16 mmol), 1,2-bis((2R,5R)-2,5-diphenylphospholan-1-yl)ethane (3.90 g, 7.70 mmol) and (E)-3-(6-methoxypyridin-3-yl)but-2-enoic acid (130 g, 672 mmol) in toluene (1.5 L). The resulting mixture was stirred at 40° C. for 16 h, then concentrated in vacuo to afford (S,E)-5-(4-((dimethoxy(methyl)silyl)oxy)but-3-en-2-yl)-2-methoxypyridine (190 g, crude) as a yellow oil; ES-MS $[M+H]^+$: 284.3.

Step 4

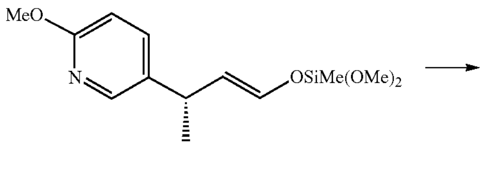

-continued

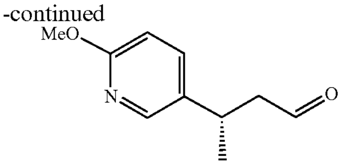

Water (200 mL) and ammonium fluoride (74.5 g, 2.01 mol) were added to a solution of (S,E)-5-(4-((dimethoxy(methyl)silyl)oxy)but-3-en-2-yl)-2-methoxypyridine (190 g, 670 mmol) in THF (1.8 L) at 0° C. The mixture was stirred at 0-10° C. for 1 h, then diluted with water (1 L) and extracted into EtOAc (2×1 L). The combined organic extracts were dried over anhydrous sodium sulfate and then concentrated in vacuo. Flash column chromatography on silica (EtOAc:PE, 1:15 to 1:5) afforded (S)-3-(6-methoxypyridin-3-yl)butanal (90.3 g, 74%) as a yellow oil; ES-MS $[M+H]^+$: 180.3.

Step 5

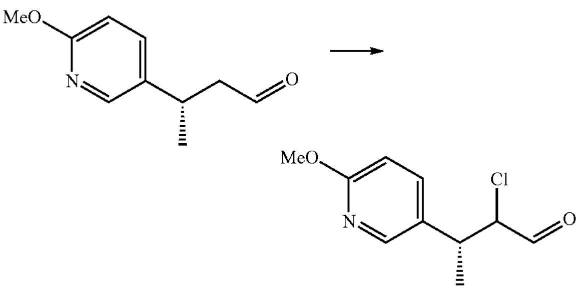

NCS (116 g, 870 mmol) was added to a solution of (S)-3-(6-methoxypyridin-3-yl)butanal (130 g, 725 mmol) and DL-proline (16.7 g, 145 mmol) in dichloromethane (1.3 L) at 0° C. The mixture was stirred at 25° C. for 4 h, then diluted with water (1 L) and extracted into dichloromethane (2×1 L). The combined organic extracts were dried over anhydrous sodium sulfate and then concentrated in vacuo. Flash column chromatography on silica (EtOAc:PE, 1:10 to 1:1) afforded (3R)-2-chloro-3-(6-methoxypyridin-3-yl)butanal (120 g, 77%) as a yellow oil; ES-MS $[M+H]^+$: 214.2.

Step 6

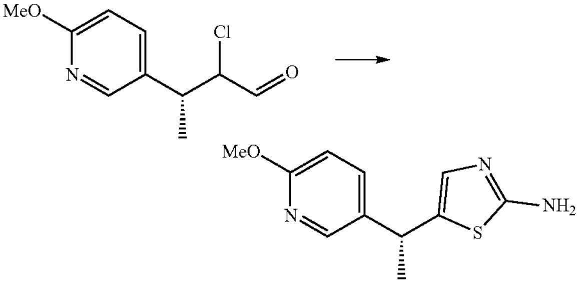

Thiourea (85.5 g, 1.12 mol) was added to a solution of (3R)-2-chloro-3-(6-methoxypyridin-3-yl)butanal (120 g, 561 mmol) in ethanol (1.2 L). The reaction mixture was stirred at 85° C. for 12 h, then cooled to 25° C., adjusted to pH ~8 with ammonium hydroxide, filtered and concentrated in vacuo. Water (1 L) was added and the mixture was extracted into EtOAc (2×2 L). The combined organic extracts were dried over anhydrous sodium sulfate and then concentrated in vacuo. Flash column chromatography on silica (EtOAc:PE, 1:10 to 1:1) afforded (R)-5-(1-(6-methoxypyridin-3-yl)ethyl)thiazol-2-amine (56.0 g, 40%) as a yellow solid; ES-MS $[M+H]^+$: 236.2.

Step 7

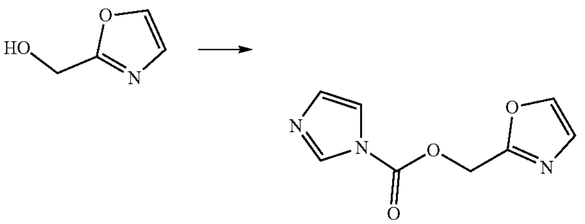

CDI (54.0 g, 333 mmol) was added in portions to a solution of oxazol-2-ylmethanol (30.0 g, 302 mmol) in THF (300 mL) at 0° C. The reaction mixture was stirred at 25° C. for 2 h, then diluted with water (500 mL) and extracted into (EtOAc (2×500 mL). The combined organic extracts were dried over anhydrous sodium sulfate and then concentrated in vacuo to afford oxazol-2-ylmethyl 1H-imidazole-1-carboxylate (58.0 g, crude) as a yellow oil.

Step 8

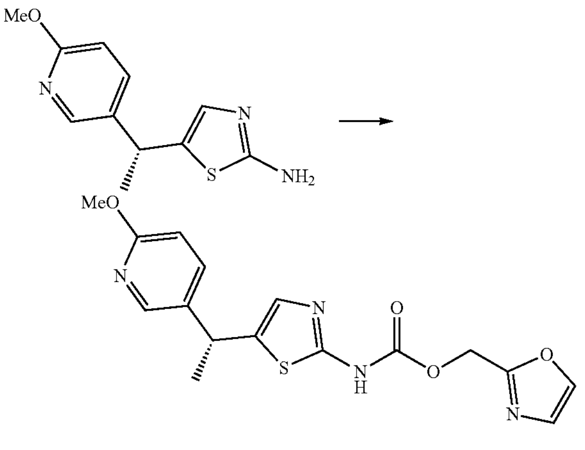

Cesium carbonate (283 g, 869 mmol) was added to a solution of (R)-5-(1-(6-methoxypyridin-3-yl)ethyl)thiazol-2-amine (47.0 g, 199 mmol) and oxazol-2-ylmethyl 1H-imidazole-1-carboxylate (Step 7, 56.0 g, 289 mmol) in DMF (500 mL). The reaction mixture was stirred at 40° C. for 3 h, then cooled to 25° C., diluted with water (1 L) and extracted into dichloromethane (2×500 mL). The combined organic extracts were dried over anhydrous sodium sulfate and then concentrated in vacuo. Trituration with MTBE (200 mL, 25° C., 2 h) and purification by preparative SFC (column: CHIRALPAK® AD 30×250 mm, 10 micron; Phase A: CO2, Phase B: 1:1 acetonitrile:[EtOH (0.1% ammonium hydroxide)]; Isocratic elution: B:A 60:40) afforded oxazol-2-ylmethyl (R)-(5-(1-(6-methoxypyridin-3-yl)ethyl)thiazol-2-yl)carbamate (39.0 g, 37%) as a white solid; $\delta_H$ (400 MHz; DMSO-d6) 11.89 (1H, br s), 8.15 (1H, s), 8.10 (1H, d, J 2.4 Hz), 7.59 (1H, m), 7.25 (1H, s), 7.16 (1H, s), 6.77 (1H, d, J 8.4 Hz), 5.27 (2H, s), 4.31 (1H, m), 3.82 (3H, s), 1.59 (3H, d, J 6.8 Hz); $[\alpha]_D^{20}$–29.4 (c 0.52, DMSO).

Synthetic Procedure B

Example 8: Oxazol-2-ylmethyl (R)-(5-(1-(6-isopropoxypyridin-3-yl)ethyl)thiazol-2-yl)carbamate Example 9: Oxazol-2-ylmethyl (S)-(5-(1-(6-isopropoxypyridin-3-yl)ethyl)thiazol-2-yl)carbamate Step 1

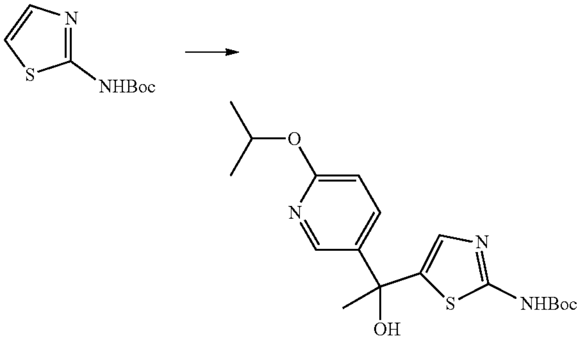

n-BuLi (2.5 M in THF, 11.0 mL, 27.5 mmol) was added dropwise to a solution of tert-butyl thiazol-2-ylcarbamate (2.50 g, 12.5 mmol) in THF (20 mL) at −60° C. and the resulting mixture was stirred at this temperature for 1 h. A solution of 1-(6-isopropoxypyridin-3-yl)ethan-1-one (2.24 g, 12.5 mmol) in THF (10 mL) was added and stirring was continued at −60° C. for 2 h. The reaction mixture was quenched with saturated aqueous ammonium chloride solution (50 mL) and extracted into EtOAc (3×50 mL). The combined organic extracts were dried over anhydrous sodium sulfate and then concentrated in vacuo. Flash column chromatography on silica (EtOAc:PE, 0:1 to 2:3) afforded tert-butyl (5-(1-hydroxy-1-(6-isopropoxypyridin-3-yl)ethyl)thiazol-2-yl)carbamate (2.00 g, 40%) as a white solid; ES-MS $[M+H]^+$: 380.2.

Step 2

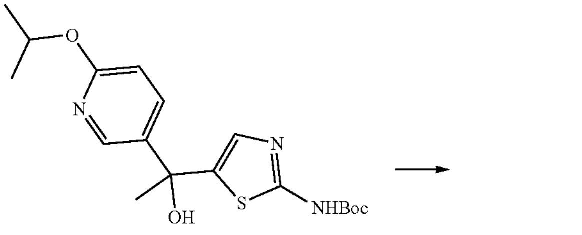

-continued

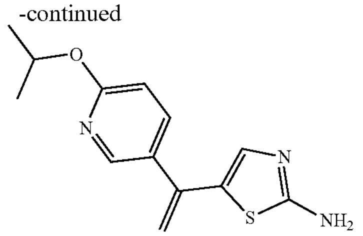

TFA (7 mL, 94.2 mmol) was added to a solution of tert-butyl (5-(1-hydroxy-1-(6-isopropoxypyridin-3-yl)ethyl)thiazol-2-yl)carbamate (2.00 g, 5.27 mmol) in DCE (20 mL) and the resulting mixture was stirred at 80° C. for 2 h. Water (50 mL) then solid sodium carbonate were added until the pH was ~8. The mixture was extracted into EtOAc (3×60 mL). The combined organic extracts were washed with brine (2×100 mL), dried over anhydrous sodium sulfate and concentrated in vacuo. Flash column chromatography on silica (EtOAc:PE, 0:1 to 2:3) afforded 5-(1-(6-isopropoxypyridin-3-yl)vinyl)thiazol-2-amine (1.20 g, 86%) as a white solid; ES-MS $[M+H]^+$: 262.2.

Step 3

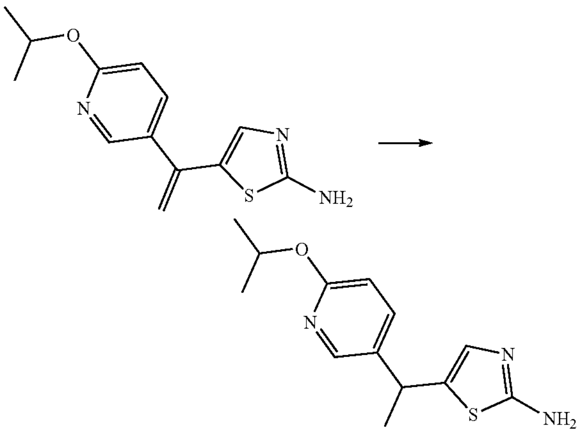

10% Pd/C (200 mg) was added to a solution of 5-(1-(6-isopropoxypyridin-3-yl)vinyl)thiazol-2-amine (1.00 g, 3.83 mmol) in methanol (20 mL) and the resulting mixture was stirred under hydrogen (50 PSI) at 60° C. for 12 h. The mixture was filtered through celite and concentrated in vacuo to afford 5-(1-(6-isopropoxypyridin-3-yl)ethyl)thiazol-2-amine (300 mg, 29%) as a white solid; ES-MS $[M+H]^+$: 264.2.

Step 4

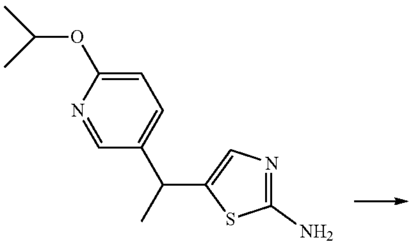

-continued

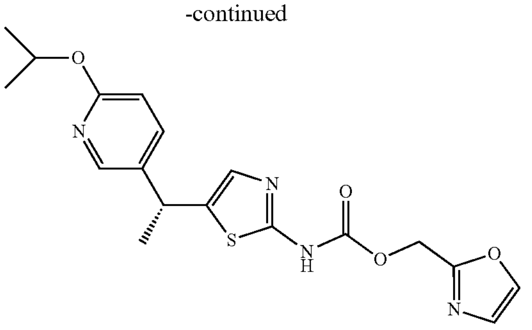

Example 8

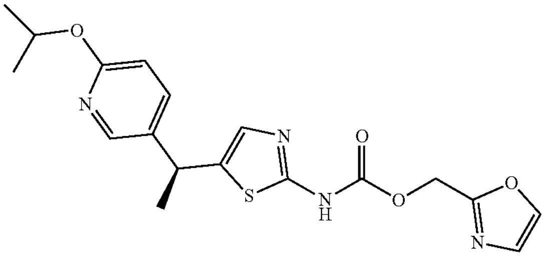

Example 9

CDI (924 mg, 5.70 mmol) was added to a solution of oxazol-2-ylmethanol (564 mg, 5.70 mmol) in THF (10 mL) and the resulting mixture was stirred at 60° C. for 4 h. The mixture was then transferred to a solution of 5-(1-(6-isopropoxypyridin-3-yl)ethyl)thiazol-2-amine (300 mg, 1.14 mmol), triethylamine (0.79 mL, 5.70 mmol) and DMAP (28 mg, 0.23 mmol) in THF (5 mL) at 20° C. and stirred at 60° C. for 12 h. Water (30 mL) was added and the mixture was extracted into EtOAc (3×30 mL). The combined organic extracts were washed with brine (2×20 mL), dried over anhydrous sodium sulfate and then concentrated in vacuo. Trituration with methanol and further purification by preparative SFC (column: CHIRALPAK® IG-10/SFC 50×250 mm, 10 micron; $CO_2$:[1/1 acetonitrile/isopropanol (0.1% $NH_{40}H$)]60:40 afforded oxazol-2-ylmethyl (R)-(5-(1-(6-isopropoxypyridin-3-yl)ethyl)thiazol-2-yl)carbamate (46 mg, 17%, Example 8) as a white solid; $\delta_H$ (400 MHz; DMSO-d6) 11.90 (1H, br s), 8.15 (1H, d, J 0.9 Hz), 8.07 (1H, d, J=2.4 Hz), 7.56 (1H, m), 7.25 (1H, d, J 0.7 Hz), 7.16 (1H, d, J 1.0 Hz), 6.68 (1H, d, J 8.7 Hz), 5.27 (2H, s), 5.20 (1H, m), 4.29 (1H, m), 1.58 (3H, d, J 7.1 Hz), 1.26 (6H, d, J 6.1 Hz); ES-MS $[M+H]^+$: 389.2; $[\alpha]_D^{20}$−25.3 (c 0.28, DMSO) and oxazol-2-ylmethyl (S)-(5-(1-(6-isopropoxypyridin-3-yl)ethyl)thiazol-2-yl)carbamate (68 mg, 25%, Example 9) as a white solid; $\delta_H$ (400 MHz; DMSO-d6) 11.90 (1H, br s), 8.15 (1H, d, J 0.9 Hz), 8.07 (1H, d, J=2.4 Hz), 7.56 (1H, m), 7.25 (1H, d, J 0.7 Hz), 7.16 (1H, d, J 1.0 Hz), 6.68 (1H, d, J 8.7 Hz), 5.27 (2H, s), 5.20 (1H, m), 4.29 (1H, m), 1.58 (3H, d, J 7.1 Hz), 1.26 (6H, d, J 6.1 Hz); ES-MS $[M+H]^+$: 389.2; $[\alpha]_D^{20}$+26.0 (c 0.38, DMSO).

Other examples prepared using synthetic procedure B are shown in the following table. All intermediates are commercially available unless noted (see 'Intermediate synthesis' section).

| Ex. No. | Name | Structure | Intermediates requiring synthesis | ES-MS $[M + H]^+$ | Chiral SFC analytical method* and retention time |
|---|---|---|---|---|---|
| 10 | oxazol-2-ylmethyl (R)-(5-(1-(2-methoxypyrimidin-5-yl)ethyl)thiazol-2-yl)carbamate | 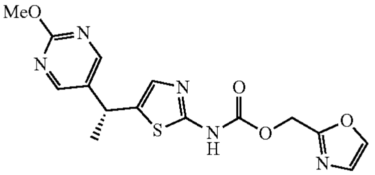 [SMILES: COc1ncc([C@@H](C)c2cnc(NC(=O)OCc3ncco3)s2)cn1] | n/a | 362.1 | Column: Lux 3 μm Cellulose-2, LC Column 250 × 4.6 mm; Phase A: $CO_2$, Phase B: EtOH (0.05% DEA); Gradient elution: B:A from 30% to 60% RT 1.50 min |
| 11 | oxazol-2-ylmethyl (R)-(5-(1-(6-methoxy-5-(trifluoromethyl) pyridin-3-yl)ethyl) thiazol-2-yl) carbamate | 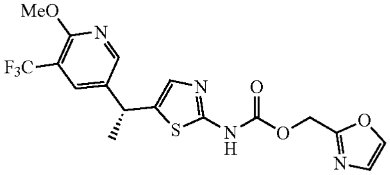 [SMILES: COc1ncc([C@@H](C)c2cnc(NC(=O)OCc3ncco3)s2)cc1C(F)(F)F] | 1-(6-methoxy-5-(trifluoromethyl) pyridin-3-yl) ethan-1-one | 429.1 | Column: CHIRALPAK® IG-3 4.6 × 50 mm, 3 micron; Phase A: $CO_2$, Phase B: EtOH (0.05% DEA); Gradient elution: B:A from 20% to 60% RT 1.34 min |
| 12 | oxazol-2-ylmethyl (S)-(5-(1-(6-methoxy-5-(trifluoromethyl) pyridin-3-yl)ethyl) thiazol-2-yl) carbamate | 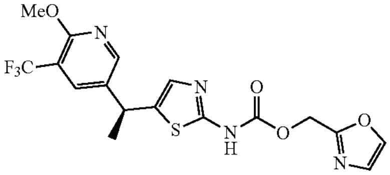 [SMILES: COc1ncc([C@H](C)c2cnc(NC(=O)OCc3ncco3)s2)cc1C(F)(F)F] | 1-(6-methoxy-5-(trifluoromethyl) pyridin-3-yl) ethan-1-one | 429.1 | Column: CHIRALPAK® IG-3 4.6 × 50 mm, 3 micron; Phase A: $CO_2$, Phase B: EtOH (0.05% DEA); Gradient elution: B:A from 20% to 60% RT 1.67 min |
| 13 | oxazol-2-ylmethyl (R)-(5-(1-(6-ethoxypyridin-3-yl)ethyl) thiazol-2-yl)carbamate | 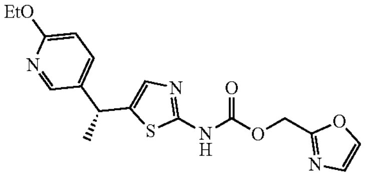 [SMILES: CCOc1ccc([C@@H](C)c2cnc(NC(=O)OCc3ncco3)s2)cn1] | n/a | 375.1 | Column: CHIRALPAK® IG-3 4.6 × 50 mm, 3 micron; Phase A: $CO_2$, Phase B: IPA/[MeCN (0.05% DEA)] 50/50; Isocratic elution: B:A 50:50 RT 0.89 min |
| 14 | oxazol-2-ylmethyl (S)-(5-(1-(6-ethoxypyridin-3-yl)ethyl) thiazol-2-yl)carbamate | 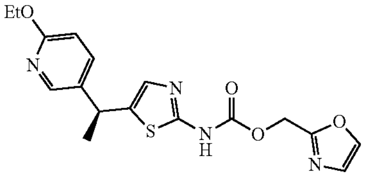 [SMILES: CCOc1ccc([C@H](C)c2cnc(NC(=O)OCc3ncco3)s2)cn1] | n/a | 375.0 | Column: CHIRALPAK® IG-3 4.6 × 50 mm, 3 micron; Phase A: $CO_2$, Phase B: IPA/[MeCN (0.05% DEA)] 50/50; Isocratic elution: B:A 50:50 RT 1.58 min |
| 15 | oxazol-2-ylmethyl (R)-(5-(1-(6-methoxy-2-methylpyridin-3-yl)ethyl) thiazol-2-yl)carbamate | 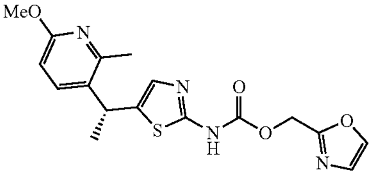 [SMILES: COc1ccc([C@@H](C)c2cnc(NC(=O)OCc3ncco3)s2)c(C)n1] | n/a | 375.1 | Column: CHIRALPAK® IG-3 4.6 × 50 mm, 3 micron; Phase A: $CO_2$, Phase B: EtOH (0.05% DEA)]; Isocratic elution: B:A 50:50 RT 0.92 min |

-continued

| Ex. No. | Name | Structure | Intermediates requiring synthesis | ES-MS [M + H]+ | Chiral SFC analytical method* and retention time |
|---|---|---|---|---|---|
| 16 | oxazol-2-ylmethyl (S)-(5-(1-(6-methoxy-2-methylpyridin-3-yl)ethyl)thiazol-2-yl)carbamate | 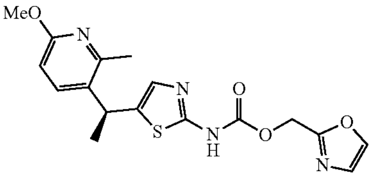 [SMILES: COc1ccc([C@H](C)c2cnc(NC(=O)OCc3ncco3)s2)c(C)n1] | | 375.2 | Column: CHIRALPAK ® IG-3 4.6 x 50 mm, 3 micron; Phase A: $CO_2$, Phase B: EtOH (0.05% DEA)]; Isocratic elution: B:A 50:50 RT 1.77 min |
| 17 | oxazol-2-ylmethyl (R)-(5-(1-(6-methoxy-4-methylpyridin-3-yl)ethyl)thiazol-2-yl)carbamate | 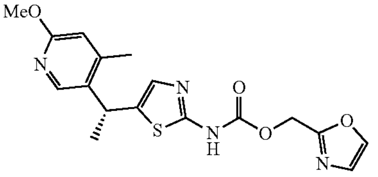 [SMILES: COc1cc(C)c([C@@H](C)c2cnc(NC(=O)OCc3ncco3)s2)cn1] | 1-(6-methoxy-4-methylpyridin-3-yl)ethan-1-one | 375.1 | Column: CHIRALPAK ® AD-3 4.6 x 50 mm, 3 micron; Phase A: $CO_2$, Phase B: EtOH (0.05% DEA)]; Isocratic elution: B:A 50:50 RT 0.77 min |
| 18 | oxazol-2-ylmethyl (S)-(5-(1-(6-methoxy-4-methylpyridin-3-yl)ethyl)thiazol-2-yl)carbamate | 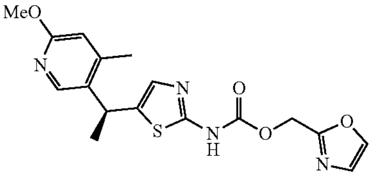 [SMILES: COc1cc(C)c([C@H](C)c2cnc(NC(=O)OCc3ncco3)s2)cn1] | 1-(6-methoxy-4-methylpyridin-3-yl)ethan-1-one | 375.1 | Column: CHIRALPAK ® AD-3 4.6 x 50 mm, 3 micron; Phase A: $CO_2$, Phase B: EtOH (0.05% DEA)]; Isocratic elution: B:A 50:50 RT 1.52 min |
| 19 | oxazol-2-ylmethyl (5-(6-chloro-2,3-dihydro-benzofuran-3-yl)thiazol-2-yl)carbamate | 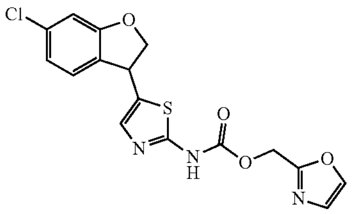 [SMILES: O=C(Nc1ncc(C2COc3cc(Cl)ccc32)s1)OCc1ncco1] alternate reduction conditions used: Mg (5 eq), MeOH, 0 to 25° C., 16 h | n/a | 378.0 | n/a |

*Flow rate: 3 mL/min; Detector: PDA; Column temperature: 35° C.; Back pressure: 100 Bar

Synthetic Procedure C

Example 20: Oxazol-2-ylmethyl (R)-(5-(1-(4-chlorophenyl)ethyl)thiazol-2-yl)carbamate

Example 21: Oxazol-2-ylmethyl (S)-(5-(1-(4-chlorophenyl)ethyl)thiazol-2-yl)carbamate Step 1

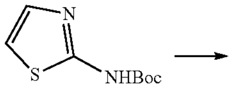

-continued

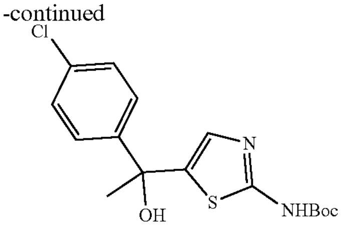

n-BuLi (2.5 M in THF, 49.9 mL, 125 mmol) was added dropwise to a solution of tert-butyl thiazol-2-ylcarbamate (2.50 g, 12.5 mmol) in THF (20 mL) at −60° C. and the resulting mixture was stirred at this temperature for 30 min. A solution of 1-(4-chlorophenyl)ethan-1-one (9.71 mL, 74.9 mmol) in THF (100 mL) was added and stirring was continued at −60° C. for 4 h. The reaction mixture was quenched with saturated aqueous ammonium chloride solution (200 mL) and extracted into EtOAc (3×200 mL). The combined organic extracts were dried over anhydrous sodium sulfate and then concentrated in vacuo. Flash column chromatography on silica (EtOAc:PE, 0:1 to 3:7) afforded tert-butyl (5-(1-(4-chlorophenyl)-1-hydroxyethyl) thiazol-2-yl)carbamate (30.6 g, 86%) as a white solid; ES-MS $[M+H]^+$: 355.0.

Step 2

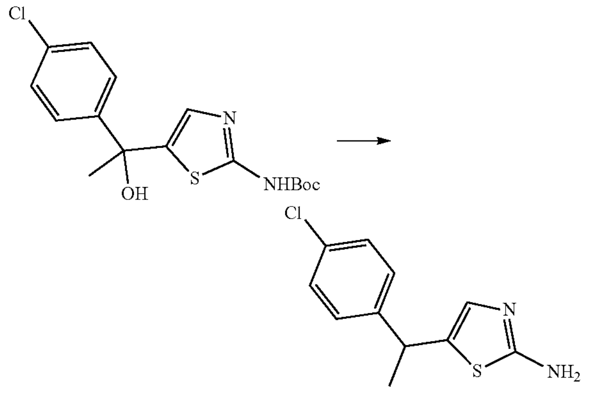

Triethylsilane (54.0 mL, 338 mmol) was added to a solution of tert-butyl (5-(1-(4-chlorophenyl)-1-hydroxy-ethyl)thiazol-2-yl)carbamate (30.0 g, 84.5 mmol) in TFA (200 mL) and the resulting mixture was stirred at 60° C. for 2 h, then concentrated in vacuo. Water (100 mL) then saturated aqueous sodium bicarbonate solution were added until the pH was ~7. The reaction mixture was extracted into EtOAc (3×100 mL). The combined organic extracts were dried over anhydrous sodium sulfate and then concentrated in vacuo. Flash column chromatography on silica (EtOAc: PE, 0:1 to 7:3) afforded 5-(1-(4-chlorophenyl)ethyl)thiazol-2-amine (10.6 g, 52%) as a white solid; ES-MS $[M+H]^+$: 238.9.

Step 3

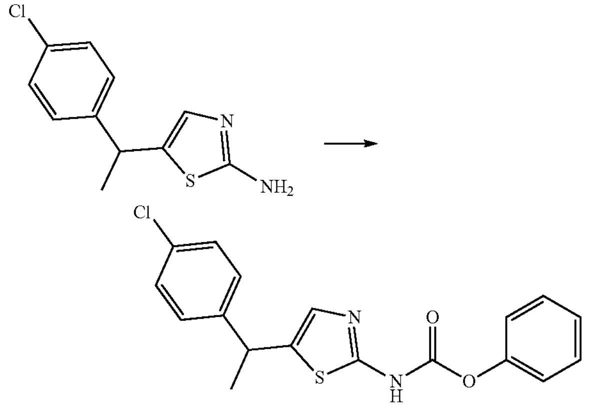

A solution of phenyl chloroformate (1.58 mL, 12.6 mmol) in THF (2 mL) was added to a solution of 5-(1-(4-chloro-phenyl)ethyl)thiazol-2-amine (2.00 g, 8.38 mmol) and pyridine (2.03 mL, 25.1 mmol) in THF (20 mL) at 0° C. The resulting mixture was stirred at 25° C. for 2 h. Water (20 mL) was added and the mixture was extracted into EtOAc (3×20 mL). The combined organic extracts were washed with brine (20 mL), dried over anhydrous sodium sulfate and then concentrated in vacuo. Trituration with EtOAc:water 9:1 afforded phenyl (5-(1-(4-chlorophenyl)ethyl)thiazol-2-yl) carbamate (2.70 g, 7.52 mmol) as an off-white solid; ES-MS $[M+H]^+$: 359.1.

Step 4

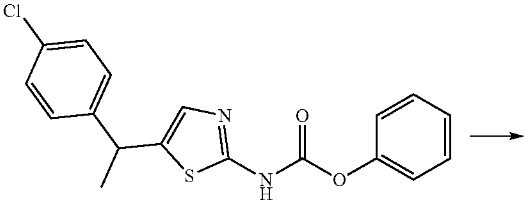

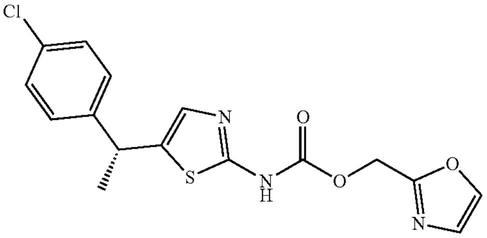

Example 20

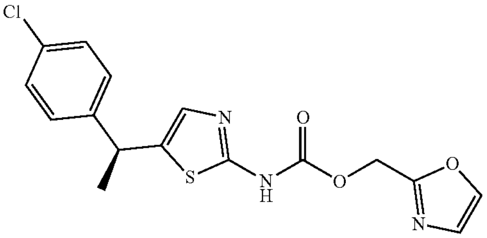

Example 21

Sodium hydride (60% dispersion in oil, 134 mg, 3.34 mmol) was added to a solution of oxazol-2-ylmethanol (414 mg, 4.18 mmol) in THF (10 mL) at 0° C. The resulting mixture was stirred 0° C. for 30 min and then phenyl (5-(1-(4-chlorophenyl)ethyl)thiazol-2-yl)carbamate (1.00 g, 2.79 mmol) was added. The reaction mixture was stirred at 0° C. for 3 h, then poured into saturated aqueous ammonium chloride solution (50 mL). The mixture was extracted into EtOAc (3×100 mL) and the combined organic extracts were dried over anhydrous sodium sulfate and then concentrated in vacuo. Flash column chromatography on silica (EtOAc: PE, 0:1 to 4:1), followed by purification by preparative HPLC (column: Waters™ XBridge BEH C18 OBD Prep Column, 130A, 10 μm, 50 mm×150 mm; acetonitrile:[water (0.1% ammonium carbonate)]; gradient: 35:65→65:35), followed by further purification by preparative SFC (column: CHIRALPAK® IG-10/SFC 50×250 mm, 10 micron; $CO_2$: isopropanol (0.1% $NH_4OH$) 40:60) afforded oxazol-2-ylmethyl (R)-(5-(1-(4-chlorophenyl)ethyl)thiazol-2-yl)carbamate (170 mg, 17% Example 20) as an off-white solid; $\delta_H$ (400 MHz; DMSO-d6) 12.12-11.66 (1H, m), 8.15 (1H, s), 7.39-7.35 (2H, m), 7.33-7.29 (2H, m), 7.25 (1H, s), 7.17 (1H, s), 5.27 (2H, s), 4.36-4.31 (1H, m), 1.58 (3H, d, J 7.20 Hz); ES-MS $[M+H]^+$: 364.1; $[\alpha]_D^{20}$−2.87 (c 0.25, acetonitrile) and oxazol-2-ylmethyl (S)-(5-(1-(4-chlorophenyl)ethyl)thiazol-2-yl)carbamate (173 mg, 17%, Example 21) as an off-white solid; $\delta_H$ (400 MHz; DMSO-d6) 12.12-11.66 (1H, m), 8.15 (1H, s), 7.39-7.35 (2H, m), 7.33-7.29 (2H, m), 7.25 (1H, s), 7.17 (1H, s), 5.27 (2H, s), 4.36-4.31 (1H, m), 1.58 (3H, d, J 7.20 Hz); ES-MS $[M+H]^+$: 364.1; $[\alpha]_D^{20}$+2.41 (c 0.25, acetonitrile). The absolute stereochemistry of Example 20 was verified by X-ray crystallography.

Other examples prepared using synthetic procedure C are shown in the following table. All intermediates are commercially available unless noted (see 'Intermediate synthesis' section).

| Ex. No. | Name | Structure | Intermediates requiring synthesis | ES-MS $[M + H]^+$ | Chiral SFC analytical method* and retention time |
|---|---|---|---|---|---|
| 22 | 3-methoxybenzyl (5-(1-(4-chlorophenyl) ethyl)thiazol-2-yl)carbamate | 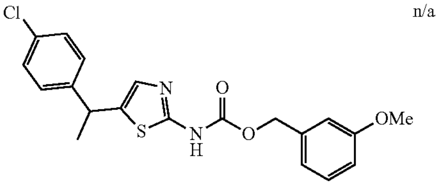 | n/a | 403.1 | n/a |
| 23 | (4-methyloxazol-2-yl)methyl (5-(1-(4-chlorophenyl) ethyl)thiazol-2-yl)carbamate | 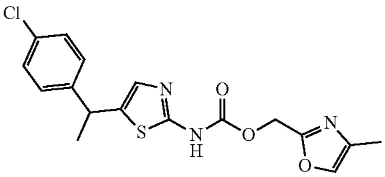 [SMILES: Cc1coc(COC(=O)Nc2ncc(C(C)c3ccc(Cl)cc3)s2)n1] | n/a | 378.1 | n/a |
| 24 | (4-(trifluoromethyl) oxazol-2-yl)methyl (5-(1-(4-chlorophenyl) ethyl)thiazol-2-yl)carbamate | 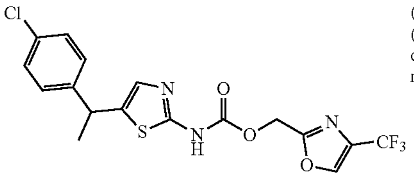 | (4-(trifluoromethyl) oxazol-2-yl) methanol | 432.0 | n/a |
| 20 | oxazol-2-ylmethyl (R)-(5-(1-(4-chlorophenyl) ethyl)thiazol-2-yl)carbamate | 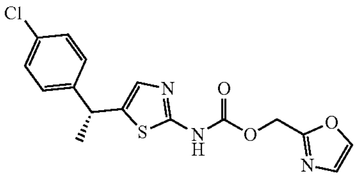 [SMILES: C[C@H](c1ccc(Cl)cc1)c1cnc(NC(=O)OCc2ncco2)s1] | n/a | 364.0 | Column: CHIRALPAK ® IG-3 4.6 x 50 mm, 3 micron; Phase A: $CO_2$, Phase B: IPA/[MeCN (0.05% DEA)] 50/50; Isocratic elution: B:A 40:60 RT 0.94 min |

-continued

| Ex. No. | Name | Structure | Intermediates requiring synthesis | ES-MS [M + H]+ | Chiral SFC analytical method* and retention time |
|---|---|---|---|---|---|
| 21 | oxazol-2-ylmethyl (S)-(5-(1-(4-chlorophenyl) ethyl)thiazol-2-yl)carbamate | 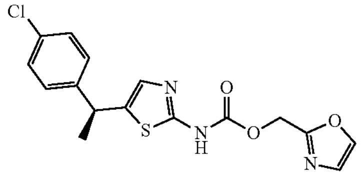 [SMILES: C[C@@H](c1ccc(Cl)cc1)c1cnc(NC(=O)OCc2ncco2)s1] | n/a | 364.0 | Column: CHIRALPAK ® IG-3 4.6 × 50 mm, 3 micron; Phase A: $CO_2$, Phase B: IPA/[MeCN (0.05% DEA)] 50/50; Isocratic elution: B:A 40:60 RT 1.54 min |
| 25 | 1-benzyl-3-(5-(1-(4-chlorophenyl) ethyl)thiazol-2-yl)urea | 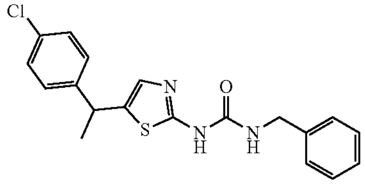 [SMILES: CC(c1ccc(Cl)cc1)c1cnc(NC(=O)NCc2ccccc2)s1] | n/a | 372.1 | n/a |
| 26 | 1-(oxazol-2-yl)propyl (5-(1-(4-chlorophenyl) ethyl)thiazol-2-yl)carbamate | 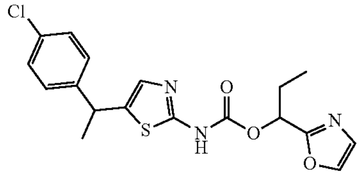 [SMILES: CCC(OC(=O)Nc1ncc(C(C)c2ccc(Cl)cc2)s1)c1ncco1] | 1-(oxazol-2-yl)propan-1-ol | 392.0 | n/a |
| 27 | (2H-1,2,3-triazol-2-yl)methyl (5-(1-(4-chlorophenyl) ethyl)thiazol-2-yl)carbamate | 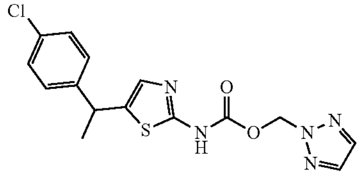 [SMILES: CC(c1ccc(Cl)cc1)c1cnc(NC(=O)OCn2nccn2)s1] | n/a | 364.1 | n/a |
| 28 | (1H-pyrazol-1-yl)methyl (5-(1-(4-chlorophenyl) ethyl)thiazol-2-yl)carbamate | 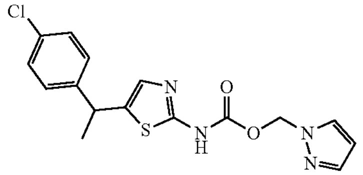 [SMILES: CC(c1ccc(Cl)cc1)c1cnc(NC(=O)OCn2cccn2)s1] | n/a | 363.1 | n/a |
| 29 | (3-methyl-1,2,4-oxadiazol-5-yl)methyl (5-(1-(4-chlorophenyl) ethyl)thiazol-2-yl)carbamate | 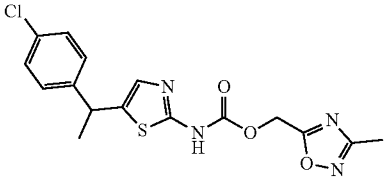 [SMILES: Cc1noc(COC(=O)Nc2ncc(C(C)c3ccc(Cl)cc3)s2)n1] | n/a | 379.1 | n/a |

-continued

| Ex. No. | Name | Structure | Intermediates requiring synthesis | ES-MS [M + H]$^+$ | Chiral SFC analytical method* and retention time |
|---|---|---|---|---|---|
| 30 | oxazol-2-ylmethyl (R)-(5-(1-(5-methoxypyridin-2-yl)ethyl)thiazol-2-yl)carbamate | 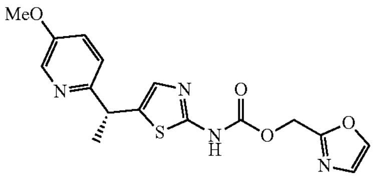 [SMILES: COc1ccc([C@@H](C)c2cnc(NC(=O)OCc3ncco3)s2)nc1] | n/a | 361.1 | Column: CHIRALCEL ® OX-3 4.6 × 50 mm, 3 micron; Phase A: $CO_2$, Phase B: EtOH (0.05% DEA); Isocratic elution: B:A 40:60 RT 1.32 min |
| 31 | oxazol-2-ylmethyl (R)-(5-(1-(5-chloropyrazin-2-yl)ethyl) thiazol-2-yl)carbamate | 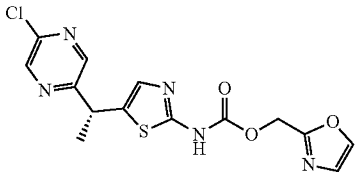 [SMILES: C[C@H](c1cnc(Cl)cn1)c1cnc(NC(=O)OCc2ncco2)s1] Step 2 furnished the dihydrothiazole: (E)-5-(1-(5-chloropyrazin-2-yl)ethylidene)-4,5-dihydrothiazol-2-amine. An additional isomerization step was used to provide the terminal thiazole: DBU (2 eq), $CH_2Cl_2$, 25° C., 16 h | n/a | 366.1 | Column: CHIRALCEL ® OX-3 4.6 × 50 mm, 3 micron; Phase A: $CO_2$, Phase B: EtOH (0.05% DEA); Isocratic elution: B:A 40:60 RT 1.27 min |
| 32 | (1H-pyrazol-5-yl)methyl (5-(1-(4-chlorophenyl) ethyl)thiazol-2-yl)carbamate | 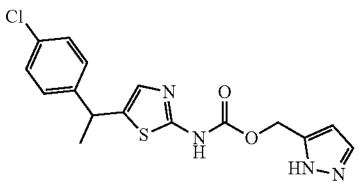 [SMILES: CC(c1ccc(Cl)cc1)c1cnc(NC(=O)OCc2ccn[nH]2)s1] Step 4 used THP-protected starting material: (1-(tetrahydro-2H-pyran-2-yl)-1H-pyrazol-5-yl)methanol. A subsequent THP-removal step provided the final compound: 4M HCl in dioxane, $CH_2Cl_2$, 25° C. 1 h | n/a | 363.0 | n/a |

-continued

| Ex. No. | Name | Structure | Intermediates requiring synthesis | ES-MS [M + H]+ | Chiral SFC analytical method* and retention time |
|---|---|---|---|---|---|
| 33 | (1H-1,2,4-triazol-3-yl)methyl (5-(1-(4-chlorophenyl) ethyl)thiazol-2-yl)carbamate | 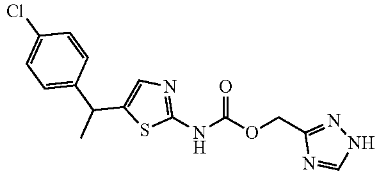 [SMILES: CC(c1ccc(Cl)cc1)c1cnc(NC(=O)OCc2nc[nH]n2)s1] Step 4 used SEM-protected starting material: (1-((2-(trimethylsilyl)ethoxy)methyl)-1H-1,2,4-triazol-3-yl)methanol. A subsequent SEM-removal step provided the final compound: TFA, $CH_2Cl_2$, 25° C. | (1-((2-(trimethylsilyl) ethoxy)methyl)-1H-1,2,4-triazol-3-yl)methanol | 364.1 | n/a |

*Flow rate: 3 mL/min; Detector: PDA; Column temperature: 35° C.; Back pressure: 100 Bar

Synthetic Procedure D

Example 34: Pyridin-2-ylmethyl (5-(1-(4-chlorophenyl)ethyl)thiazol-2-yl)carbamate

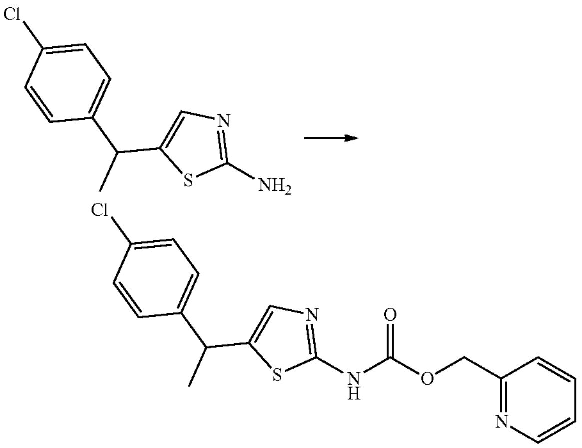

CDI (17.0 g, 105 mmol) was added to a solution of 2-pyridylmethanol (11.4 g, 105 mmol) in THF (50 mL) and the resulting mixture was stirred at 60° C. for 6 h. The mixture was then transferred to a solution of 5-(1-(4-chlorophenyl)ethyl)thiazol-2-amine* (5 g, 20.94 mmol), triethylamine (14.6 mL, 105 mmol) and DMAP (256 mg, 2.09 mmol) in THF (50 mL) at 25° C. and stirred at 60° C. for 12 h. Water (50 mL) was added and the mixture was extracted into EtOAc (3×60 mL). The combined organic extracts were washed with brine (2×100 mL), dried over anhydrous sodium sulfate and then concentrated in vacuo. Purification by preparative HPLC (column: Welch Ultimate XB-$SiO_2$, 10 μm, 50×250 mm; hexane:ethanol; gradient: 99:1→85:15) afforded pyridin-2-ylmethyl (5-(1-(4-chlorophenyl)ethyl) thiazol-2-yl)carbamate (7.77 g, 48%) as a white solid; $\delta_H$ (400 MHz; DMSO-d6) 11.79 (1H, s), 8.54 (1H, m), 7.82 (1H, s), 7.42-7.28 (6H, m), 7.17 (1H, s), 5.24 (2H, s), 4.33 (1H, m), 1.57 (3H, s); ES-MS $[M+H]^+$: 374.0.

*Prepared according to Synthetic Procedure C, Steps 1 and 2

Other examples prepared using synthetic procedure D are shown in the following table. All intermediates are commercially available unless noted (see 'Intermediate synthesis' section).

| Ex. No. | Name | Structure | Intermediates requiring synthesis | ES-MS [M + H]+ |
|---|---|---|---|---|
| 35 | oxazol-2-ylmethyl (5-(2-(dimethylamino) benzyl)thiazol-2-yl)carbamate | 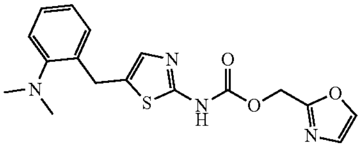 [SMILES: CN(C)c1ccccc1Cc1cnc(NC(=O)OCc2ncco2)s1] | n/a | 359.1 |

-continued

| Ex. No. | Name | Structure | Intermediates requiring synthesis | ES-MS [M + H]+ |
|---|---|---|---|---|
| 36 | oxazol-2-ylmethyl (5-(2-(pyrrolidin-1-yl)benzyl)thiazol-2-yl)carbamate | 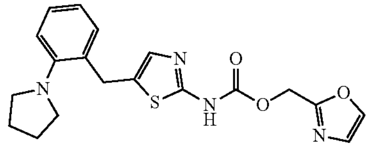 [SMILES: O=C(Nc1ncc(Cc2ccccc2N2CCCC2)s1)OCc1ncco1] | n/a | 385.2 |
| 37 | oxazol-2-ylmethyl (5-(2-morpholinobenzyl) thiazol-2-yl)carbamate | 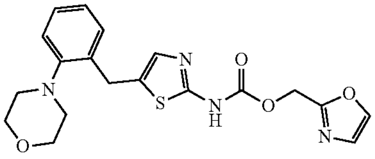 [SMILES: O=C(Nc1ncc(Cc2ccccc2N2CCOCC2)s1)OCc1ncco1] | n/a | 401.1 |
| 38 | 2-fluorobenzyl (5-(1-(4-chlorophenyl) ethyl)thiazol-2-yl)carbamate | 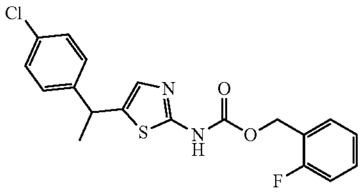 [SMILES: CC(c1ccc(Cl)cc1)c1cnc(NC(=O)OCc2ccccc2F)s1] | n/a | 391.0 |
| 39 | (3-fluoropyridin-2-yl)methyl (5-(1-(4-chlorophenyl) ethyl)thiazol-2-yl)carbamate | 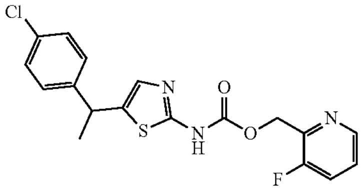 [SMILES: CC(c1ccc(Cl)cc1)c1cnc(NC(=O)OCc2ncccc2F)s1] | n/a | 392.1 |
| 40 | oxazol-2-ylmethyl (5-(1-(4-chloro-3-cyanophenyl) ethyl)thiazol-2-yl)carbamate | 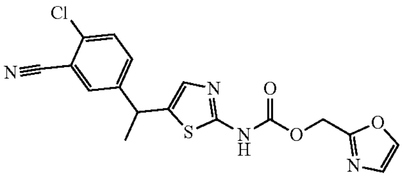 [SMILES: CC(c1ccc(Cl)c(C#N)c1)c1cnc(NC(=O)OCc2ncco2)s1] | n/a | 389.0 |
| 41 | oxazol-2-ylmethyl (5-(1-(4-chlorophenyl)-2,2-difluoroethyl) thiazol-2-yl)carbamate | 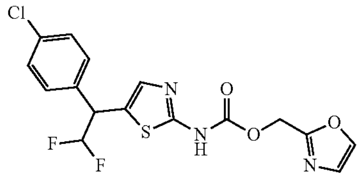 [SMILES: O=C(Nc1ncc(C(c2ccc(Cl)cc2)C(F)F)s1)OCc1ncco1] | n/a | 400.0 |
| 42 | oxazol-2-ylmethyl (5-(1-(4-chlorophenyl)-2-fluoroethyl) thiazol-2-yl)carbamate | 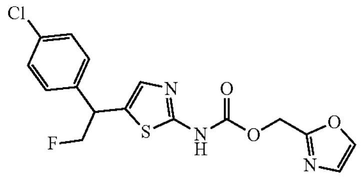 [SMILES: O=C(Nc1ncc(C(CF)c2ccc(Cl)cc2)s1)OCc1ncco1] | n/a | 382.0 |
| 43 | oxazol-2-ylmethyl (5-(1-(4-(trifluoromethyl) phenyl) ethyl)thiazol-2-yl)carbamate | 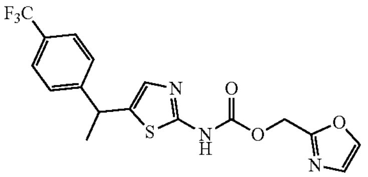 [SMILES: CC(c1ccc(C(F)(F)F)cc1)c1cnc(NC(=O)OCc2ncco2)s1] | n/a | 398.0 |

-continued

| Ex. No. | Name | Structure | Intermediates requiring synthesis | ES-MS [M + H]$^+$ |
|---|---|---|---|---|
| 44 | oxazol-2-ylmethyl (5-(1-(4-fluorophenyl) ethyl)thiazol-2-yl)carbamate | 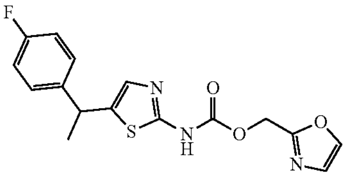 [SMILES: CC(c1ccc(F)cc1)c1cnc(NC(=O)OCc2ncco2)s1] | n/a | 348.2 |
| 45 | oxazol-2-ylmethyl (5-(1-(3,4,5-trimethoxyphenyl) ethyl)thiazol-2-yl)carbamate | 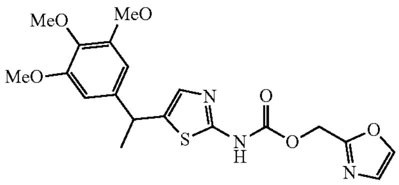 [SMILES: COc1cc(C(C)c2cnc(NC(=O)OCc3ncco3)s2)cc(OC)c1OC] | n/a | 420.1 |
| 46 | oxazol-2-ylmethyl (5-(4-chloro-3-methoxybenzyl) thiazol-2-yl)carbamate | 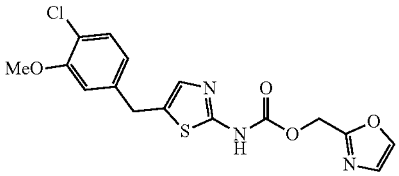 [SMILES: COc1cc(Cc2cnc(NC(=O)OCc3ncco3)s2)ccc1Cl] | n/a | 380.0 |
| 47 | (1,3,4-oxadiazol-2-yl)methyl (5-(1-(4-chlorophenyl) ethyl)thiazol-2-yl)carbamate | 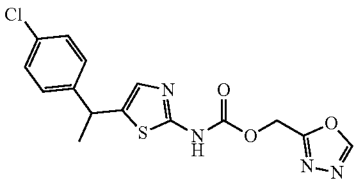 [SMILES: CC(c1ccc(Cl)cc1)c1cnc(NC(=O)OCc2nnco2)s1] | n/a | 365.0 |
| 48 | 1-(oxazol-2-yl)ethyl (5-(1-(4-chlorophenyl) ethyl)thiazol-2-yl)carbamate | 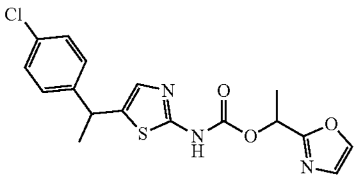 [SMILES: CC(OC(=O)Nc1ncc(C(C)c2ccc(Cl)cc2)s1)c1ncco1] | n/a | 378.0 |
| 49 | oxazol-2-ylmethyl (5-(1-(4-acetamidophen yl)ethyl) thiazol-2-yl)carbamate | 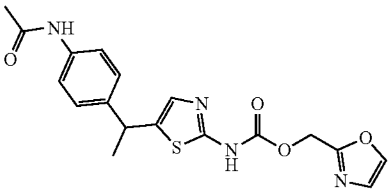 [SMILES: CC(=O)Nc1ccc(C(C)c2cnc(NC(=O)OCc3ncco3)s2)cc1] | n/a | 387.1 |
| 50 | 2-methoxyethyl (5-(1-(4-chlorophenyl) ethyl)thiazol-2-yl)carbamate | 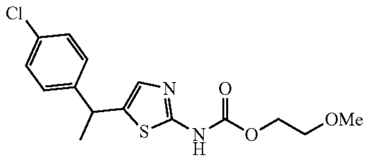 [SMILES: COCCOC(=O)Nc1ncc(C(C)c2ccc(Cl)cc2)s1] | n/a | 341.1 |
| 51 | 3-methoxypropyl (5-(1-(4-chlorophenyl) ethyl)thiazol-2-yl)carbamate | 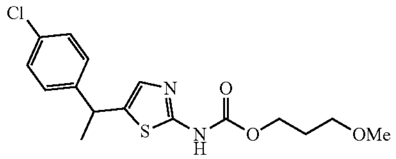 [SMILES: COCCCOC(=O)Nc1ncc(C(C)c2ccc(Cl)cc2)s1] | n/a | 355.1 |

-continued

| Ex. No. | Name | Structure | Intermediates requiring synthesis | ES-MS [M + H]$^+$ |
|---|---|---|---|---|
| 52 | oxazol-2-ylmethyl (5-((6-methoxypyridin-3-yl)methyl)thiazol-2-yl)carbamate | 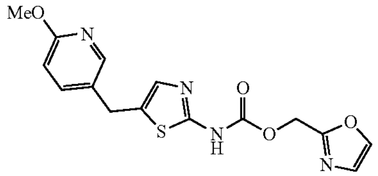 [SMILES: COc1ccc(Cc2cnc(NC(=O)OCc3ncco3)s2)cn1] | n/a | 347.1 |
| 53 | oxazol-2-ylmethyl (5-(3-(azetidin-1-yl)-4-chlorobenzyl) thiazol-2-yl)carbamate | 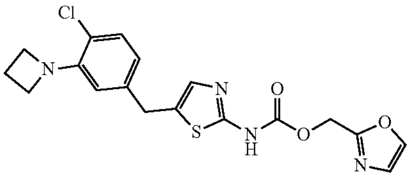 [SMILES: O=C(Nc1ncc(Cc2ccc(Cl)c(N3CCC3)c2)s1)OCc1ncco1] | 3-(azetidin-1-yl)-4-chlorobenzaldehyde | 405.1 |
| 54 | oxazol-2-ylmethyl (5-(1-(1H-benzo[d] imidazol-5-yl)ethyl) thiazol-2-yl)carbamate | 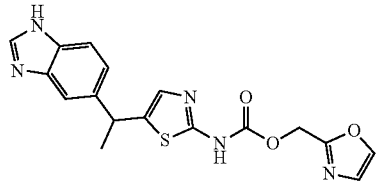 [SMILES: CC(c1ccc2[nH]cnc2c1)c1cnc(NC(=O)OCc2ncco2)s1] Step 1 used Boc-protected starting material: tert-butyl 5-acetyl-1H-benzo[d]imidazole-1-carboxylate. The Boc group was cleaved in Step | n/a | 370.1 |
| 55 | (1-methyl-1H-imidazol-2-yl)methyl (5-(1-(4-chlorophenyl) ethyl)thiazol-2-yl)carbamate | 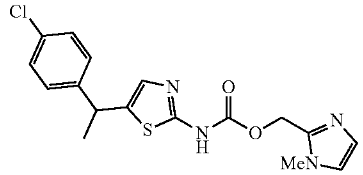 [SMILES: CC(c1ccc(Cl)cc1)c1cnc(NC(=O)OCc2nccn2C)s1] | n/a | 377.1 |
| 56 | oxazol-2-ylmethyl (5-(7-chlorochroman-4-yl)thiazol-2-yl)carbamate | 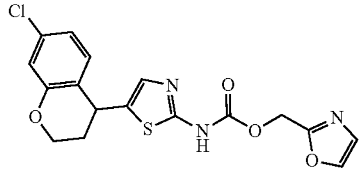 [SMILES: O=C(Nc1ncc(C2CCOc3cc(Cl)ccc32)s1)OCc1ncco1] | n/a | 392.1 |
| 57 | oxazol-2-ylmethyl (5-(chroman-4-yl)thiazol-2-yl)carbamate | 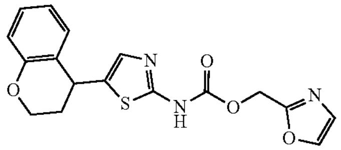 [SMILES: O=C(Nc1ncc(C2CCOc3ccccc32)s1)OCc1ncco1] | n/a | 358.1 |
| 58 | oxazol-2-ylmethyl (5-(1-(2-methoxypyridin-4-yl)ethyl)thiazol-2-yl)carbamate | 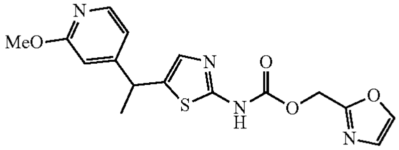 [SMILES: COc1cc(C(C)c2cnc(NC(=O)OCc3ncco3)s2)ccn1] | n/a | 361.1 |
| 59 | oxazol-2-ylmethyl (5-((4-chlorophenyl) (oxetan-3-yl)methyl) thiazol-2-yl)carbamate | 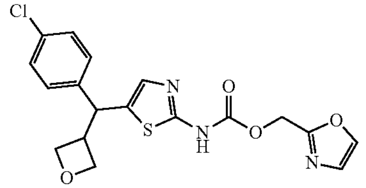 [SMILES: O=C(Nc1ncc(C(c2ccc(Cl)cc2)C2COC2)s1)OCc1ncco1] | (4-chlorophenyl) (oxetan-3-yl) methanone | 406.1 |

-continued

| Ex. No. | Name | Structure | Intermediates requiring synthesis | ES-MS [M + H]+ |
|---|---|---|---|---|
| 60 | oxazol-2-ylmethyl (5-(7-chloroisochroman-4-yl)thiazol-2-yl)carbamate | 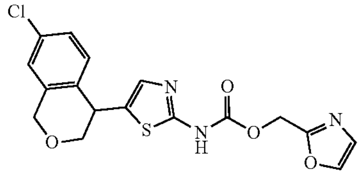 [SMILES: O=C(Nc1ncc(C2COCc3cc(Cl)ccc32)s1)OCc1ncco1] | n/a | 392.1 |
| 61 | oxazol-2-ylmethyl (5-(8-chlorochroman-4-yl)thiazol-2-yl)carbamate | 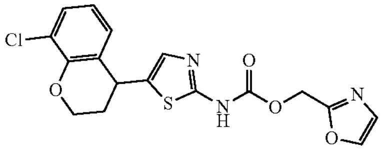 [SMILES: O=C(Nc1ncc(C2CCOc3c(Cl)cccc32)s1)OCc1ncco1] | n/a | 391.9 |
| 62 | oxazol-2-ylmethyl (5-(1-(6-methoxypyridin-2-yl)ethyl)thiazol-2-yl)carbamate | 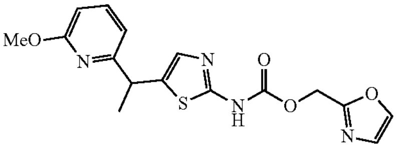 [SMILES: COc1cccc(C(C)c2cnc(NC(=O)OCc3ncco3)s2)n1] | n/a | 361.1 |
| 63 | oxazol-2-ylmethyl (5-(1-(1-methyl-1H-pyrazol-4-yl)ethyl) thiazol-2-yl)carbamate | 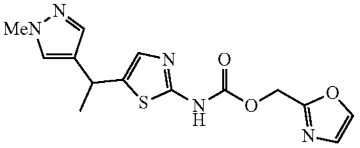 [SMILES: CC(c1cnn(C)c1)c1cnc(NC(=O)OCc2ncco2)s1] | n/a | 334.1 |
| 64 | oxazol-2-ylmethyl (R)-(5-(1-(2-(difluoromethoxy) pyrimidin-5-yl)ethyl) thiazol-2-yl)carbamate | 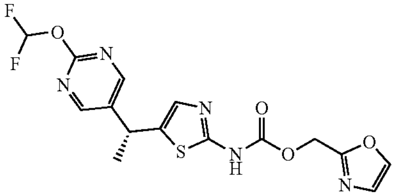 [SMILES: C[C@H](c1cnc(OC(F)F)nc1)c1cnc(NC(=O)OCc2ncco2)s1] $[\alpha]_D^{20}$ −4.0 (c 0.12, DMSO) | 1-(2-(difluoromethoxy) pyrimidin-5-yl) ethan-1-one | 398.0 |
| 65 | oxazol-2-ylmethyl (R)-(5-(1-(6-chloropyridin-3-yl)ethyl) thiazol-2-yl)carbamate | 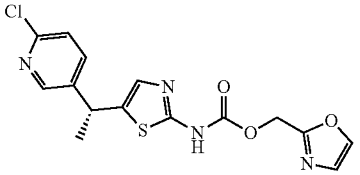 [SMILES: C[C@H](c1ccc(Cl)nc1)c1cnc(NC(=O)OCc2ncco2)s1] RT 1.47 min Column: CHIRALPAK ® AD-3 4.6 × 50 mm, 3 micron; Phase A: $CO_2$, Phase B: 1/1 IPA/[EtOH (0.05% DEA)]; Isocratic elution: B:A 40:60; Flow rate: 3 mL/min; Detector: PDA; Column temperature: 35° C.; Back pressure: 100 Bar | n/a | 365.0 |

-continued

| Ex. No. | Name | Structure | Intermediates requiring synthesis | ES-MS $[M + H]^+$ |
|---|---|---|---|---|
| 66 | oxazol-2-ylmethyl (S)-(5-(1-(6-chloropyridin-3-yl)ethyl) thiazol-2-yl)carbamate | 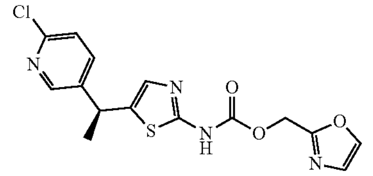 [SMILES: C[C@@H](c1ccc(Cl)nc1)c1cnc(NC(=O)OCc2ncco2)s1]<br>RT 1.84 min<br>Column: CHIRALPAK ® AD-3 4.6 x 50 mm, 3 micron; Phase A: $CO_2$, Phase B: 1/1 IPA/[EtOH (0.05% DEA)]; Isocratic elution: B:A 40:60; Flow rate: 3mL/min; Detector: PDA; Column temperature: 35° C.; Back pressure: 100 Bar | n/a | 365.0 |
| 67 | oxazol-2-ylmethyl (S)-(5-(1-(5-methoxypyrazin-2-yl)ethyl)thiazol-2-yl)carbamate | 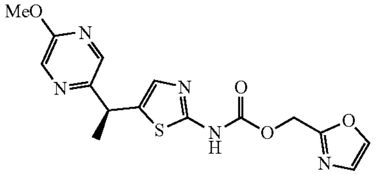 [SMILES: COc1cnc([C@H](C)c2cnc(NC(=O)OCc3ncco3)s2)cn1]<br>$[\alpha]_D^{20}$ +48.3 (c 0.19, methanol) | n/a | 362.1 |
| 68 | oxazol-2-ylmethyl (R)-(5-(1-(5-methoxypyrazin-2-yl)ethyl)thiazol-2-yl)carbamate | 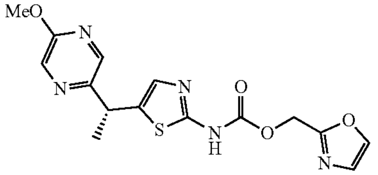 [SMILES: COc1cnc([C@@H](C)c2cnc(NC(=O)OCc3ncco3)s2)cn1]<br>$[\alpha]_D^{20}$ −45.2 (c 0.19, methanol) | n/a | 362.1 |
| 69 | oxazol-2-ylmethyl (5-(2-aminobenzyl) thiazol-2-yl)carbamate | 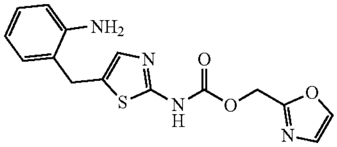 [SMILES: Nc1ccccc1Cc1cnc(NC(=O)OCc2ncco2)s1]<br>Step 1 used 2-nitrobenzaldehyde. A final nitro-reduction step provided the final compound: Fe (5 eq), $NH_4Cl$ (5 eq), EtOH, $H_2O$ 60° C., 2 h | n/a | 331.0 |
| 70 | oxazol-2-ylmethyl (5-(1-(4-hydroxyphenyl) ethyl)thiazol-2-yl)carbamate | 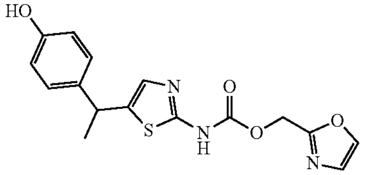 [SMILES: CC(c1ccc(O)cc1)c1cnc(NC(=O)OCc2ncco2)s1]<br>Step 1 used TIPS-protected starting material: 1-(4-((triisopropylsilyl)oxy)phenyl)ethan-1-one. A final TIPS-removal step provided the title compound: LiOAc (2 eq), DMF, 40° C., 12 h. | 1-(4-((triisopropylsilyl) oxy)phenyl)ethan-1-one | 346.0 |

-continued

| Ex. No. | Name | Structure | Intermediates requiring synthesis | ES-MS $[M + H]^+$ |
|---|---|---|---|---|
| 71 | oxazol-2-ylmethyl (5-(1-(5-(trifluoromethyl)pyridin-2-yl)ethyl)thiazol-2-yl)carbamate | 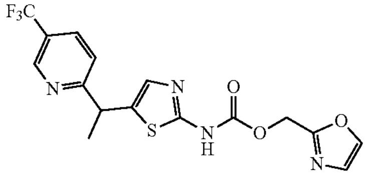 Step 2 furnished the dihydrothiazole: (E)-5-(1-(5-(trifluoromethyl)pyridin-2-yl)ethylidene)-4,5-dihydrothiazol-2-amine. An additional isomerization step was used to provide the terminal thiazole: DBU (3 eq), $CH_2Cl_2$, 20° C., 12 h | n/a | 399.0 |
| 72 | oxazol-2-ylmethyl (5-((3-(3-aminopropyl)-2-oxo-2,3-dihydrobenzo[d]oxazol-5-yl)methyl) thiazol-2-yl)carbamate | 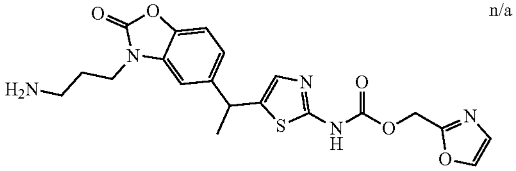 Step 1 used 2-oxo-2,3-dihydrobenzo[d]oxazole-5-carbaldehyde. The product of Step 2 was alkylated with Boc-protected amine: tert-butyl (3-bromopropyl)carbamate (1.2 eq), $K_2CO_3$ (3 eq), DMF, 25° C., 12 h. A final Boc-removal step provided the title compound: 4M HCl in dioxane, $CH_2Cl_2$, 25° C., 2 h. | n/a | 430.1 |
| 73 | oxazol-2-ylmethyl (5-(1-(6-(trifluoromethyl) pyridin-3-yl)ethyl) thiazol-2-yl)carbamate | 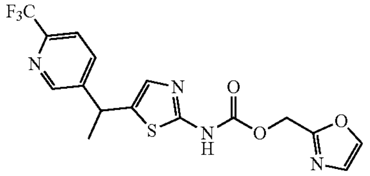 [SMILES: CC(c1ccc(C(F)(F)F)nc1)c1cnc(NC(=O)OCc2ncco2)s1] Step 2 furnished the dihydrothiazole: oxazol-2-ylmethyl (E)-(5-(1-(6-(trifluoromethyl)pyridin-3-yl)ethylidene)-4,5-dihydrothiazol-2-yl)carbamate. An additional isomerization step was used to provide the terminal thiazole: DBU (3 eq), DCE, 25° C., 12 h | n/a | 399.0 |
| 74 | oxazol-2-ylmethyl (5-(1-(5-chloropyridin-2-yl)ethyl) thiazol-2-yl)carbamate | 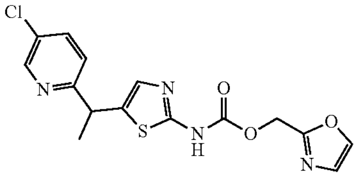 [SMILES: CC(c1ccc(Cl)cn1)c1cnc(NC(=O)OCc2ncco2)s1] Step 2 furnished the dihydrothiazole: oxazol-2-ylmethyl (E)-(5-(1-(5-chloropyridin-2-yl)ethylidene)-4,5-dihydrothiazol-2-yl)carbamate. An additional isomerization step was used to provide the thiazole: DBU (3 eq), DCE, 25° C., 12 h | n/a | 365.1 |

-continued

| Ex. No. | Name | Structure | Intermediates requiring synthesis | ES-MS $[M + H]^+$ |
|---|---|---|---|---|
| 75 | oxazol-2-ylmethyl (5-(4-chlorobenzyl) thiazol-2-yl)carbamate | 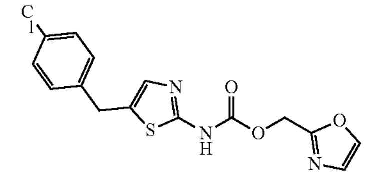 [SMILES: O=C(Nc1ncc(Cc2ccc(Cl)cc2)s1)OCc1ncco1] | n/a | 350.0 |
| 76 | oxazol-2-ylmethyl (5-(4-chloro-3-(piperazin-1-yl)benzyl) thiazol-2-yl)carbamate | 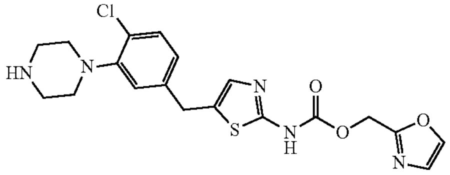 [SMILES: O=C(Nc1ncc(Cc2ccc(Cl)c(N3CCNCC3)c2)s1)OCc1ncco1] Step 1 used Cbz-protected starting material: benzyl 4-(2-chloro-5-formylphenyl)piperazine-1-carboxylate. A final Cbz-removal step provided the title compound: 6M HCl in dioxane, 60° C., 2 h. | benzyl 4-(2-chloro-5-formylphenyl) piperazine-1-carboxylate | 434.1 |
| 77 | oxazol-2-ylmethyl (5-(1-(6-(methoxy-d3)pyridin-3-yl)ethyl) thiazol-2-yl)carbamate | 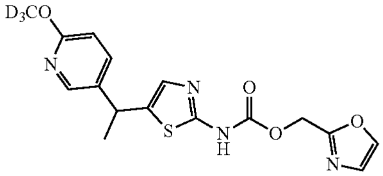 Step 2 furnished the terminal alkene: 5-(1-(6-(methoxy-d3)pyridin-3-yl)vinyl)thiazol-2-amine. A subsequent hydrogenation was required to reduce the double bond: 10% Pd/C, $H_2$, MeOH, 50° C., 12 h. | 1-(6-(methoxy-d3)pyridin-3-yl)ethan-1-one | 364.0 |
| 78 | oxazol-2-ylmethyl (5-(1-(4-chloro-3-((2-methoxyethyl) (methyl)amino )phenyl)ethyl) thiazol-2-yl)carbamate | 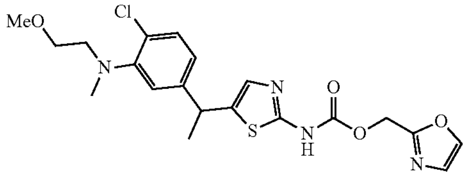 [SMILES: COCCN(C)c1cc(C(C)c2cnc(NC(=O)OCc3ncco3)s2)ccc1Cl] Step 2 furnished the terminal alkene: 5-(1-(4-chloro-3-((2-methoxyethyl)(methyl)amino)phenyl )vinyl)thiazol-2-amine. A subsequent hydrogenation was required to reduce the double bond: Pt/C, $H_2$ (50 PSI), MeOH, 60° C., 12 h. | 1-(4-chloro-3-((2-methoxyethyl) (methyl)amino) phenyl)ethan-1-one | 451.1 |
| 79 | oxazol-2-ylmethyl (5-(1-(4-chloro-3-morpholinophenyl) ethyl)thiazol-2-yl)carbamate | 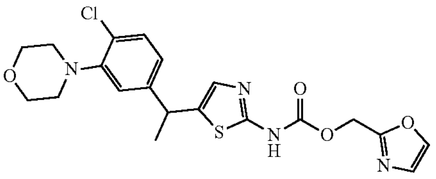 [SMILES: CC(c1ccc(Cl)c(N2CCOCC2)c1)c1cnc(NC(=O)OCc2ncco2)s1] Step 2 furnished the terminal alkene: 5-(1-(4-chloro-3-morpholinophenyl)vinyl)thiazol-2-amine. A subsequent hydrogenation was required to reduce the double bond: Pt/C, $H_2$ (50 PSI), MeOH, 60° C., 12 h. | 1-(4-chloro-3-morpholinophenyl) ethan-1-one | 449.1 |

-continued

| Ex. No. | Name | Structure | Intermediates requiring synthesis | ES-MS $[M + H]^+$ |
|---|---|---|---|---|
| 80 | oxazol-2-ylmethyl (5-(1-(4-chlorophenyl)-2,2,2-trifluoroethyl) thiazol-2-yl)carbamate | 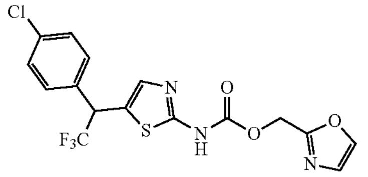 [SMILES: O=C(Nc1ncc(C(c2ccc(Cl)cc2)C(F)(F)F)s1)OCc1ncco1]<br>Step 2 removed the Boc group but not the hydroxyl. An additional dihydroxylation step was required: iodine (1.5 eq), hypophosphorous acid (8 eq), AcOH, 100° C., 16 h. | n/a | 418.0 |
| 81 | oxazol-2-ylmethyl (5-(1-(4-(oxetan-3-yl)phenyl) ethyl)thiazol-2-yl)carbamate | 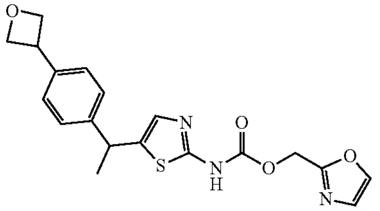 [SMILES: CC(c1ccc(C2COC2)cc1)c1cnc(NC(=O)OCc2ncco2)s1]<br>Step 1 used 1-(4-bromophenyl)ethan-1-one. An additional final step was required to convert the bromide to the oxetane: 4,4,5,5-tetramethyl-2-(oxetan-3-yl)-1,3,2-dioxaborolane (2 eq), (4,4'-dtbbpy)$NiCl_2$ (0.05 eq), $(Ir[dF(CF_3)ppy]_2(dtbpy))PF_6$ (0.01 eq), morpholine (1.5 eq), DMF, 25 ° C., 16 h | n/a | 386.1 |
| 82 | oxazol-2-ylmethyl (5-(1-(4-(3-hydroxyoxetan-3-yl)phenyl)ethyl) thiazol-2-yl)carbamate | 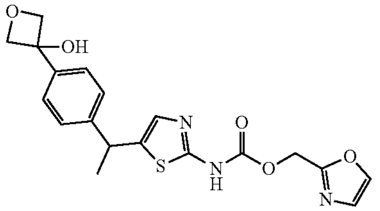 [SMILES: CC(c1ccc(C2(O)COC2)cc1)c1cnc(NC(=O)OCc2ncco2)s1] | 3-(4-(1-(2-aminothiazol-5-yl)ethyl)phenyl) oxetan-3-ol | 402.1 |

Synthetic Procedure E

Example 83: Oxazol-2-ylmethyl (R)-(5-(1-(6-cyclopropoxypyridin-3-yl)ethyl)thiazol-2-yl)carbamate

Example 84: Oxazol-2-ylmethyl (S)-(5-(1-(6-cyclopropoxypyridin-3-yl)ethyl)thiazol-2-yl)carbamate Step 1

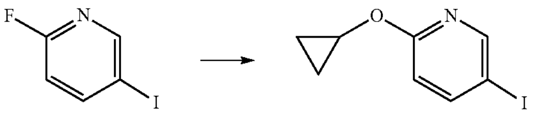 [SMILES: Fc1ccc(I)cn1 ; Ic1ccc(OC2CC2)nc1]

Cyclopropanol (10.0 g, 172 mmol) was added to a mixture of potassium tert-butoxide (19.2 g, 171 mmol) and 2-fluoro-5-iodopyridine (20.0 g, 89.7 mmol) in THF (200 mL). The reaction mixture was stirred at 80° C. for 3 h, then filtered and concentrated in vacuo. Flash column chromatography on silica (EtOAc:PE, 0:1 to 1:19) afforded 2-cyclopropoxy-5-iodopyridine (13.0 g, 42%) as a yellow oil; ES-MS $[M+H]^+$: 262.0.

Step 2

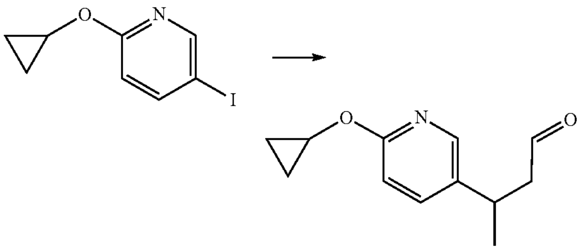

Palladium(II) acetate (870 mg, 3.88 mmol) was added to a mixture of (E)-but-2-en-1-ol (1.85 g, 25.6 mmol), TBAB (6.17 g, 19.2 mmol), sodium bicarbonate (3.26 g, 38.8 mmol) and 2-cyclopropoxy-5-iodopyridine (5.00 g, 19.2 mmol) in DMF (100 mL). The reaction mixture was stirred at 40° C. for 12 h, then diluted with brine (120 mL) and extracted into EtOAc (2×100 mL). The combined organic extracts were dried over anhydrous sodium sulfate and concentrated in vacuo. Flash column chromatography on silica (EtOAc:PE, 0:1 to 3:7) afforded 3-(6-cyclopropoxypyridin-3-yl)butanal (2.40 g, 61%) as a yellow oil; ES-MS $[M+H]^+$: 206.2.

Step 3

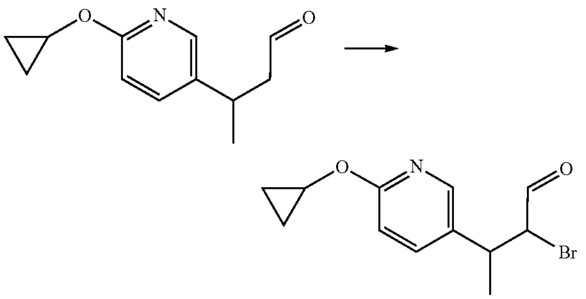

Aqueous hydrobromic acid solution (1.6 g, 5.93 mmol) and bromine (0.30 mL, 5.82 mmol) were added to a solution of 3-(6-cyclopropoxypyridin-3-yl)butanal (1.00 g, 4.87 mmol) in dichloromethane (5 mL) at 0° C. The reaction mixture was stirred at this temperature for 1 h, then diluted with water (20 mL) and extracted into dichloromethane (3 30 mL). The combined organic extracts were dried over anhydrous sodium sulfate and concentrated in vacuo to afford 2-bromo-3-(6-cyclopropoxypyridin-3-yl)butanal (330 mg, crude) as a yellow oil; ES-MS $[M+H]^+$: 284.0.

Step 4

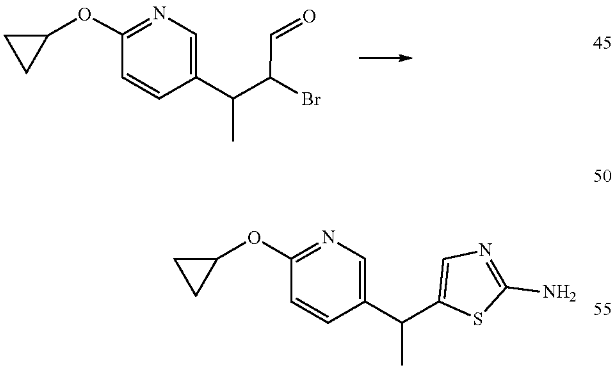

Thiourea (280 mg, 3.68 mmol) was added to a solution of 2-bromo-3-(6-cyclopropoxypyridin-3-yl)butanal (330 mg, 1.16 mmol) in ethanol (5 mL). The reaction mixture was stirred at 90° C. for 12 h, then concentrated in vacuo and purified by flash column chromatography on silica (EtOAc: PE, 0:1 to 1:1) to afford 5-(1-(6-cyclopropoxypyridin-3-yl)ethyl)thiazol-2-amine (210 mg, 62%) as a yellow solid; ES-MS $[M+H]^+$: 262.1.

Step 5

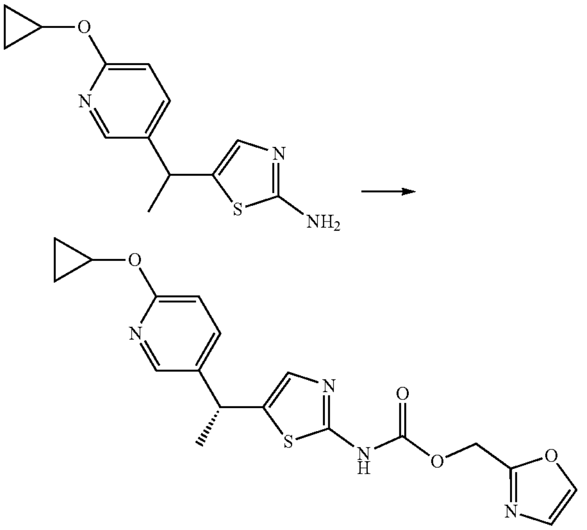

Example 83

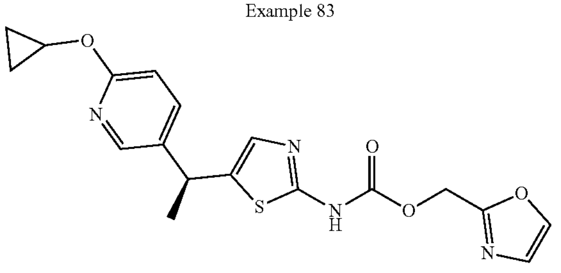

Example 84

CDI (590 mg, 3.64 mmol) was added to a solution of oxazol-2-ylmethanol (360 mg, 3.63 mmol) in THF (10 mL) and the resulting mixture was stirred at 60° C. for 4 h. 5-(1-(6-Cyclopropoxypyridin-3-yl)ethyl)thiazol-2-amine (190 mg, 0.73 mmol), triethylamine (0.79 mL, 2.17 mmol) and DMAP (20 mg, 0.16 mmol) were then added and stirring was continued at 60° C. for 12 h. Acetic acid was added until the pH was ~6 and the mixture was filtered. The filtrate was concentrated in vacuo, then purified by preparative HPLC (column: Welch Xtimate C18, 5 μm, 25×150 mm; gradient: acetonitrile:[water (0.1% formic acid)]; gradient: 70:30→40:60) and preparative SFC (column: CHIRALCEL® OX-10/SFC 50×250 mm, 10 micron; $CO_2$:ethanol (0.1% $NH_4OH$) 60:40) to afford oxazol-2-ylmethyl (R)-(5-(1-(6-cyclopropoxypyridin-3-yl)ethyl)thiazol-2-yl)carbamate (37 mg, 13%, Example 83) as a white solid; Retention time: 1.24; $\delta_H$ (400 MHz; DMSO-d6) 11.98-11.75 (1H, m), 8.19-8.10 (2H, m), 7.66-7.57 (1H, m), 7.29-7.14 (2H, m), 6.81 (1H, d, J 8.6 Hz), 5.27 (2H, s), 4.38-4.28 (1H, m), 4.20-4.12 (1H, m), 1.64-1.54 (3H, m), 0.77-0.70 (2H, m), 0.68-0.61 (2H, m); ES-MS $[M+H]^+$: 387.1 and oxazol-2-ylmethyl (S)-(5-(1-(6-cyclopropoxypyridin-3-yl)ethyl)thiazol-2-yl)carbamate (37 mg, 13%, Example 84) as a white solid; Retention time: 0.99; $\delta_H$ (400 MHz; DMSO-d6) 11.98-11.75 (1H, m), 8.19-8.10 (2H, m), 7.66-7.57 (1H, m), 7.29-7.14 (2H, m), 6.81 (1H, d, J 8.6 Hz), 5.27 (2H, s), 4.38-4.28 (1H, m), 4.20-4.12 (1H, m), 1.64-1.54 (3H, m), 0.77-0.70 (2H, m), 0.68-0.61 (2H, m); ES-MS $[M+H]^+$: 387.1.

Example 85 was also prepared using synthetic procedure E:

| Ex. No. | Name | Structure | Starting material | ES-MS [M + H]+ |
|---|---|---|---|---|
| 85 | oxazol-2-ylmethyl (5-(1-(4-chloro-2-cyanophenyl)hyetl) thiazol-2-yl)carbamate | 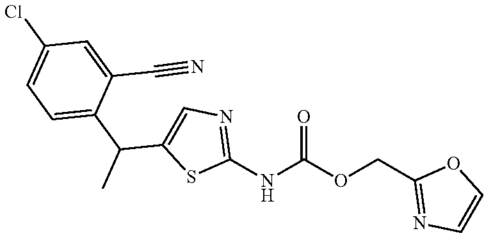 [SMILES: CC(c1cnc(NC(=O)OCc2ncco2)s1)c1ccc(Cl)cc1C#N]<br>No step 1 | 2-bromo-5-chlorobenzonitrile | 388.9 |

Synthetic Procedure F

Example 86: N-(5-(1-(4-Chlorophenyl)ethyl)thiazol-2-yl)-3-phenylazetidine-1-carboxamide

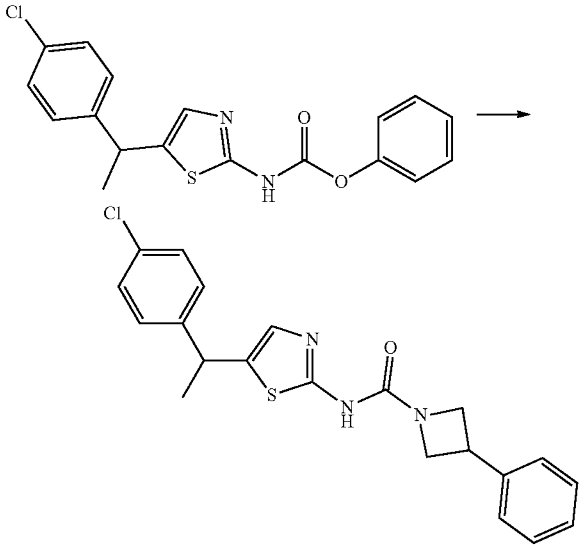

3-Phenylazetidine hydrochloride (57 mg, 0.33 mmol) was added to a solution of phenyl (5-(1-(4-chlorophenyl)ethyl) thiazol-2-yl)carbamate* (100 mg, 0.28 mmol) and triethylamine (0.19 mmol, 1.39 mmol) in dichloromethane (2 mL). The reaction mixture was stirred at 25° C. for 12 h. The precipitate was filtered and triturated (acetonitrile:water 1:1, 1 mL) to afford N-(5-(1-(4-chlorophenyl)ethyl)thiazol-2-yl)-3-phenylazetidine-1-carboxamide (49 mg, 44%) as a white solid; $\delta_H$ (400 MHz; DMSO-d6) 10.86 (1H, br s), 7.40-7.33 (6H, m), 7.33-7.24 (3H, m), 7.11 (1H, s), 4.38 (2H, m), 4.31 (1H, m), 3.98-3.91 (2H, m), 3.88-3.79 (1H, m), 1.58 (3H, d, J 7.1 Hz). ES-MS $[M+H]^+$: 398.2.

*Prepared according to Synthetic Procedure C, Steps 1-3

Other examples prepared using synthetic procedure F are shown in the following table. All intermediates are commercially available unless noted (see 'Intermediate synthesis' section).

| Ex. No. | Name | Structure | Intermediates requiring synthesis | ES-MS [M + H]+ |
|---|---|---|---|---|
| 87 | N-(5-(1-(4-chlorophenyl) ethyl)thiazol-2-yl)-3-hydroxyazetidine-1-carboxamide | 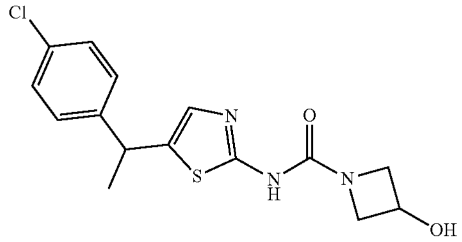 [SMILES: CC(c1ccc(Cl)cc1)c1cnc(NC(=O)N2CC(O)C2)s1] | n/a | 338.1 |

-continued

| Ex. No. | Name | Structure | Intermediates requiring synthesis | ES-MS [M + H]+ |
|---|---|---|---|---|
| 88 | N-(5-(1-(4-chlorophenyl)ethyl)thiazol-2-yl)-3-methoxyazetidine-1-carboxamide | 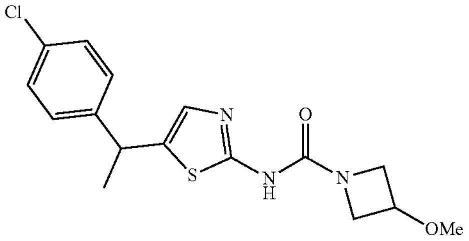 [SMILES: COC1CN(C(=O)Nc2ncc(C(C)c3ccc(Cl)cc3)s2)C1] | n/a | 352.1 |
| 89 | N-(5-(1-(4-chlorophenyl)ethyl)thiazol-2-yl)-1-oxa-6-azaspiro[3.3]heptane-6-carboxamide | 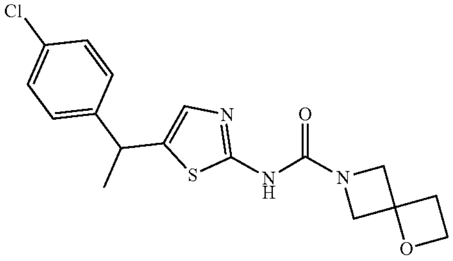 [SMILES: CC(c1ccc(Cl)cc1)c1cnc(NC(=O)N2CC3(CCO3)C2)s1] | n/a | 364.0 |
| 90 | N-(5-(1-(4-chlorophenyl)ethyl)thiazol-2-yl)-3-(oxazol-2-yl)azetidine-1-carboxamide | 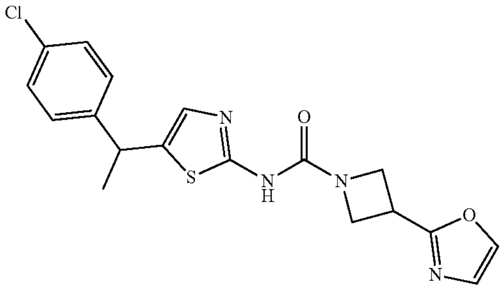 [SMILES: CC(c1ccc(Cl)cc1)c1cnc(NC(=O)N2CC(c3ncco3)C2)s1] | n/a | 389.0 |
| 91 | N-(5-(1-(4-chlorophenyl)ethyl)thiazol-2-yl)-2-oxa-6-azaspiro[3.3]heptane-6-carboxamide | 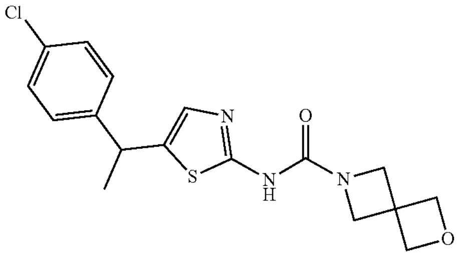 [SMILES: CC(c1ccc(Cl)cc1)c1cnc(NC(=O)N2CC3(COC3)C2)s1] | n/a | 364.1 |
| 92 | N-(5-(1-(4-chlorophenyl)ethyl)thiazol-2-yl)-2-phenylazetidine-1-carboxamide | 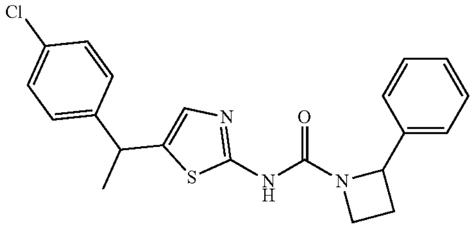 [SMILES: CC(c1ccc(Cl)cc1)c1cnc(NC(=O)N2CCC2c2ccccc2)s1] | n/a | 398.1 |

-continued

| Ex. No. | Name | Structure | Intermediates requiring synthesis | ES-MS [M + H]$^+$ |
|---|---|---|---|---|
| 93 | N-(5-(1-(4-chlorophenyl)ethyl)thiazol-2-yl)-3-(furan-2-yl)azetidine-1-carboxamide | 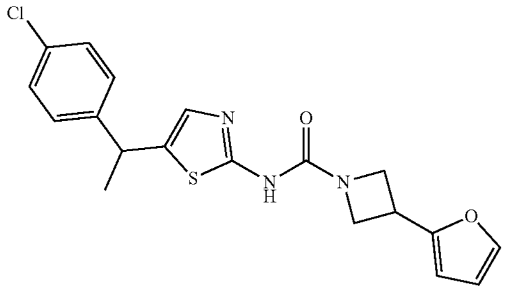 [SMILES: CC(c1ccc(Cl)cc1)c1cnc(NC(=O)N2CC(c3ccco3)C2)s1] | n/a | 388.1 |
| 94 | N-(5-(1-(4-chlorophenyl)ethyl)thiazol-2-yl)-3-(pyridin-4-yl)azetidine-1-carboxamide | 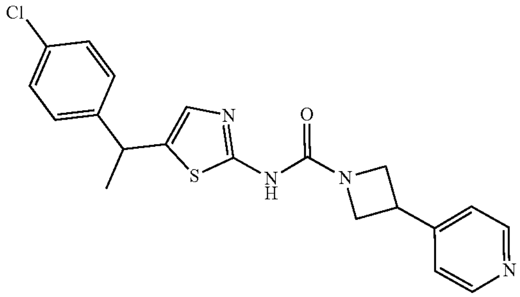 [SMILES: CC(c1ccc(Cl)cc1)c1cnc(NC(=O)N2CC(c3ccncc3)C2)s1] | n/a | 399.2 |
| 95 | 3-(benzo[d]oxazol-2-yl)-N-(5-(1-(4-chlorophenyl)ethyl)thiazol-2-yl)azetidine-1-carboxamide | 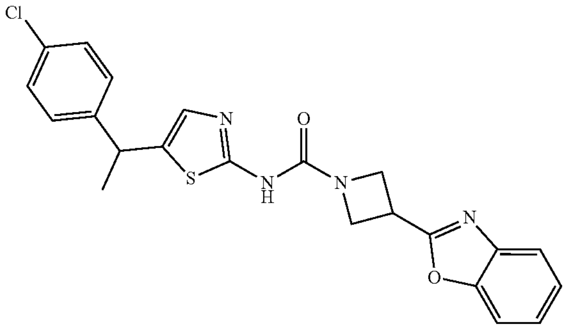 [SMILES: CC(c1ccc(Cl)cc1)c1cnc(NC(=O)N2CC(c3nc4ccccc4o3)C2)s1] | 2-(azetidin-3-yl)benzo[d]oxazole TFA salt | 439.2 |
| 96 | N-(5-(1-(4-chlorophenyl)ethyl)thiazol-2-yl)-3-((trifluoromethoxy)methyl)azetidine-1-carboxamide | 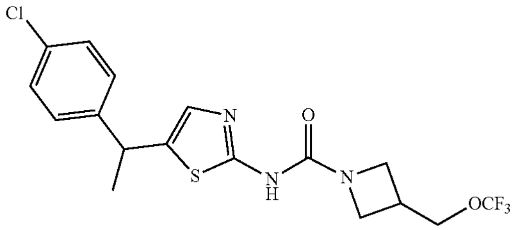 [SMILES: CC(c1ccc(Cl)cc1)c1cnc(NC(=O)N2CC(COC(F)(F)F)C2)s1] | n/a | 420.0 |
| 97 | 1-(5-(1-(4-chlorophenyl)ethyl)thiazol-2-yl)-3-(oxazol-2-ylmethyl)urea | 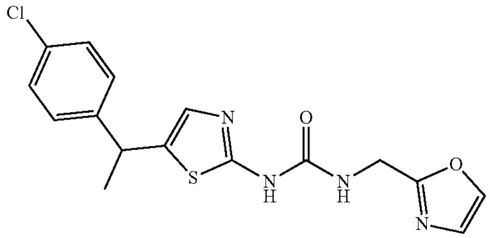 [SMILES: CC(c1ccc(Cl)cc1)c1cnc(NC(=O)NCc2ncco2)s1] | n/a | 363.0 |

-continued

| Ex. No. | Name | Structure | Intermediates requiring synthesis | ES-MS $[M + H]^+$ |
|---|---|---|---|---|
| 98 | N-(5-(1-(4-chlorophenyl) ethyl)thiazol-2-yl)-3-(methoxymethyl)azetidine-1-carboxamide | 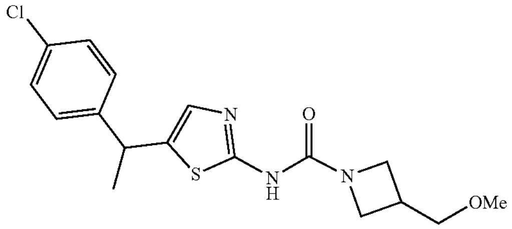 [SMILES: COCC1CN(C(=O)Nc2ncc(C(C)c3ccc(Cl)cc3)s2)C1] | n/a | 366.0 |
| 99 | N-(5-(1-(4-chlorophenyl) ethyl)thiazol-2-yl)-6-oxa-2-azaspiro[3.4] octane-2-carboxamide | 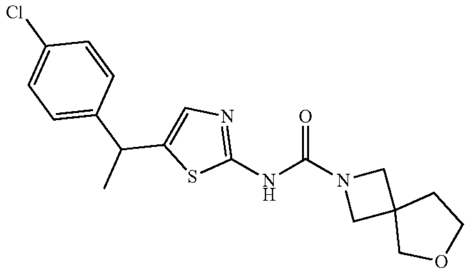 [SMILES: CC(c1ccc(Cl)cc1)c1cnc(NC(=O)N2CC3(CCOC3)C2)s1] | n/a | 378.1 |
| 100 | N-(5-(1-(4-chlorophenyl) ethyl)thiazol-2-yl)-3-(1-methoxyethyl) azetidine-1-carboxamide | 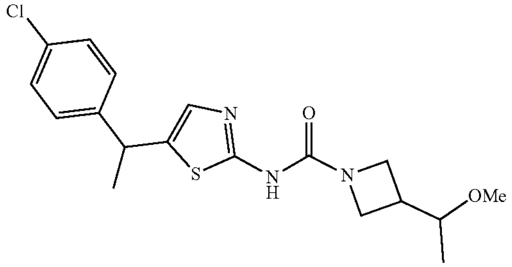 [SMILES: COC(C)C1CN(C(=O)Nc2ncc(C(C)c3ccc(Cl)cc3)s2)C1] | n/a | 380.1 |
| 101 | N-(5-(1-(4-chlorophenyl) ethyl)thiazol-2-yl)-3-methoxy-3-methylazetidine-1-carboxamide | 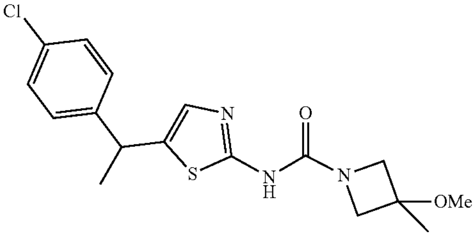 [SMILES: COC1(C)CN(C(=O)Nc2ncc(C(C)c3ccc(Cl)cc3)s2)C1] | n/a | 366.1 |
| 102 | N-(5-(1-(4-chlorophenyl) ethyl)thiazol-2-yl)-3-(pyridin-2-yl)azetidine-1-carboxamide | 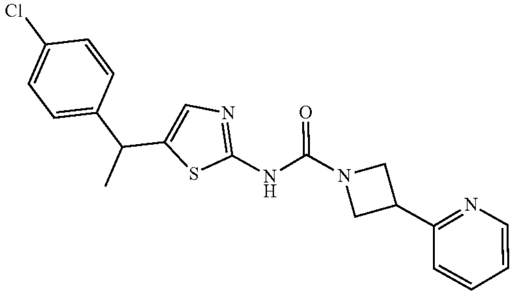 [SMILES: CC(c1ccc(Cl)cc1)c1cnc(NC(=O)N2CC(c3ccccn3)C2)s1] | n/a | 399.0 |

-continued

| Ex. No. | Name | Structure | Intermediates requiring synthesis | ES-MS [M + H]+ |
|---|---|---|---|---|
| 103 | N-(5-(1-(4-chlorophenyl)ethyl)thiazol-2-yl)-3-(pyridin-3-yl)azetidine-1-carboxamide | 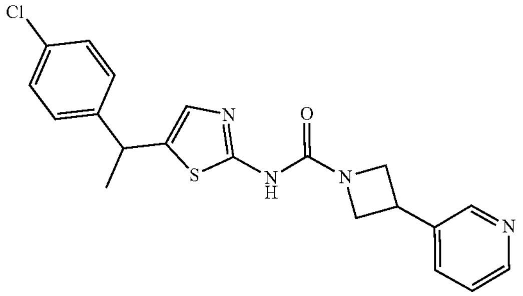 [SMILES: CC(c1ccc(Cl)cc1)c1cnc(NC(=O)N2CC(c3cccnc3)C2)s1] | n/a | 399.1 |
| 104 | N-(5-(1-(4-chlorophenyl)ethyl)thiazol-2-yl)-3-(methoxymethyl)-3-methylazetidine-1-carboxamide | 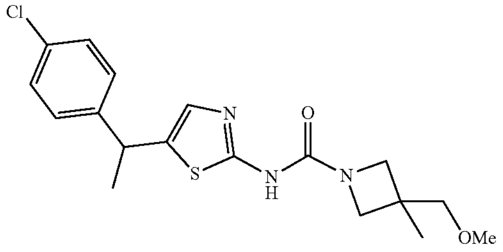 [SMILES: COCC1(C)CN(C(=O)Nc2ncc(C(C)c3ccc(Cl)cc3)s2)C1] | n/a | 380.0 |
| 105 | N-(5-(1-(4-chlorophenyl)ethyl)thiazol-2-yl)-3-fluoro-3-(methoxymethyl)azetidine-1-carboxamide | 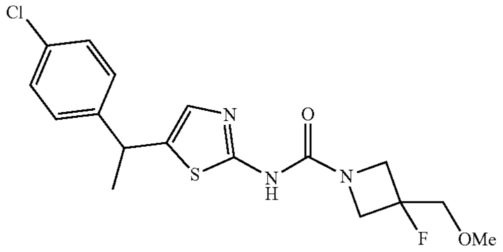 [SMILES: COCC1(F)CN(C(=O)Nc2ncc(C(C)c3ccc(Cl)cc3)s2)C1] | n/a | 384.1 |
| 106 | 1-(5-(1-(4-chlorophenyl)ethyl)thiazol-2-yl)-3-(trans-3-methoxycyclobutyl)urea | 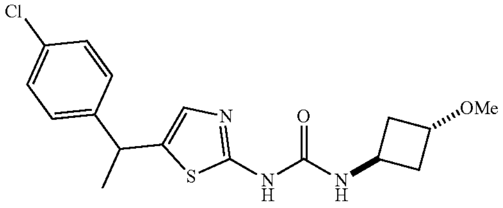 [SMILES: CO[C@H]1C[C@H](NC(=O)Nc2ncc(C(C)c3ccc(Cl)cc3)s2)C1] | n/a | 366.1 |
| 107 | 1-(5-(1-(4-chlorophenyl)ethyl)thiazol-2-yl)-3-(cis-3-methoxycyclobutyl)urea | 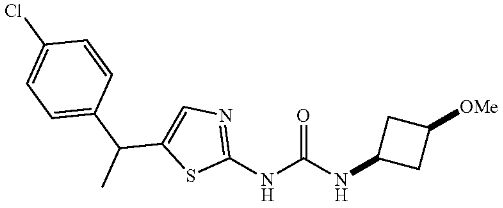 [SMILES: CO[C@H]1C[C@@H](NC(=O)Nc2ncc(C(C)c3ccc(Cl)cc3)s2)C1] | n/a | 366.1 |
| 108 | N-(5-(1-(4-chlorophenyl)ethyl)thiazol-2-yl)-3-methoxy-3-(methoxymethyl)azetidine-1-carboxamide | 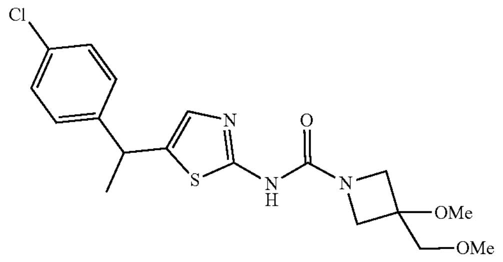 [SMILES: COCC1(OC)CN(C(=O)Nc2ncc(C(C)c3ccc(Cl)cc3)s2)C1] | 3-methoxy-3-(methoxymethyl)azetidine | 396.1 |

-continued

| Ex. No. | Name | Structure | Intermediates requiring synthesis | ES-MS [M + H]+ |
|---|---|---|---|---|
| 109 | N-(5-(1-(4-chlorophenyl)ethyl)thiazol-2-yl)-3-(methylsulfonyl)azetidine-1-carboxamide | 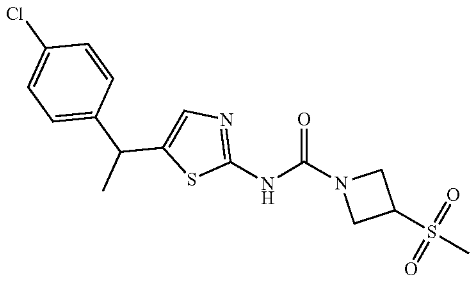 [SMILES: CC(c1ccc(Cl)cc1)c1cnc(NC(=O)N2CC(S(C)(=O)=O)C2)s1] | n/a | 400.2 |
| 110 | (1R,5S,6s)-N-(5-(1-(4-chlorophenyl)ethyl)thiazol-2-yl)-6-methoxy-3-azabicyclo[3.1.0]hexane-3-carboxamide | 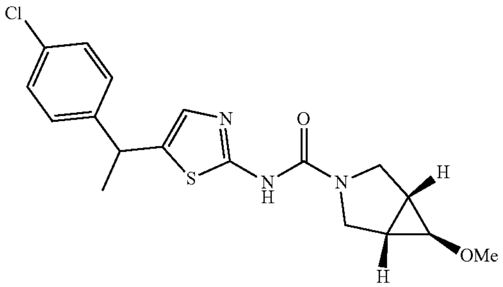 [SMILES: CO[C@H]1[C@@H]2CN(C(=O)Nc3ncc(C(C)c4ccc(Cl)cc4)s3)C[C@@H]21] | 6-methoxy-3-azabicyclo[3.1.0]hexane HCl salt | 378.0 |
| 111 | N-(5-(1-(4-chlorophenyl)ethyl)thiazol-2-yl)-3-hydroxy-3-(methoxymethyl)azetidine-1-carboxamide | 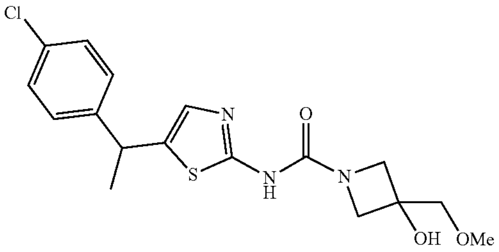 [SMILES: COCC1(O)CN(C(=O)Nc2ncc(C(C)c3ccc(Cl)cc3)s2)C1] | n/a | 383.1 |
| 112 | N-(5-(1-(4-chlorophenyl)ethyl)thiazol-2-yl)-3-(3-methyl-1,2,4-oxadiazol-5-yl)azetidine-1-carboxamide | 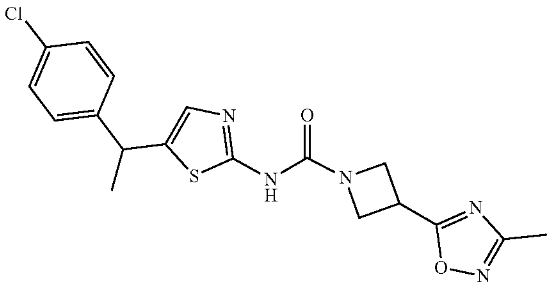 [SMILES: Cc1noc(C2CN(C(=O)Nc3ncc(C(C)c4ccc(Cl)cc4)s3)C2)n1] | n/a | 404.0 |
| 113 | N-(5-(1-(4-chlorophenyl)ethyl)thiazol-2-yl)-3-hydroxy-3-(pyridin-2-yl)azetidine-1-carboxamide | 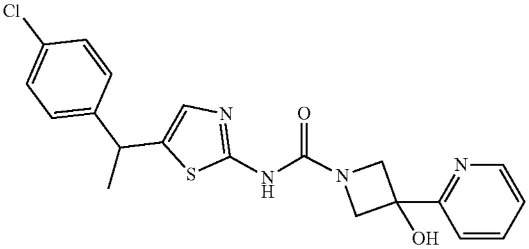 [SMILES: CC(c1ccc(Cl)cc1)c1cnc(NC(=O)N2CC(O)(c3ccccn3)C2)s1] | n/a | 415.0 |

-continued

| Ex. No. | Name | Structure | Intermediates requiring synthesis | ES-MS $[M + H]^+$ |
|---|---|---|---|---|
| 114 | N-(5-(1-(4-chlorophenyl) ethyl)thiazol-2-yl)-3-(3-methoxypyridin-2-yl)azetidine-1-carboxamide | 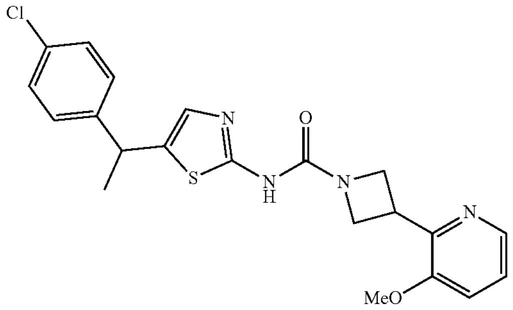 [SMILES: COc1cccnc1C1CN(C(=O)Nc2ncc(C(C)c3ccc(Cl)cc3)s2)C1] | n/a | 429.0 |
| 115 | 1-(5-(1-(4-chlorophenyl) ethyl)thiazol-2-yl)-3-(oxetan-3-yl)urea | 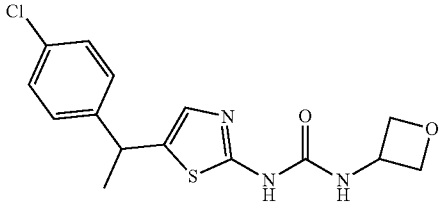 [SMILES: CC(c1ccc(Cl)cc1)c1cnc(NC(=O)NC2COC2)s1] | n/a | 338.1 |
| 116 | N-(5-(1-(4-chlorophenyl) ethyl)thiazol-2-yl)-3-((methoxy-d3)methyl) azetidine-1-carboxamide | 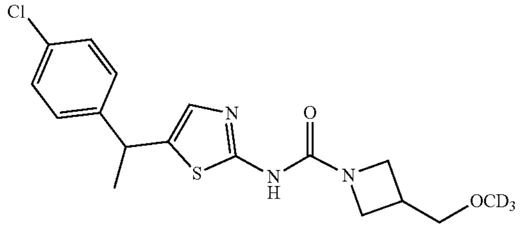 | 3-((methoxy-d3)methyl)azetidine TFA salt | 369.1 |
| 117 | N-(5-(1-(4-chlorophenyl) ethyl)thiazol-2-yl)-3-(difluoromethoxy) azetidine-1-carboxamide | 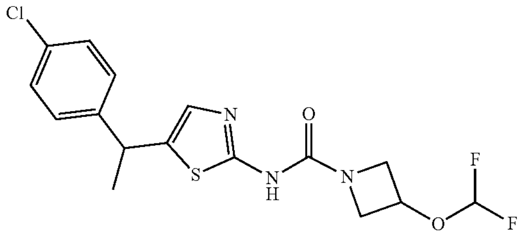 [SMILES: CC(c1ccc(Cl)cc1)c1cnc(NC(=O)N2CC(OC(F)F)C2)s1] | n/a | 388.0 |
| 118 | N-(5-(1-(4-chlorophenyl) ethyl)thiazol-2-yl)-3-(2-methoxypropan-2-yl)azetidine-1-carboxamide | 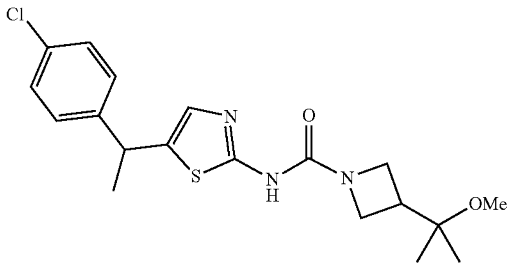 [SMILES: COC(C)(C)C1CN(C(=O)Nc2ncc(C(C)c3ccc(Cl)cc3)s2)C1] | n/a | 394.1 |
| 119 | N-(5-(1-(4-chlorophenyl) ethyl)thiazol-2-yl)-3-(methoxy-d3)azetidine-1-carboxamide | 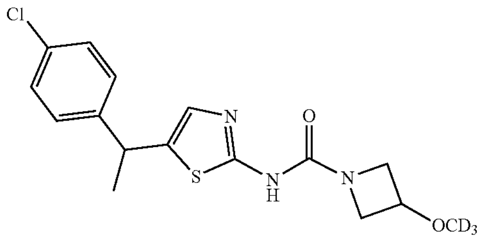 | 3-(methoxy-d3)azetidine TFA salt | 355.0 |

-continued

| Ex. No. | Name | Structure | Intermediates requiring synthesis | ES-MS [M + H]+ |
|---|---|---|---|---|
| 120 | N-(5-(1-(4-chlorophenyl) ethyl)thiazol-2-yl)-3,3-difluoroazetidine-1-carboxamide | 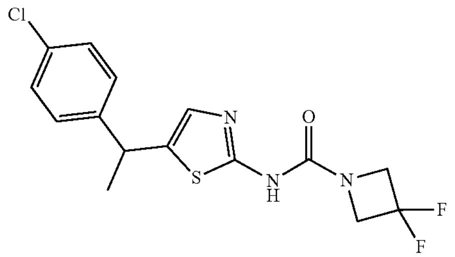 [SMILES: CC(c1ccc(Cl)cc1)c1cnc(NC(=O)N2CC(F)(F)C2)s1] | n/a | 358.1 |
| 121 | N-(5-(1-(4-chlorophenyl) ethyl)thiazol-2-yl)-3,3-difluoropyrrolidine-1-carboxamide | 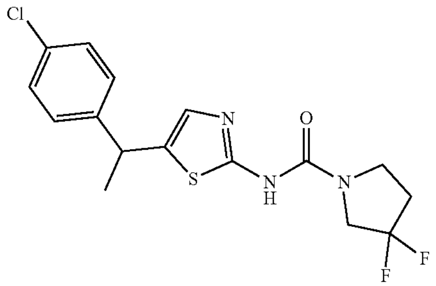 [SMILES: CC(c1ccc(Cl)cc1)c1cnc(NC(=O)N2CCC(F)(F)C2)s1] | n/a | 372.0 |
| 122 | N-(5-(1-(4-chlorophenyl) ethyl)thiazol-2-yl)-3-cyanoazetidine-1-carboxamide | 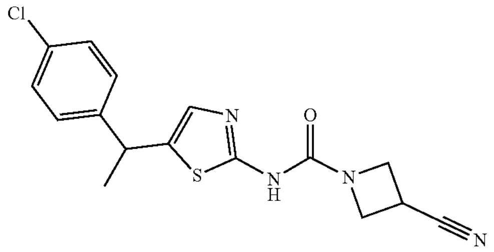 [SMILES: CC(c1ccc(Cl)cc1)c1cnc(NC(=O)N2CC(C#N)C2)s1] | n/a | 347.0 |
| 123 | N-(5-(1-(4-chlorophenyl) ethyl)thiazol-2-yl)-3-methylazetidine-1-carboxamide | 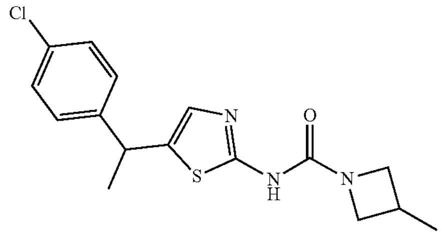 [SMILES: CC1CN(C(=O)Nc2ncc(C(C)c3ccc(Cl)cc3)s2)C1] | n/a | 336.0 |
| 124 | N-(5-(1-(4-chlorophenyl) ethyl)thiazol-2-yl)-3-cyclopropoxyazetidine-1-carboxamide | 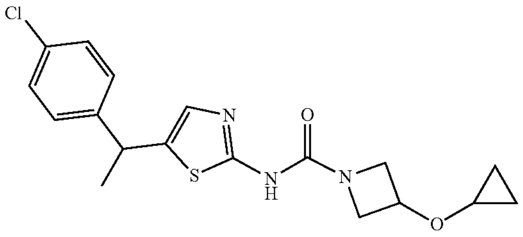 [SMILES: CC(c1ccc(Cl)cc1)c1cnc(NC(=O)N2CC(OC3CC3)C2)s1] | n/a | 378.0 |
| 125 | N-(5-(1-(4-chlorophenyl) ethyl)thiazol-2-yl)azetidine-1-carboxamide | 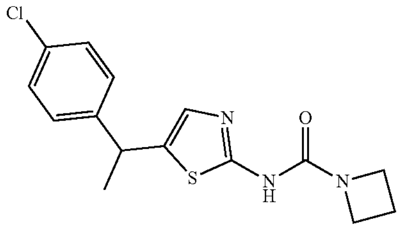 [SMILES: CC(c1ccc(Cl)cc1)c1cnc(NC(=O)N2CCC2)s1] | n/a | 322.1 |

-continued

| Ex. No. | Name | Structure | Intermediates requiring synthesis | ES-MS [M + H]+ |
|---|---|---|---|---|
| 126 | N-(5-(1-(4-chlorophenyl) ethyl)thiazol-2-yl)-3-fluoro-3-((methoxy-d3)methyl) azetidine-1-carboxamide | 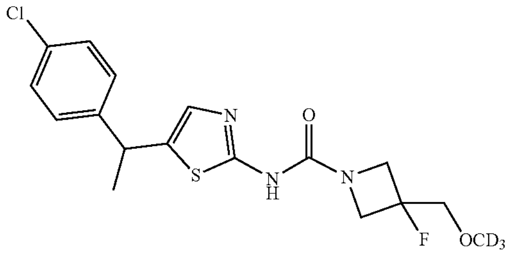 | 3-fluoro-3-((methoxy-d3)methyl)azetidine TFA salt | 387.1 |
| 127 | N-(5-(1-(4-chlorophenyl) ethyl)thiazol-2-yl)-3-(difluoromethyl) azetidine-1-carboxamide | 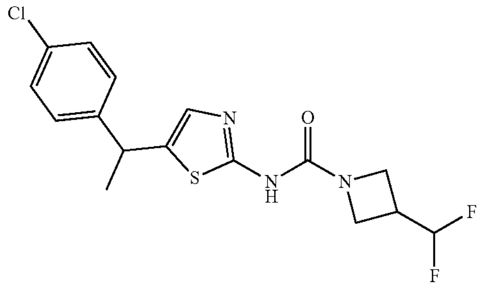 [SMILES: CC(c1ccc(Cl)cc1)c1cnc(NC(=O)N2CC(C(F)F)C2)s1] | n/a | 372.0 |
| 128 | N-(5-(1-(4-chlorophenyl) ethyl)thiazol-2-yl)-3-(trifluorometh yl)azetidine-1-carboxamide | 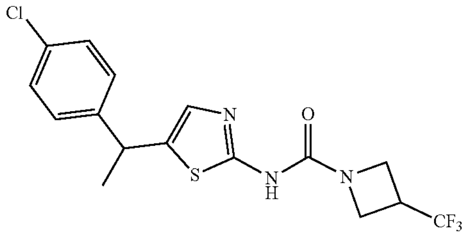 [SMILES: CC(c1ccc(Cl)cc1)c1cnc(NC(=O)N2CC(C(F)(F)F)C2)s1] | n/a | 390.0 |
| 129 | N-(5-(1-(4-chlorophenyl) ethyl)thiazol-2-yl)-6-methoxy-2-azaspiro[3.3] heptane-2-carboxamide | 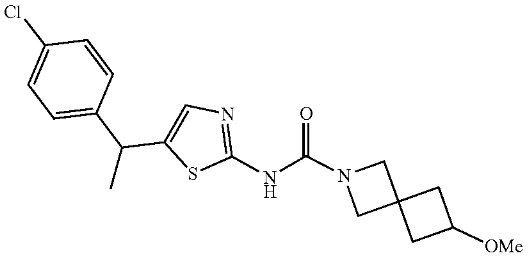 [SMILES: COC1CC2(C1)CN(C(=O)Nc1ncc(C(C)c3ccc(Cl)cc3)s1)C2] | n/a | 392.2 |
| 130 | N-(5-(1-(4-chlorophenyl) ethyl)thiazol-2-yl)-3-methyl-3-(oxazol-2-yl)azetidine-1-carboxamide | 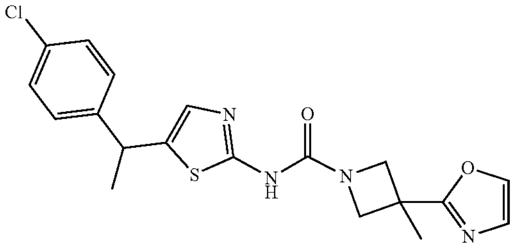 [SMILES: CC(c1ccc(Cl)cc1)c1cnc(NC(=O)N2CC(C)(c3ncco3)C2)s1] | 2-(3-methylazetidin-3-yl)oxazole TFA salt | 403.1 |

-continued

| Ex. No. | Name | Structure | Intermediates requiring synthesis | ES-MS [M + H]+ |
|---|---|---|---|---|
| 131 | N-(5-(1-(4-chlorophenyl)ethyl)thiazol-2-yl)-8-oxa-2,5-diazaspiro[3.5]nonane-2-carboxamide | 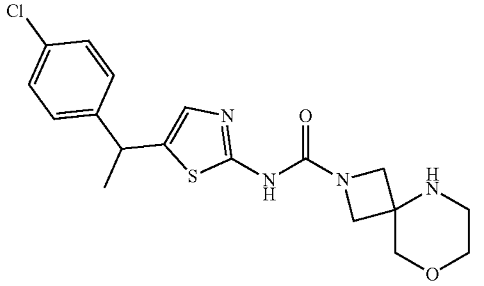 [SMILES: CC(c1ccc(Cl)cc1)c1cnc(NC(=O)N2CC3(COCCN3)C2)s1] Cbz-protected starting material was used: benzyl 8-oxa-2,5-diazaspiro[3.5]nonane-5-carboxylate. A subsequent Cbz-removal step provided the title compound: 6M HCl in dioxane, 60° C., 2 h. | benzyl 8-oxa-2,5-diazaspiro[3.5]nonane-5-carboxylate | 393.1 |
| 132 | N-(5-(1-(4-chlorophenyl)ethyl)thiazol-2-yl)-5-methyl-8-oxa-2,5-diazaspiro[3.5]nonane-2-carboxamide | 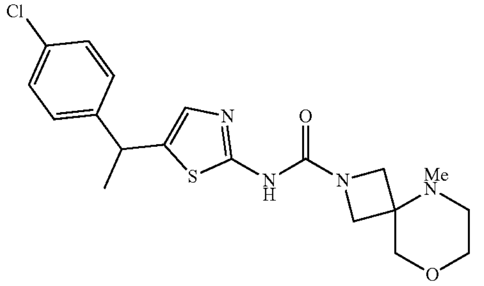 [SMILES: CC(c1ccc(Cl)cc1)c1cnc(NC(=O)N2CC3(COCCN3C)C2)s1] Prepared by methylation of Example 131 using formaldehyde, $NaBH_3CN$, MeOH, 60° C. | benzyl 8-oxa-2,5-diazaspiro[3.5]nonane-5-carboxylate | 407.1 |
| 133 | N-(5-(1-(4-chlorophenyl)ethyl)thiazol-2-yl)-5-oxa-2,8-diazaspiro[3.5]nonane-2-carboxamide | 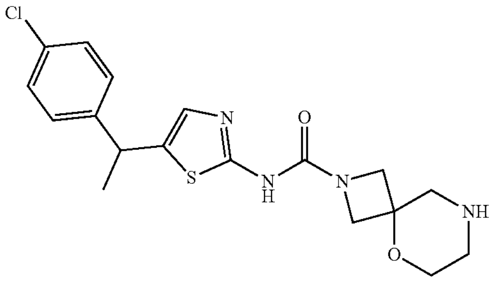 [SMILES: CC(c1ccc(Cl)cc1)c1cnc(NC(=O)N2CC3(CNCCO3)C2)s1] Boc-protected starting material was used: tert-butyl 5-oxa-2,8-diazaspiro[3.5]nonane-8-carboxylate. A subsequent Boc-removal step provided the title compound: 3 eq TFA, $CH_2Cl_2$, 20° C., 2 h. | n/a | 393.1 |

-continued

| Ex. No. | Name | Structure | Intermediates requiring synthesis | ES-MS $[M + H]^+$ |
|---|---|---|---|---|
| 134 | N-(5-(1-(4-chlorophenyl)ethyl)thiazol-2-yl)-8-methyl-5-oxa-2,8-diazaspiro[3.5]nonane-2-carboxamide | 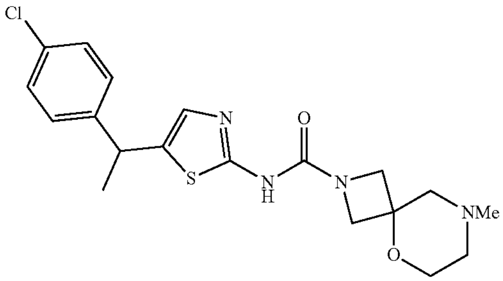 [SMILES: CC(c1ccc(Cl)cc1)c1cnc(NC(=O)N2CC3(CN(C)CCO3)C2)s1] Prepared by methylation of Example 133 using formaldehyde, $NaBH_3CN$, AcOH, MeOH, 40° C. | n/a | 407.1 |
| 135 | N-(5-(1-(4-chlorophenyl)ethyl)thiazol-2-yl)-3-(1,1-difluoroethyl)azetidine-1-carboxamide | 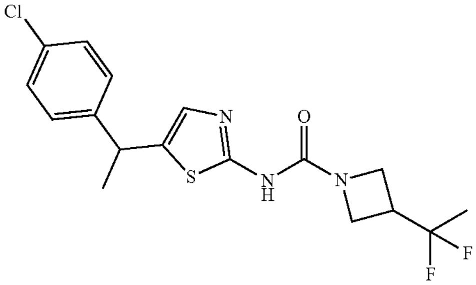 [SMILES: CC(c1ccc(Cl)cc1)c1cnc(NC(=O)N2CC(C(C)(F)F)C2)s1] An additional final difluorination step provided the title compound: 9 eq DAST, DCE, 0→20° C., 2 h. | 1-(azetidin-3-yl)ethan-1-one TFA salt | 386.1 |
| 136 | 3-fluoro-3-(methoxymethyl)-N-(5-(1-(4-(oxetan-3-ylcarbamoyl)phenyl)ethyl)thiazol-2-yl)azetidine-1-carboxamide | 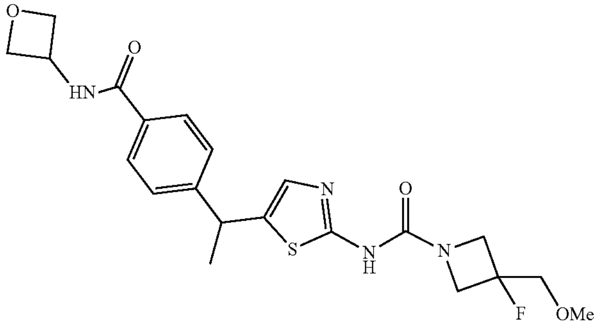 [SMILES: COCC1(F)CN(C(=O)Nc2ncc(C(C)c3ccc(C(=O)NC4COC4)cc3)s2)C1] | phenyl (5-(1-(4-(oxetan-3-ylcarbamoyl)phenyl)ethyl)thiazol-2-yl)carbamate | 449.2 |
| 137 | 5-(1-(2-(3-fluoro-3-(methoxymethyl)azetidine-1-carboxamido)thiazol-5-yl)ethyl)-N-(oxetan-3-yl)picolinamide | 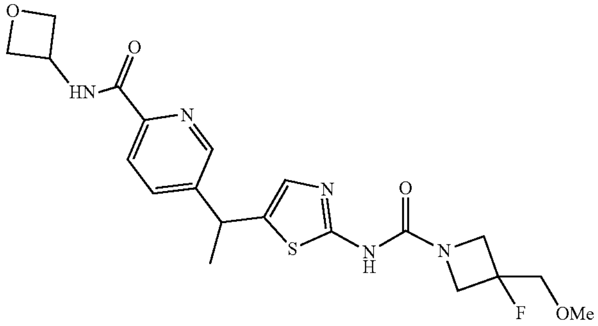 [SMILES: COCC1(F)CN(C(=O)Nc2ncc(C(C)c3ccc(C(=O)NC4COC4)nc3)s2)C1] | phenyl (5-(1-(6-(oxetan-3-ylcarbamoyl)pyridin-3-yl)ethyl)thiazol-2-yl)carbamate | 450.2 |

Synthetic Procedure G

Example 138: Oxazol-2-ylmethyl (5-(3-(4-aminobutoxy)benzyl)thiazol-2-yl)carbamate Step 1

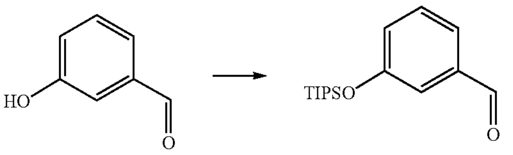

Triisopropylsilyl chloride (26.1 g, 135 mmol) was added dropwise to a solution of 3-hydroxybenzaldehyde (15 g, 123 mmol) and imidazole (18.4 g, 270 mmol) at 0° C. The reaction mixture was stirred at 0° C. for 30 min then at 25° C. for 90 min. The mixture was diluted with water (150 mL), then extracted into EtOAc (3×150 mL). The combined organic extracts were washed with brine (150 mL), dried over anhydrous sodium sulfate and then concentrated in vacuo. Purification by flash column chromatography on silica (EtOAc:PE, 0:1 to 1:19) afforded 3-((triisopropylsilyl)oxy)benzaldehyde (32.0 g, 94%) as a light yellow oil; ES-MS $[M+H]^+$ 279.1

Step 2

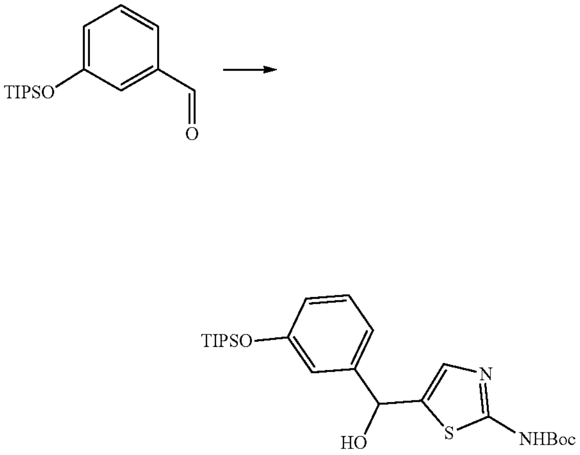

n-BuLi (2.5 M in THF, 74.9 mL, 150 mmol) was added dropwise to a solution of tert-butyl thiazol-2-ylcarbamate (15.0 g, 74.9 mmol) in THF (150 mL) at −60° C. and the resulting mixture was stirred at this temperature for 30 min. A solution of 3-((triisopropylsilyl)oxy)benzaldehyde (27.1 g, 97.4 mmol) in THF (50 mL) was added and stirring was continued at −60° C. for 2 h. The reaction mixture was quenched with saturated aqueous ammonium chloride solution (100 mL) and extracted into EtOAc (2×100 mL). The combined organic extracts were washed with brine (100 mL), dried over anhydrous sodium sulfate and then concentrated in vacuo. Flash column chromatography on silica (EtOAc:PE, 0:1 to 3:7) afforded tert-butyl (5-(hydroxy(3-((triisopropylsilyl)oxy)phenyl)methyl)thiazol-2-yl)carbamate (21.0 g, 58%) as a yellow oil; ES-MS $[M+H]^+$: 479.2.

Step 3

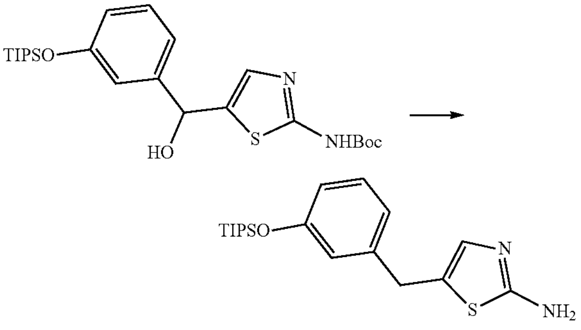

TFA (60.5 mL, 815 mmol) was added to a solution of tert-butyl (5-(hydroxy(3-((triisopropylsilyl)oxy)phenyl)methyl)thiazol-2-yl)carbamate (15.6 g, 32.6 mmol) and triethylsilane (26.0 mL, 163 mmol) in dichloromethane (150 mL) The resulting mixture was stirred at 25° C. for 2.5 h, then adjusted to pH 8 with saturated aqueous sodium bicarbonate solution and extracted into dichloromethane (2×100 mL). The combined organic extracts were washed with brine (100 mL), dried over anhydrous sodium sulfate and then concentrated in vacuo. Flash column chromatography on silica (EtOAc:PE, 0:1 to 3:7) afforded 5-(3-((triisopropylsilyl)oxy)benzyl)thiazol-2-amine (9.50 g, 80%) as a yellow oil; ES-MS $[M+H]^+$: 363.2.

Step 4

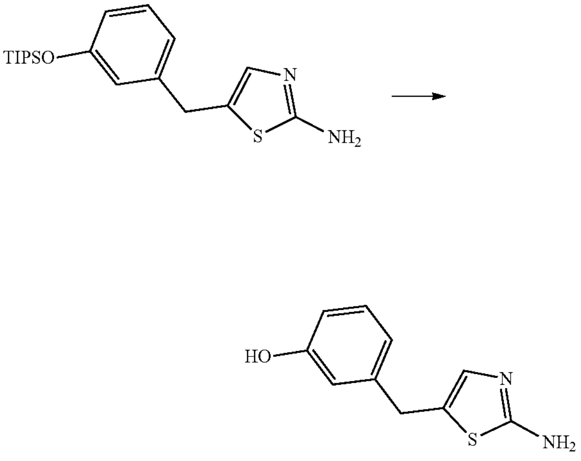

A mixture of 5-(3-((triisopropylsilyl)oxy)benzyl)thiazol-2-amine (5.00 g, 13.8 mmol) in TFA (35 mL) was stirred at 60° C. for 3 h, then adjusted to pH 8 with saturated aqueous sodium bicarbonate solution and extracted into EtOAc (2×50 mL). The combined organic extracts were washed with brine (100 mL), dried over anhydrous sodium sulfate and then concentrated in vacuo. Flash column chromatography on silica (EtOAc:PE, 0:1 to 7:3) afforded 3-((2-aminothiazol-5-yl)methyl)phenol (2.50 g, 12.1 mmol) as a yellow solid; ES-MS $[M+H]^+$: 207.0.

Step 5

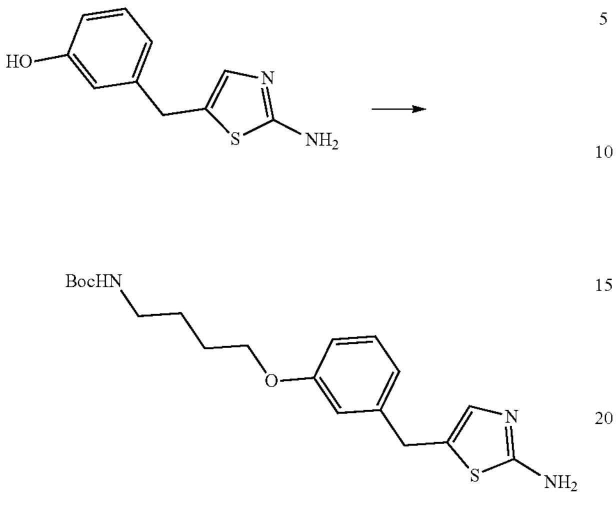

A solution of DIAD (1.47 g, 7.27 mmol) in THF (5 mL) was added to a mixture of 3-((2-aminothiazol-5-yl)methyl) phenol (1.00 g, 4.85 mmol), tert-butyl (4-hydroxybutyl) carbamate (1.38 g, 7.27 mmol) and triphenylphosphine (1.91 g, 7.27 mmol) in THF (20 mL) at 0° C. The reaction mixture was stirred at 25° C. for 12 h, then concentrated in vacuo and purified by flash column chromatography (EtOAc:PE, 0:1 to 7:3) to afford tert-butyl (4-(3-((2-aminothiazol-5-yl)methyl) phenoxy)butyl)carbamate (2.40 g, 66%) as a yellow oil; ES-MS $[M+H]^+$: 378.1.

Step 6

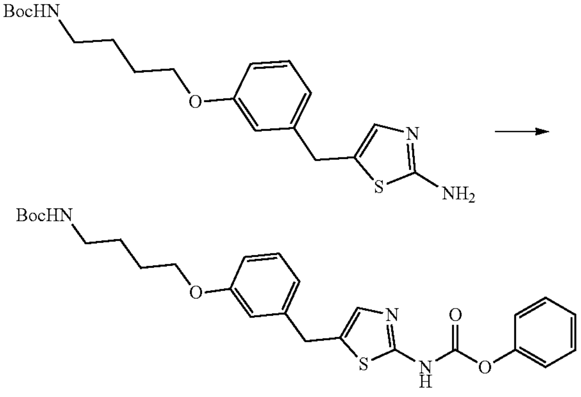

Phenyl chloroformate (0.60 mL, 4.82 mmol) was added to a solution of tert-butyl (4-(3-((2-aminothiazol-5-yl)methyl) phenoxy)butyl)carbamate (2.40 g, 3.21 mmol) and triethylamine (0.89 mL, 6.42 mmol) in THF (25 mL) at 0° C. The resulting mixture was stirred at 25° C. for 2 h, then diluted with water (15 mL) and extracted into EtOAc (2×15 mL). The combined organic extracts were washed with brine (15 mL), dried over anhydrous sodium sulfate and then concentrated in vacuo. Flash column chromatography on silica (EtOAc:PE, 0:1 to 3:7) afforded tert-butyl (4-(3-((2-((phenoxycarbonyl)amino)thiazol-5-yl)methyl)phenoxy)butyl) carbamate (1.1 g, 62%) as a white solid; ES-MS $[M+H]^+$: 498.2.

Step 7

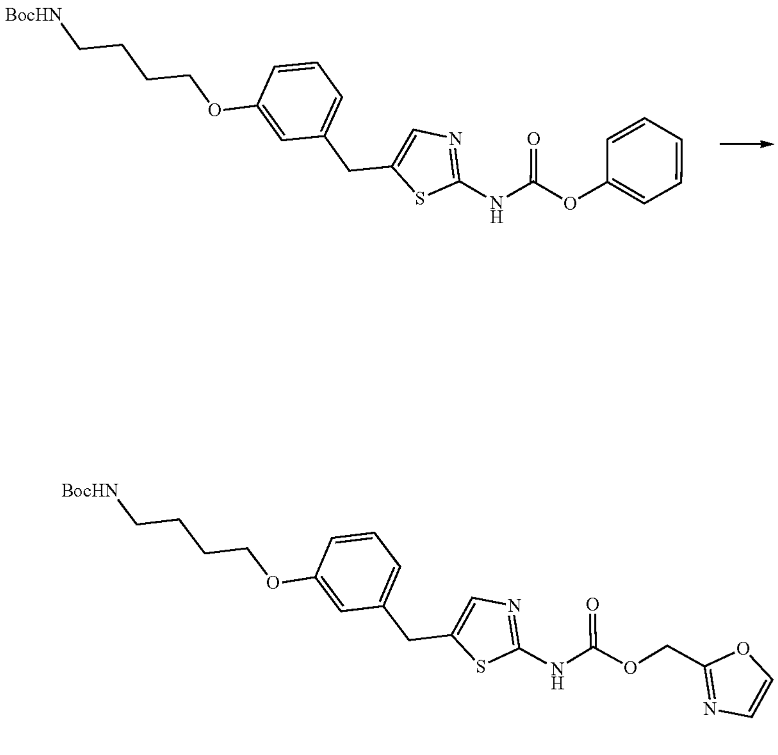

Sodium hydride (60% dispersion in oil, 97 mg, 2.43 mmol) was added to a solution of oxazol-2-ylmethanol (241 mg, 2.43 mmol) in THF (3 mL) at 0° C. The resulting mixture was stirred 0° C. for 30 min and then a solution of tert-butyl (4-(3-((2-((phenoxycarbonyl)amino)thiazol-5-yl)methyl)phenoxy)butyl)carbamate (1.10 g, 2.21 mmol) in THF (10 mL) was added. The reaction mixture was stirred at 20° C. for 12 h, then poured into saturated aqueous ammonium chloride solution (10 mL). The mixture was extracted into EtOAc (2×10 mL) and the combined organic extracts were washed with brine (10 mL) dried over anhydrous sodium sulfate and then concentrated in vacuo. Flash column chromatography on silica (EtOAc:PE, 0:1 to 4:1) afforded tert-butyl (4-(3-((2-(((oxazol-2-ylmethoxy)carbonyl)amino)thiazol-5-yl)methyl)phenoxy)butyl)carbamate (870 mg, 1.32 mmol) as a white solid; ES-MS [M+H]$^+$: 503.2.

Step 8

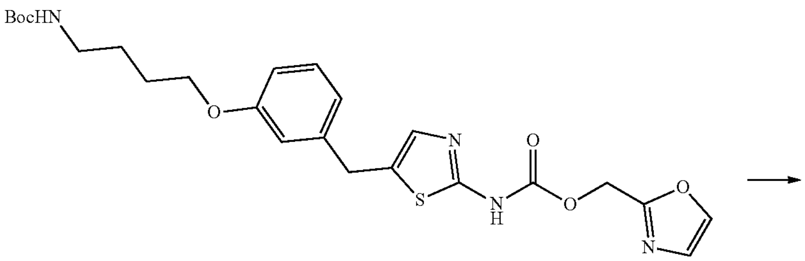

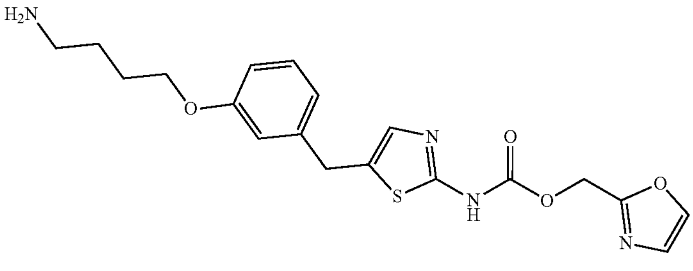

Hydrochloric acid (4.0 M in dioxane, 5 mL, 20 mmol) was added to tert-butyl (4-(3-((2-(((oxazol-2-ylmethoxy)carbonyl)amino)thiazol-5-yl)methyl)phenoxy)butyl)carbamate (470 mg, 0.94 mmol). The reaction mixture was stirred at 25° C. for 1 h, then concentrated in vacuo and purified by preparative HPLC (column: Waters™ XBridge BEH C18 OBD Prep Column, 130A, 10 m, 50 mm×150 mm; acetonitrile:[water (0.1% ammonium carbonate)]; gradient: 1:4→2:3) to afford oxazol-2-ylmethyl (5-(3-(4-aminobutoxy)benzyl)thiazol-2-yl)carbamate (32 mg, 7%) as a white solid; $\delta_H$ (400 MHz; $CD_3OD$) 7.94 (1H, s), 7.23-7.17 (2H, m), 7.06 (1H, s), 6.85-6.75 (3H, m), 5.29 (2H, s), 4.02 (2H, s), 3.98 (2H, m), 2.83-2.71 (2H, m), 1.85-1.77 (2H, m), 1.73-1.64 (2H, m); ES-MS $[M+H]^+$: 403.1.

Other examples prepared using synthetic procedure G are shown in the following table. All intermediates are commercially available unless noted (see ‘Intermediate synthesis’ section).

| Ex. No. | Name | Structure | Intermediates requiring synthesis | ES-MS $[M + H]^+$ |
|---|---|---|---|---|
| 139 | oxazol-2-ylmethyl (5-(3-(3-aminopropoxy)benzyl)thiazol-2-yl)carbamate | 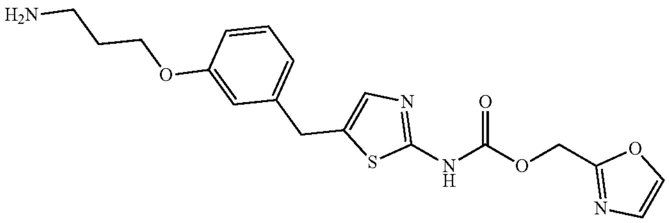 [SMILES: NCCCOc1cccc(Cc2cnc(NC(=O)OCc3ncco3)s2)c1] | n/a | 389.1 |
| 140 | oxazol-2-ylmethyl (5-(3-(2-aminoethoxy)benzyl)thiazol-2-yl)carbamate | 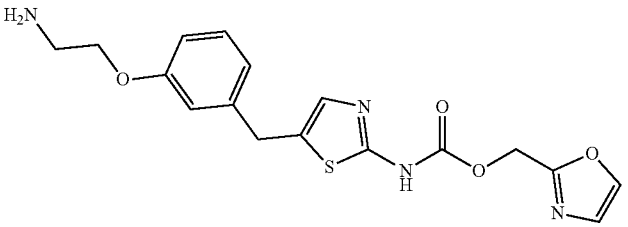 [SMILES: NCCOc1cccc(Cc2cnc(NC(=O)OCc3ncco3)s2)c1] | n/a | 375.2 |
| 141 | oxazol-2-ylmethyl (5-(3-(4-(dimethylamino)butoxy)benzyl)thiazol-2-yl)carbamate | 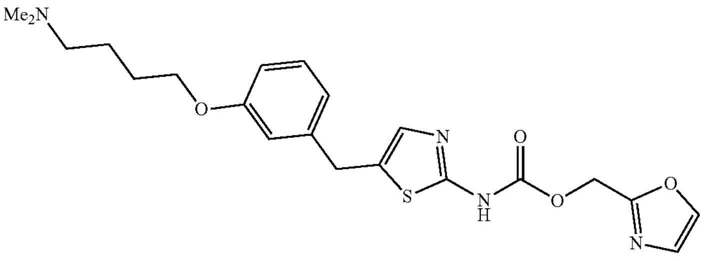 [SMILES: CN(C)CCCCOc1cccc(Cc2cnc(NC(=O)OCc3ncco3)s2)c1] Prepared by methylation of Example 140 using formaldehyde, $NaBH_3OAc$, AcOH, MeOH, 25° C. | n/a | 431.1 |
| 142 | oxazol-2-ylmethyl (5-(1-(4-chloro-3-(2-(dimethylamino)ethoxy)phenyl)ethyl)thiazol-2-yl)carbamate | 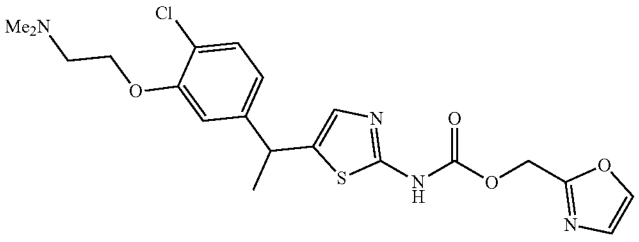 [SMILES: CC(c1ccc(Cl)c(OCCN(C)C)c1)c1cnc(NC(=O)OCc2ncco2)s1] Step 1 omitted. Step 2 used 1-(4-chloro-3-((triisopropylsilyl)oxy)phenyl)ethan-1-one. Additional final demethylation step in analogy to Example 141. | 1-(4-chloro-3-((triisopropylsilyl)oxy)phenyl)ethan-1-one | 451.2 |

-continued

| Ex. No. | Name | Structure | Intermediates requiring synthesis | ES-MS [M + H]+ |
|---|---|---|---|---|
| 143 | oxazol-2-ylmethyl (5-(4-chloro-3-(piperidin-4-yloxy)benzyl) thiazol-2-yl)carbamate | 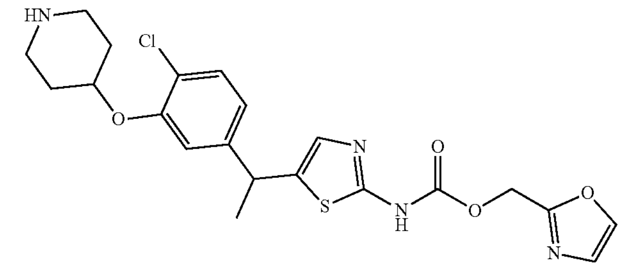 [SMILES: CC(c1ccc(Cl)c(OC2CCNCC2)c1)c1cnc(NC(=O)OCc2ncco2)s1] | n/a | 449.1 |
| 144 | oxazol-2-ylmethyl (5-(3-(azetidin-3-ylmethoxy)-4-chlorobenzyl) thiazol-2-yl)carbamate | 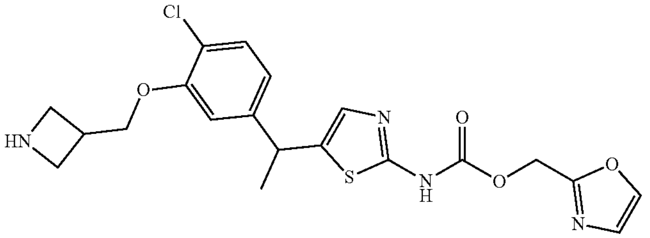 [SMILES: CC(c1ccc(Cl)c(OCC2CNC2)c1)c1cnc(NC(=O)OCc2ncco2)s1] | n/a | 435.1 |
| 145 | oxazol-2-ylmethyl (5-(3-(2-methoxyethoxy) benzyl) thiazol-2-yl)carbamate | 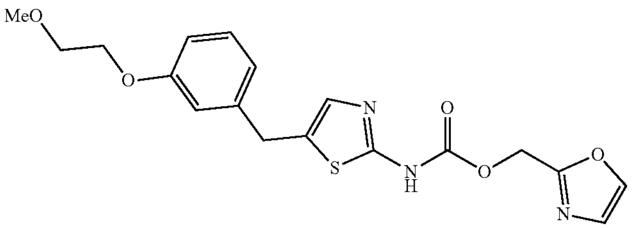 [SMILES: COCCOc1cccc(Cc2cnc(NC(=O)OCc3ncco3)s2)c1] Step 5 used 2-methoxyethan-1-ol. No Boc removal step | n/a | 390.2 |
| 146 | oxazol-2-ylmethyl (5-(4-chloro-3-(2-methoxyethoxy) benzyl)thiazol-2-yl)carbamate | 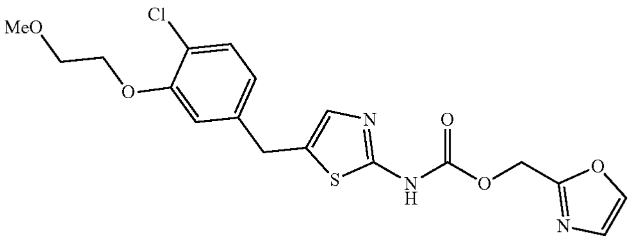 [SMILES: COCCOc1cc(Cc2cnc(NC(=O)OCc3ncco3)s2)ccc1Cl] Step 5 used 2-methoxyethan-1-ol. No Boc removal step | n/a | 424.1 |
| 147 | oxazol-2-ylmethyl (5-(1-(4-chloro-3-(2-methoxyethoxy) phenyl)ethyl) thiazol-2-yl)carbamate | 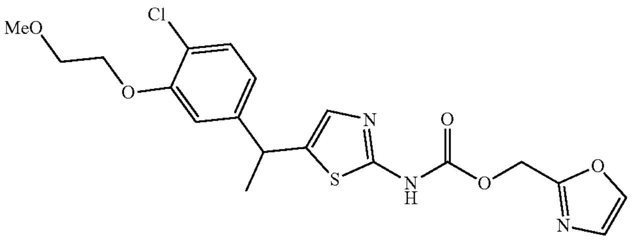 [SMILES: COCCOc1cc(C(C)c2cnc(NC(=O)OCc3ncco3)s2)ccc1Cl] Step 5 used 2-methoxyethan-1-ol. No Boc removal step | n/a | 438.0 |

-continued

| Ex. No. | Name | Structure | Intermediates requiring synthesis | ES-MS $[M + H]^+$ |
|---|---|---|---|---|
| 148 | oxazol-2-ylmethyl (5-(1-(4-chloro-3-(2-hydroxyethoxy)phenyl)ethyl)thiazol-2-yl)carbamate | 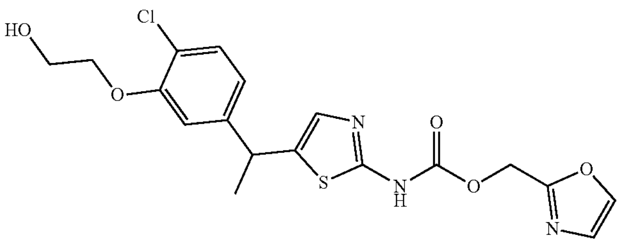 [SMILES: CC(c1ccc(Cl)c(OCCO)c1)c1cnc(NC(=O)OCc2ncco2)s1] Step 5 used TBS-protected starting material: 2-((tert-butyldimethylsilyl)oxy)ethan-1-ol. In the final step, modified conditions removed the TBS group to provide the title compound: 2M HCl in dioxane, $CH_2Cl_2$, 25° C., 1 h. | 1-(4-chloro-3-((triisopropylsilyl)oxy)phenyl)ethan-1-one | 424.0 |
| 149 | oxazol-2-ylmethyl (5-(4-chloro-3-(2-hydroxyethoxy)benzyl)thiazol-2-yl)carbamate | 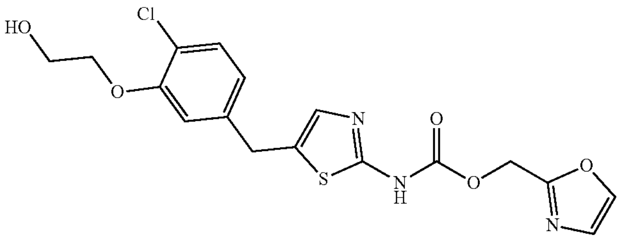 [SMILES: O=C(Nc1ncc(Cc2ccc(Cl)c(OCCO)c2)s1)OCc1ncco1] Prepared in analogous manner to Example 148 | n/a | 410.0 |
| 150 | oxazol-2-ylmethyl (5-(3-(3-aminopropoxy)-4-chlorobenzyl)thiazol-2-yl)carbamate | 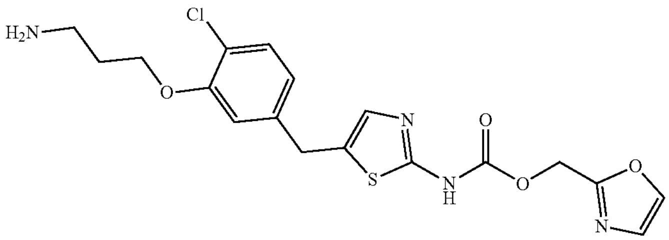 [SMILES: NCCCOc1cc(Cc2cnc(NC(=O)OCc3ncco3)s2)ccc1Cl] | n/a | 423.1 |
| 151 | oxazol-2-ylmethyl (5-(3-(3-acetamidopropoxy)-4-chlorobenzyl)thiazol-2-yl)carbamate | 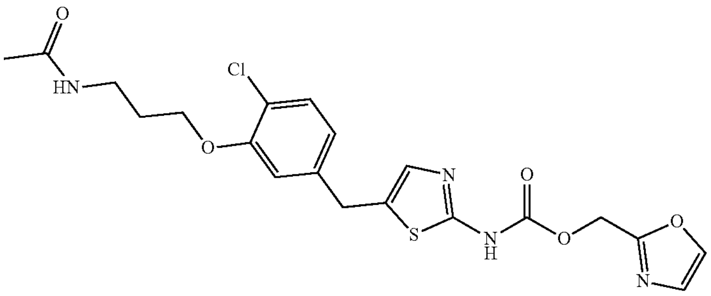 [SMILES: CC(=O)NCCCOc1cc(Cc2cnc(NC(=O)OCc3ncco3)s2)ccc1Cl] Prepared by acylation of Example 150 using $Ac_2O$, 25° C., 1 h. | n/a | 465.1 |

-continued

| Ex. No. | Name | Structure | Intermediates requiring synthesis | ES-MS $[M + H]^+$ |
|---|---|---|---|---|
| 152 | Oxazol-2-ylmethyl (5-(3-(piperidin-4-yloxy)benzyl)thiazol-2-yl)carbamate | 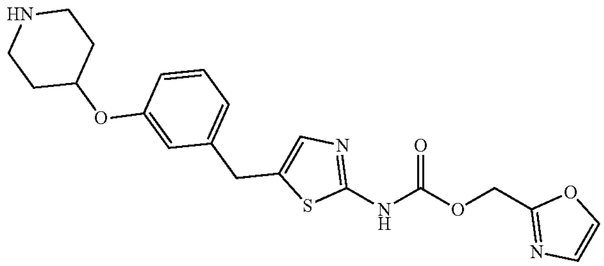 [SMILES: O=C(Nc1ncc(Cc2cccc(OC3CCNCC3)c2)s1)OCc1ncco1] | n/a | 415.2 |

Synthetic Procedure H

Example 153: Oxazol-2-ylmethyl (5-(4-chloro-3-((2-methoxyethyl)amino)benzyl)thiazol-2-yl)carbamate Step 1

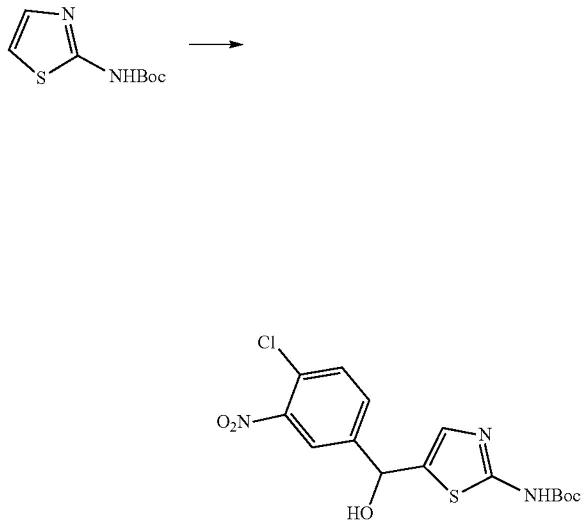

n-BuLi (2.5 M in THF, 74.9 mL, 187 mmol) was added dropwise to a solution of tert-butyl thiazol-2-ylcarbamate (15.0 g, 74.9 mmol) in THF (150 mL) at −60° C. and the resulting mixture was stirred at this temperature for 30 min. A solution of 4-chloro-3-nitrobenzaldehyde (20.9 g, 112 mmol) in THF (75 mL) was added and stirring was continued at −60° C. for 2 h. The reaction mixture was quenched with saturated aqueous ammonium chloride solution (200 mL) and extracted into EtOAc (3×300 mL). The combined organic extracts were washed with brine (300 mL), dried over anhydrous sodium sulfate and then concentrated in vacuo. Flash column chromatography on silica (EtOAc:PE, 0:1 to 2:3) afforded tert-butyl (5-((4-chloro-3-nitrophenyl)(hydroxy)methyl)thiazol-2-yl)carbamate (2.00 g, 40%) as a white solid; $\delta_H$ (400 MHz; DMSO-d6) 11.38 (1H, br s), 8.07 (1H, d, J 1.6 Hz), 7.81-7.65 (2H, m), 7.21 (1H, s), 6.54 (1H, d, J 4.4 Hz), 6.05 (1H, d, J 4.4 Hz), 1.44 (9H, s).

Step 2

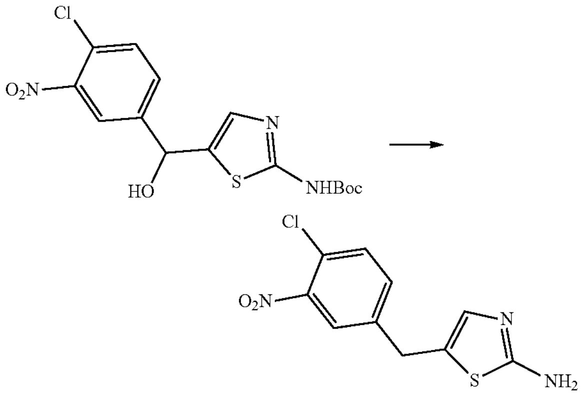

TFA (100 mL, 1.35 mmol) was added to a solution of tert-butyl (5-((4-chloro-3-nitrophenyl)(hydroxy)methyl)thiazol-2-yl)carbamate (20.0 g, 51.8 mmol) and triethylsilane (82.8 mL, 518 mmol) in dichloromethane (220 mL) The resulting mixture was stirred at 25° C. for 16 h, then adjusted to pH 7 with saturated aqueous sodium bicarbonate solution and extracted into EtOAc (3×400 mL). The combined organic extracts were washed with brine (400 mL), dried over anhydrous sodium sulfate and then concentrated in vacuo. Flash column chromatography on silica (EtOAc:PE, 0:1 to 1:0) afforded 5-(4-chloro-3-nitrobenzyl)thiazol-2-amine (5.20 g, 37%) as a yellow solid; $\delta_H$ (400 MHz; DMSO-d6) 7.93 (1H, d, J 2.0 Hz), 7.70 (1H, d, J 8.4 Hz), 7.56 (1H, m), 6.79 (2H, s), 6.76 (1H, s), 4.02 (2H, s).

Step 3

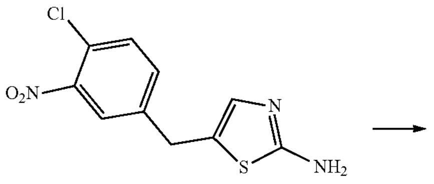

-continued

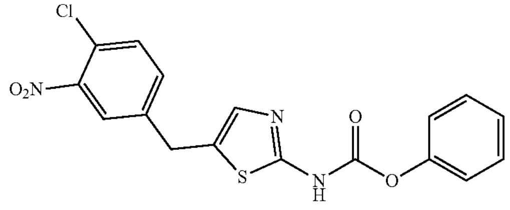

A solution of phenyl chloroformate (3.63 mL, 28.9 mmol) in THF (10 mL) was added to a solution of 5-(4-chloro-3-nitrobenzyl)thiazol-2-amine (5.20 g, 19.3 mmol) and pyridine (4.67 mL, 57.8 mmol) in THF (52 mL) at 0° C. The resulting mixture was stirred at 25° C. for 2 h, then diluted with water (50 mL) and extracted into EtOAc (3x50 mL). The combined organic extracts were washed with brine (50 mL), dried over anhydrous sodium sulfate and then concentrated in vacuo. Flash column chromatography on silica (EtOAc:PE, 0:1 to 1:0) afforded phenyl (5-(4-chloro-3-nitrobenzyl)thiazol-2-yl)carbamate (7.00 g, 93%) as a light yellow solid; ES-MS $[M+H]^+$: 390.0.

Step 4

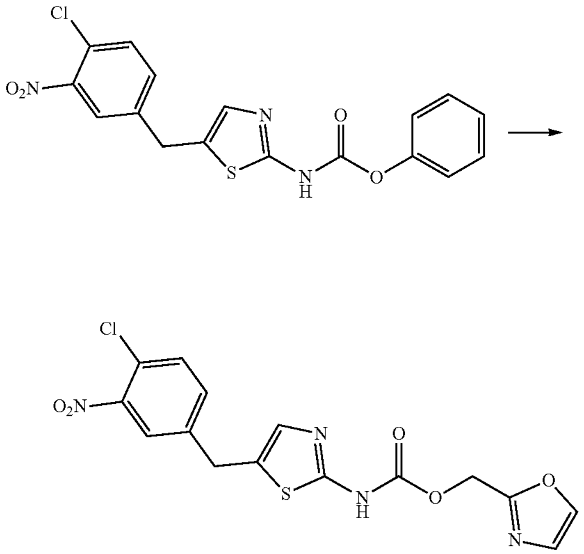

Sodium hydride (60% dispersion in oil, 1.44 g, 35.9 mmol) was added to a solution of oxazol-2-ylmethanol (2.67 g, 26.9 mmol) in THF (70 mL) at 0° C. The resulting mixture was stirred 0° C. for 30 min and then a solution of phenyl (5-(4-chloro-3-nitrobenzyl)thiazol-2-yl)carbamate (17.0 g, 47.8 mmol) in THF (30 mL) was added. The reaction mixture was stirred at 25° C. for 16 h, then quenched by addition of saturated aqueous ammonium chloride solution (50 mL) at 0° C. The mixture was extracted into EtOAc (3x70 mL) and the combined organic extracts were washed with brine (50 mL), dried over anhydrous sodium sulfate and then concentrated in vacuo. Flash column chromatography on silica (EtOAc:PE, 0:1 to 1:0) afforded oxazol-2-ylmethyl (5-(4-chloro-3-nitrobenzyl)thiazol-2-yl)carbamate (2.30 g, 5.83 mmol) as a yellow solid; ES-MS $[M+H]^+$: 395.0.

Step 5

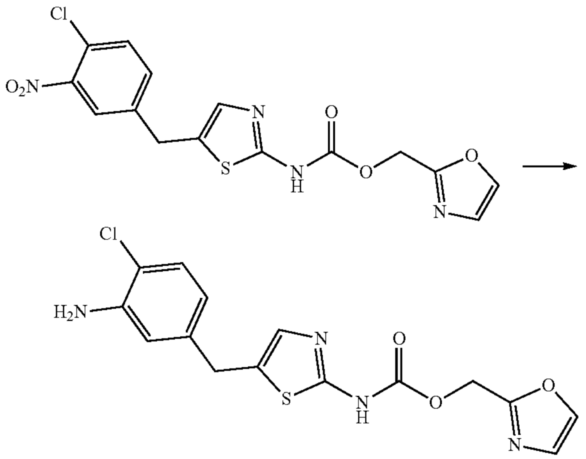

Iron (974 mg, 17.5 mmol) and ammonium chloride (1.56 g, 29.1 mmol) were added to a solution of oxazol-2-ylmethyl (5-(4-chloro-3-nitrobenzyl)thiazol-2-yl)carbamate (2.30 g, 5.83 mmol) in ethanol (46 mL) and water (8 mL). The reaction mixture was stirred at 60° C. for 3 h, then filtered and concentrated in vacuo. Water (30 mL) was added and the mixture was extracted into EtOAc (3x30 mL). The combined organic extracts were washed with brine (30 mL), dried over anhydrous sodium sulfate and then concentrated in vacuo. Trituration with EtOAc:PE (1:5, 10 mL) afforded oxazol-2-ylmethyl (5-(3-amino-4-chlorobenzyl)thiazol-2-yl)carbamate (1.30 g, 61%) as a yellow solid; ES-MS $[M+H]^+$: 365.0.

Step 6

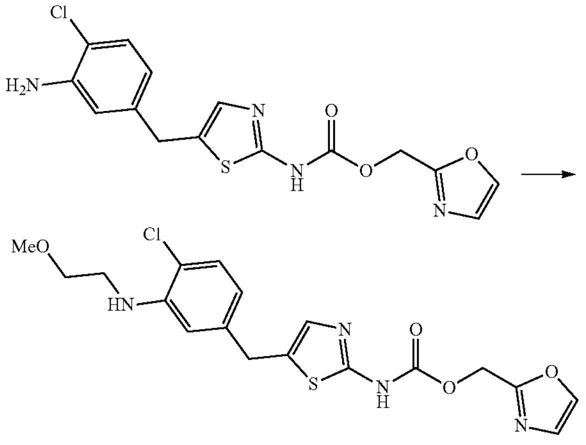

Acetic acid (16 μL, 0.27 mmol) was added to a solution of 2-methoxyacetaldehyde (81 mg, 1.10 mmol) and oxazol-2-ylmethyl (5-(3-amino-4-chlorobenzyl)thiazol-2-yl)carbamate (100 mg, 0.27 mmol) in methanol (10 mL). The reaction mixture was stirred at 25° C. for 16 h, then sodium cyanoborohydride (34 mg, 0.55 mmol) was added and stirring was continued for at the same temperature for 2 h. The mixture was concentrated in vacuo, diluted with water (15 mL) and extracted into EtOAc (3×15 mL). The combined organic extracts were washed with brine (15 mL), dried over anhydrous sodium sulfate and then concentrated in vacuo. Purification by preparative HPLC (column: Phenomenex Luna 10 μm C18 150×25 mm; acetonitrile:[water (0.1% formic acid)]; gradient: 41:59-71:29) afforded oxazol-2-ylmethyl (5-(4-chloro-3-((2-methoxyethyl)amino)benzyl) thiazol-2-yl)carbamate (52 mg, 450) as an off-white solid; $\delta_H$ (400 MHz; DMSO-d6) 11.87 (1H, br s), 8.15 (1H, s), 7.25 (1H, s), 7.19-7.14 (2H, m), 6.67 (1H, d, J 1.6 Hz), 6.47 (1H, m), 5.28 (2H, s), 5.14 (1H, m), 3.97 (2H, s), 3.50 (2H, m), 3.30-3.25 (5H, m); ES-MS $[M+H]^+$: 423.0.

Other examples prepared using synthetic procedure H are shown in the following table. All starting materials are commercially available.

| Ex. No. | Name | Structure | ES-MS $[M + H]^+$ |
| --- | --- | --- | --- |
| 154 | oxazol-2-ylmethyl (5-(1-(4-chloro-3-((2-methoxyethyl) amino)phenyl) ethyl)thiazol-2-yl)carbamate | 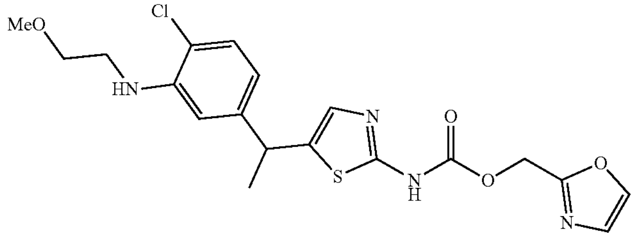 [SMILES: COCCNc1cc(C(C)c2cnc(NC(=O)OCc3ncco3)s2)ccc1Cl] | 437.1 |
| 155 | oxazol-2-ylmethyl (5-(3-((3-aminopropyl) amino)-4-chlorobenzyl) thiazol-2-yl)carbamate | 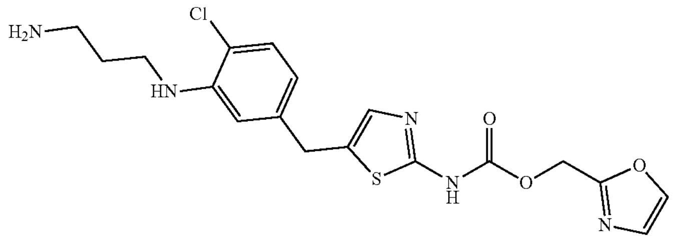 [SMILES: NCCCNc1cc(Cc2cnc(NC(=O)OCc3ncco3)s2)ccc1Cl] Boc-protected starting material was used: tert-butyl (3-oxopropyl)carbamate. A subsequent Boc-removal step provided the title compound: 2M HCl in dioxane, 25° C., 1 h. | 422.0 |
| 156 | oxazol-2-ylmethyl (5-(3-((4-aminobutyl) amino)benzyl) thiazol-2-yl)carbamate | 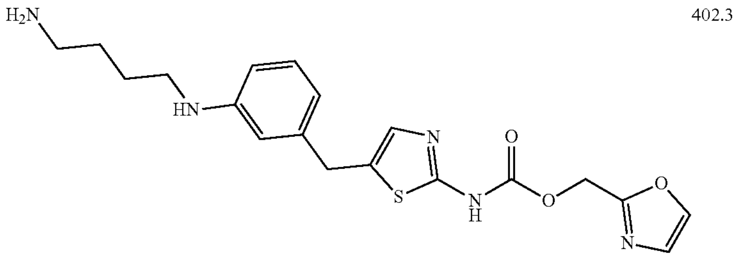 Boc-protected starting material was used: tert-butyl 2-hydroxy-1-pyrrolidinecarboxylate. A subsequent Boc-removal step provided the title compound: TFA (23 eq), $CH_2Cl_2$, 20° C., 1 h. | 402.3 |

Example 157: Oxazol-2-ylmethyl (7-phenyl-4,5,6,7-tetrahydrobenzo[d]thiazol-2-yl)carbamate Step 1

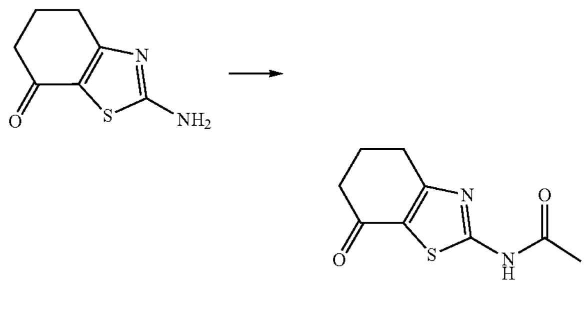

A solution of 2-amino-5,6-dihydrobenzo[d]thiazol-7(4H)-one (3.00 g, 17.9 mmol) in acetic anhydride (30 mL) was stirred at 80° C. for 2 h. The precipitate was collected by filtration and washed with THF (3x3 mL) to afford 2-amino-5,6-dihydrobenzo[d]thiazol-7(4H)-one (3.40 g, 91%) as a white solid; ES-MS $[M+H]^+$: 211.2.

Step 2

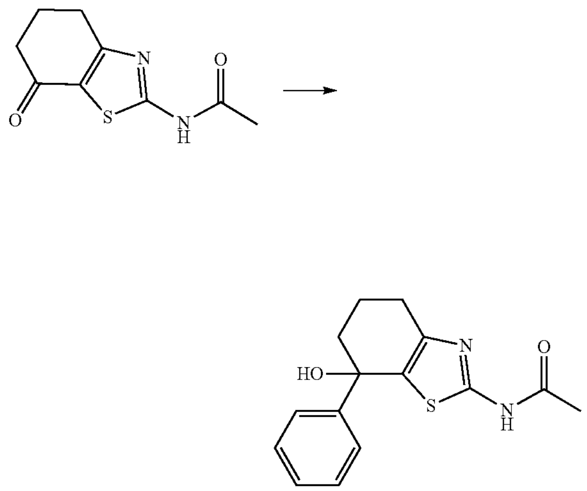

Phenylmagnesium bromide (3.0 M in THF, 7.61 mL, 22.8 mmol) was added to a solution of N-(7-oxo-4,5,6,7-tetrahydrobenzo[d]thiazol-2-yl)acetamide (2.40 g, 11.4 mmol) in THF (48 mL) at 0° C. The reaction mixture was stirred at 25° C. for 2 h, then quenched by addition of saturated aqueous ammonium chloride solution (30 mL) and extracted into EtOAc (3x30 mL). The combined organic extracts were washed with brine (30 mL), dried over anhydrous sodium sulfate and then concentrated in vacuo. Flash column chromatography on silica (EtOAc:PE, 0:1 to 19:1) afforded N-(7-hydroxy-7-phenyl-4,5,6,7-tetrahydrobenzo[d]thiazol-2-yl)acetamide (2.00 g, 61%) as a light yellow solid; ES-MS $[M+H]^+$: 289.1.

Step 3

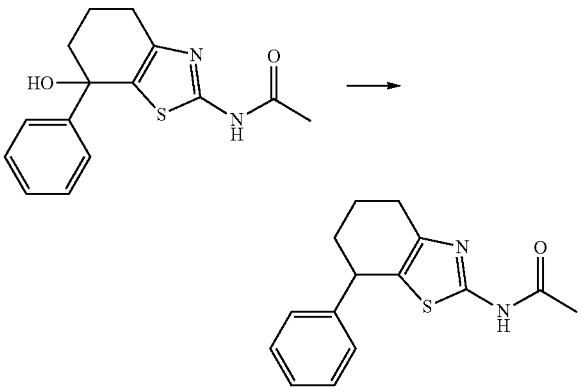

10% Pd/C (450 mg, 0.42 mmol) was added to a solution of N-(7-hydroxy-7-phenyl-4,5,6,7-tetrahydrobenzo[d]thiazol-2-yl)acetamide (1.50 g, 5.20 mmol) in methanol (50 mL) and TFA (5 mL). The reaction mixture was stirred under hydrogen (15 PSI) at 25° C. for 2 h, then filtered and concentrated in vacuo. Water (20 mL) was added and the mixture was extracted into EtOAc (3x20 mL). The combined organic extracts were washed with brine (20 mL), dried over anhydrous sodium sulfate and then concentrated in vacuo. Flash column chromatography on silica (EtOAc:PE, 0:1 to 7:3) to afford N-(7-phenyl-4,5,6,7-tetrahydrobenzo[d]thiazol-2-yl)acetamide (750 mg, 53%) as a light yellow solid; ES-MS $[M+H]^+$: 273.1.

Step 4

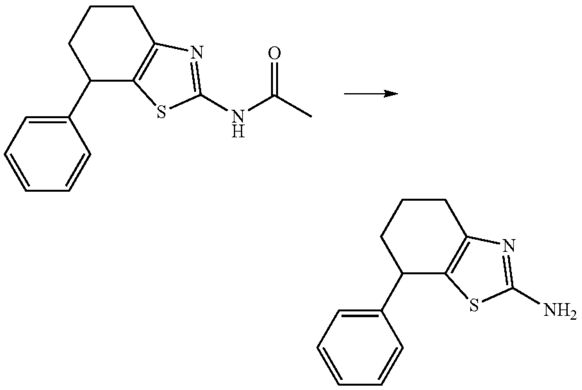

Hydrochloric acid (6.0 M in water, 1.38 mL, 8.28 mmol) was added to a solution of N-(7-phenyl-4,5,6,7-tetrahydrobenzo[d]thiazol-2-yl)acetamide (750 mg, 2.75 mmol) in ethanol (7.5 mL). The reaction mixture was stirred at 80° C. for 16 h, then concentrated in vacuo, diluted with water (15 mL) and washed with EtOAc (15 mL). The aqueous phase was adjusted to pH 7 with saturated aqueous sodium bicarbonate and extracted into EtOAc (3x15 mL). The combined organic extracts were washed with brine (15 mL), dried over anhydrous sodium sulfate and then concentrated in vacuo to afford 7-phenyl-4,5,6,7-tetrahydrobenzo[d]thiazol-2-amine (500 mg, 79%) as a yellow solid; ES-MS $[M+H]^+$: 231.2.

Step 5

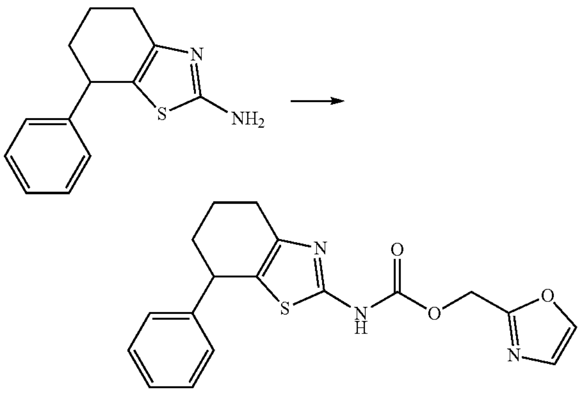

CDI (352 mg, 2.17 mmol) was added to a solution of oxazol-2-ylmethanol (215 mg, 2.17 mmol) in THF (2 mL) and the resulting mixture was stirred at 60° C. for 4 h. The mixture was then transferred to a solution of 7-phenyl-4,5,6,7-tetrahydrobenzo[d]thiazol-2-amine (100 mg, 0.43 mmol), triethylamine (0.30 mL, 2.17 mmol) and DMAP (5 mg, 0.04 mmol) in THF (2 mL) at 20° C. and stirred at 60° C. for 16 h. The mixture was cooled to 25° C. and the precipitate was filtered. Trituration with methanol:EtOAc (5:1, 5 mL) afforded oxazol-2-ylmethyl (7-phenyl-4,5,6,7-tetrahydrobenzo[d]thiazol-2-yl)carbamate (78 mg, 50%) as an off-white solid; $\delta_H$ (400 MHz; DMSO-d6) 11.84 (1H, br s), 8.15 (1H, d, J 0.8 Hz), 7.35-7.15 (6H, m), 5.32-5.17 (2H, m), 4.17-4.03 (1H, m), 2.70-2.55 (2H, m), 2.18-2.04 (1H, m), 1.95-1.81 (1H, m), 1.79-1.67 (2H, m); ES-MS $[M+H]^+$: 356.1.

Example 158: Oxazol-2-ylmethyl (6-phenyl-5,6-dihydro-4H-cyclopenta[d]thiazol-2-yl)carbamate Step 1

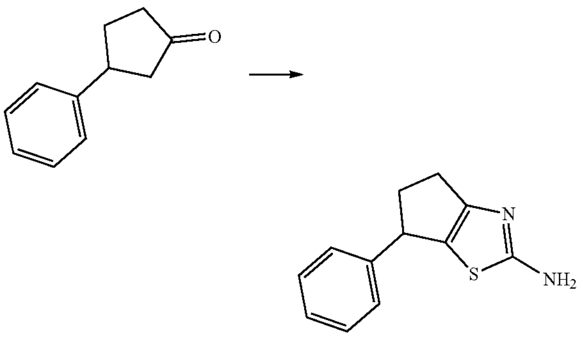

Bromine (1.06 mL, 20.6 mmol) was added to a solution of 3-phenylcyclopentan-1-one (3.00 g, 18.7 mmol) and thiourea (1.57 g, 20.6 mmol) in acetic acid (30 mL). The reaction mixture was stirred at 100° C. for 12 h, then basified to pH ~8 with saturated aqueous sodium bicarbonate solution and extracted into EtOAc (3x20 mL). The combined organic extracts were washed with brine (60 mL), dried over anhydrous sodium sulfate and then concentrated in vacuo. Flash column chromatography on silica (EtOAc:PE, 0:1 to 1:1) to afford 6-phenyl-5,6-dihydro-4H-cyclopenta[d]thiazol-2-amine (400 mg, 4%) as a yellow solid; ES-MS $[M+H]^+$: 217.1.

Step 2

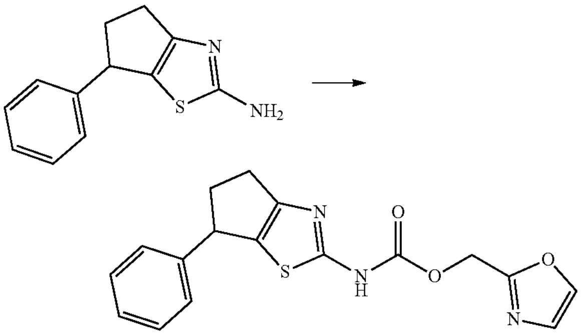

CDI (337 mg, 2.08 mmol) was added to a solution of oxazol-2-ylmethanol (206 mg, 2.08 mmol) in THF (4 mL) and the resulting mixture was stirred at 60° C. for 4 h. The mixture was then transferred to a solution of 6-phenyl-5,6-dihydro-4H-cyclopenta[d]thiazol-2-amine (200 mg, 0.42 mmol), triethylamine (0.29 mL, 2.08 mmol) and DMAP (5 mg, 0.04 mmol) in THF (2 mL) at 20° C. and stirred at 60° C. for 12 h. The reaction mixture was diluted with water (6 mL) and extracted into EtOAc (3x3 mL). The combined organic extracts were washed with brine (9 mL), dried over anhydrous sodium sulfate and then concentrated in vacuo. Purification by preparative HPLC (column: Phenomenex Luna 10 μm C18 150x25 mm; acetonitrile:[water (0.1% formic acid)]; gradient: 42:58→72:28) afforded oxazol-2-ylmethyl (6-phenyl-5,6-dihydro-4H-cyclopenta[d]thiazol-2-yl)carbamate (28 mg, 20%) as a white solid; ES-MS $[M+H]^+$: 342.1.

Example 159: Oxazol-2-ylmethyl (5-(3-((3-aminopropyl)thio)-4-chlorobenzyl)thiazol-2-yl)carbamate Step 1

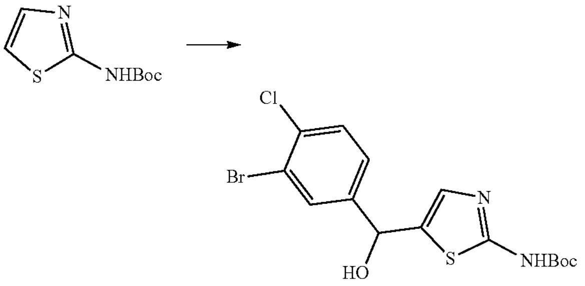

n-BuLi (2.5 M in THF, 45.0 mL, 112.5 mmol) was added dropwise to a solution of tert-butyl thiazol-2-ylcarbamate (10.0 g, 49.9 mmol) in THF (150 mL) at −65° C. and the resulting mixture was stirred at this temperature for 1 h. 3-Bromo-4-chlorobenzaldehyde (12.1 g, 55.1 mmol) in THF (10 mL) was added and stirring was continued at −65° C. for 1 h. The reaction mixture was quenched with saturated aqueous ammonium chloride solution (200 mL) and extracted into EtOAc (3×300 mL). The combined organic extracts were washed with brine (3×200 mL), dried over anhydrous sodium sulfate and then concentrated in vacuo. Flash column chromatography on silica (EtOAc:PE, 0:1 to 1:1) afforded tert-butyl (5-((3-bromo-4-chlorophenyl)(hydroxy)methyl)thiazol-2-yl)carbamate (14.0 g, 62%) as a white solid; ES-MS $[M+H]^+$: 421.0.

Step 2

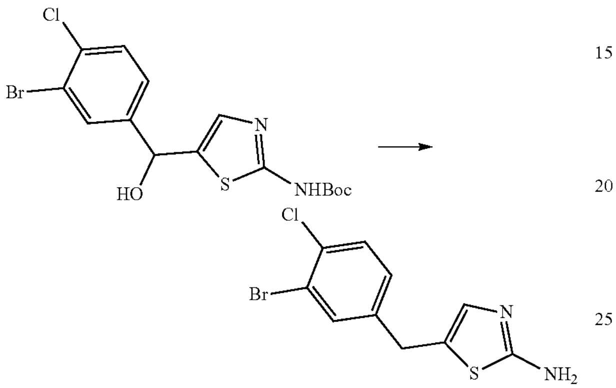

Triethylsilane (9.62 mL, 60.2 mmol) was added to a solution of tert-butyl (5-((3-bromo-4-chlorophenyl)(hydroxy)methyl)thiazol-2-yl)carbamate (5.00 g, 11.9 mmol) and TFA (12 mL, 162 mmol) in dichloromethane (36 mL). The resulting mixture was stirred at 25° C. for 4 h, then quenched by addition of saturated aqueous sodium bicarbonate solution (200 mL) and extracted into EtOAc (3×300 mL). The combined organic extracts were washed with brine (3×200 mL), dried over anhydrous sodium sulfate and then concentrated in vacuo. Flash column chromatography on silica (EtOAc:PE, 0:1 to 1:1) afforded 5-(3-bromo-4-chlorobenzyl)thiazol-2-amine (2.40 g, 60%) as a yellow oil; ES-MS $[M+H]^+$: 305.0.

Step 3

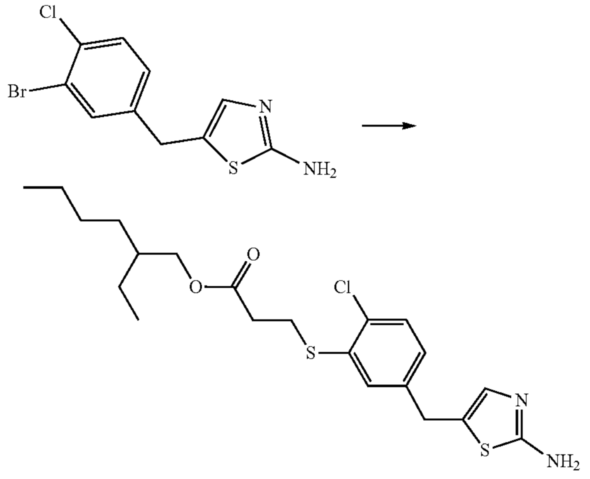

A mixture of 5-(3-bromo-4-chlorobenzyl)thiazol-2-amine (1.00 g, 3.29 mmol), 2-ethylhexyl 3-mercaptopropanoate (1.00 g, 4.58 mmol), XantPhos Pd G4 (320 mg, 0.33 mmol and triethylamine (1.50 mL, 10.8 mmol) in dioxane (15 mL) was stirred at 100° C. for 12 h. The reaction mixture was filtered, concentrated in vacuo and purified by flash column chromatography on silica (EtOAc:PE, 0:1 to 3:2) to afford 2-ethylhexyl 3-((5-((2-aminothiazol-5-yl)methyl)-2-chlorophenyl)thio)propanoate (1.30 g, 81%) as a yellow oil; ES-MS $[M+H]^+$: 441.2.

Step 4

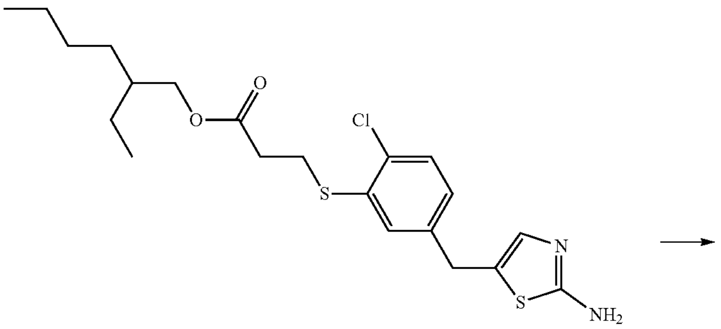

-continued

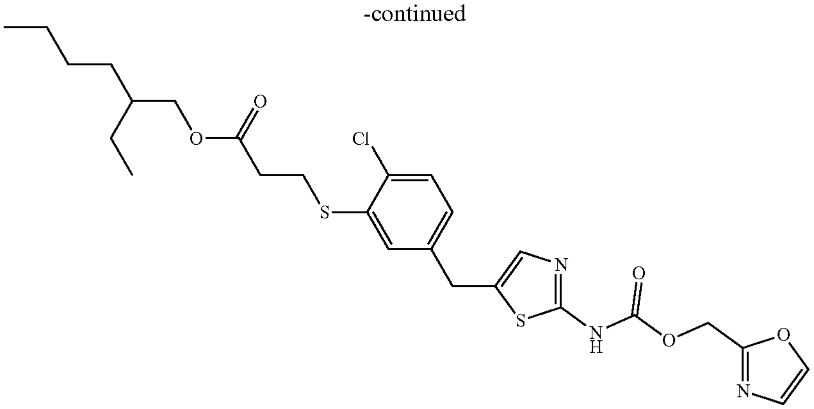

CDI (370 mg, 2.28 mmol) was added to a solution of oxazol-2-ylmethanol (220 mg, 2.22 mmol) in THF (5 mL) and the resulting mixture was stirred at 60° C. for 4 h. 2-Ethylhexyl 3-((5-((2-aminothiazol-5-yl)methyl)-2-chlorophenyl)thio)propanoate (200 mg, 0.45 mmol), triethylamine (0.30 mL, 2.16 mmol) and DMAP (10 mg, 0.08 mmol) were then added at 20° C. and stirring was continued at 60° C. for 12 h. The reaction mixture was concentrated in vacuo and purified by flash column chromatography on silica (EtOAc:PE, 0:1 to 1:1) to afford 2-ethylhexyl 3-((2-chloro-5-((2-(((oxazol-2-ylmethoxy)carbonyl)amino)thiazol-5-yl)methyl)phenyl)thio)propanoate (120 mg, 44%) as a yellow oil; ES-MS $[M+H]^+$: 566.3.

Step 5

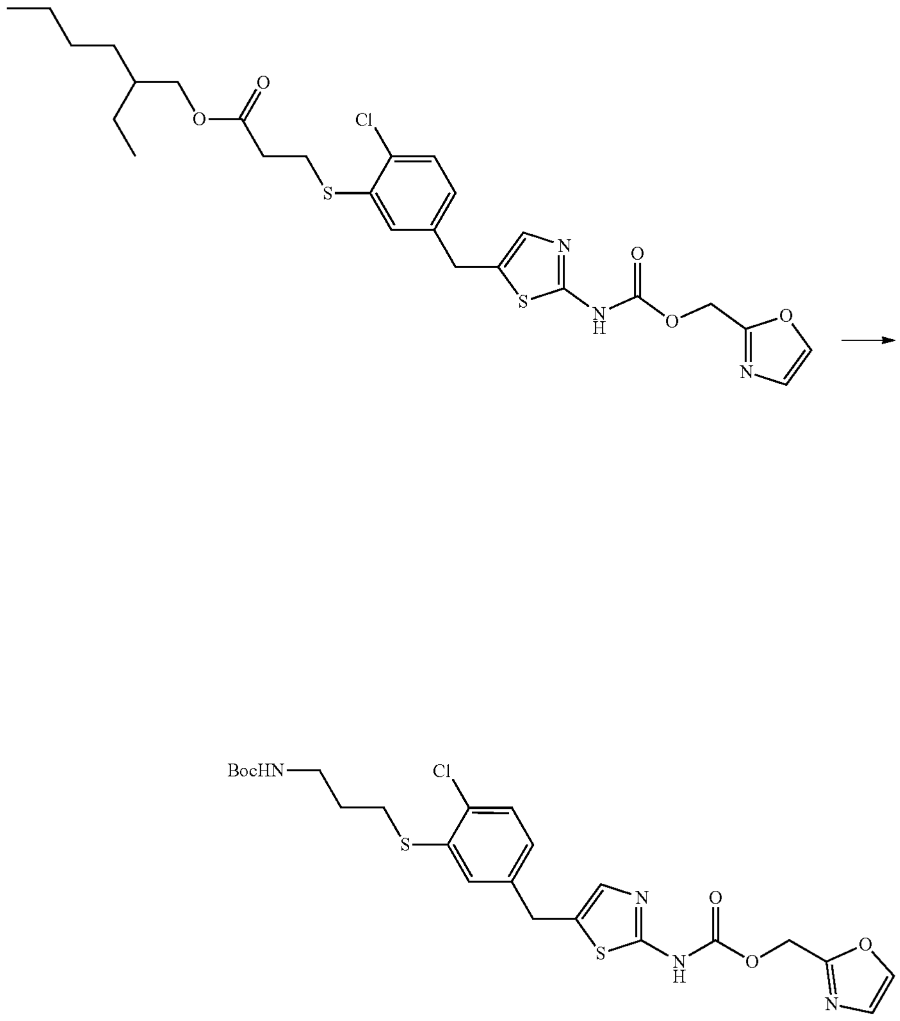

Sodium ethoxide (0.30 g, 0.88 mmol) was added to a solution of 2-ethylhexyl 3-((2-chloro-5-((2-(((oxazol-2-ylmethoxy)carbonyl)amino)thiazol-5-yl)methyl)phenyl)thio) propanoate (120 mg, 0.21 mmol) in ethanol (1 mL) at 0° C. The reaction mixture was stirred at 25° C. for 1 h and then tert-butyl (3-bromopropyl)carbamate (60 mg, 0.25 mmol) was added and stirring continued at this temperature for another 2 h. Water (20 mL) was added and the mixture was extracted into EtOAc (3×30 mL). The combined organic extracts were washed with brine (3×20 mL), dried over anhydrous sodium sulfate and then concentrated in vacuo to afford oxazol-2-ylmethyl (5-(3-((3-((tert-butoxycarbonyl)amino)propyl)thio)-4-chlorobenzyl)thiazol-2-yl)carbamate (100 mg, crude) as a yellow gum; ES-MS $[M+H]^+$: 540.2.

Step 6

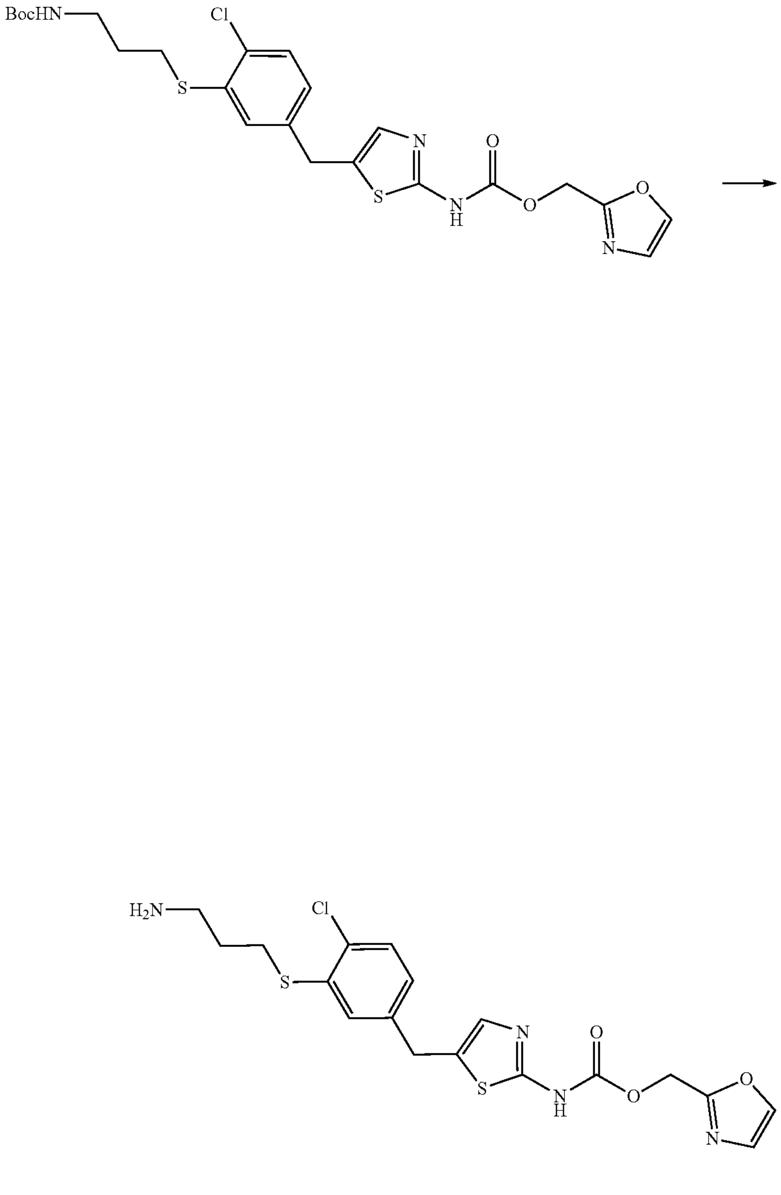

Hydrochloric acid (2.0 M in dioxane, 0.50 mL, 1 mmol) was added to a solution of oxazol-2-ylmethyl (5-(3-((3-((tert-butoxycarbonyl)amino)propyl)thio)-4-chlorobenzyl)thiazol-2-yl)carbamate (80 mg, 0.15 mmol) in dioxane (1 mL). The reaction mixture was stirred at 25° C. for 12 h, then concentrated in vacuo and purified by preparative HPLC (column: Phenomenex Luna 10 μm C18 150×25 mm; acetonitrile:[water (0.1% formic acid)]; gradient: 12:88→42:58) to afford oxazol-2-ylmethyl (5-(3-((3-aminopropyl)thio)-4-chlorobenzyl)thiazol-2-yl)carbamate (10 mg, 14%) as a white solid; $\delta_H$ (400 MHz; DMSO-d6) 8.17-8.14 (1H, m), 7.42-7.37 (1H, m), 7.35-7.29 (1H, m), 7.26-7.24 (1H, m), 7.22-7.15 (1H, m), 7.10-7.03 (1H, m), 5.29-5.23 (2H, m), 4.10-4.04 (2H, m), 3.10-3.03 (2H, m), 2.92-2.80 (2H, m), 1.89-1.76 (2H, m); ES-MS $[M+H]^+$: 439.1.

Example 160: Oxazol-2-ylmethyl (5-(3-(3-aminopropylsulfonimidoyl)-4-chlorobenzyl)thiazol-2-yl)carbamate Step 1

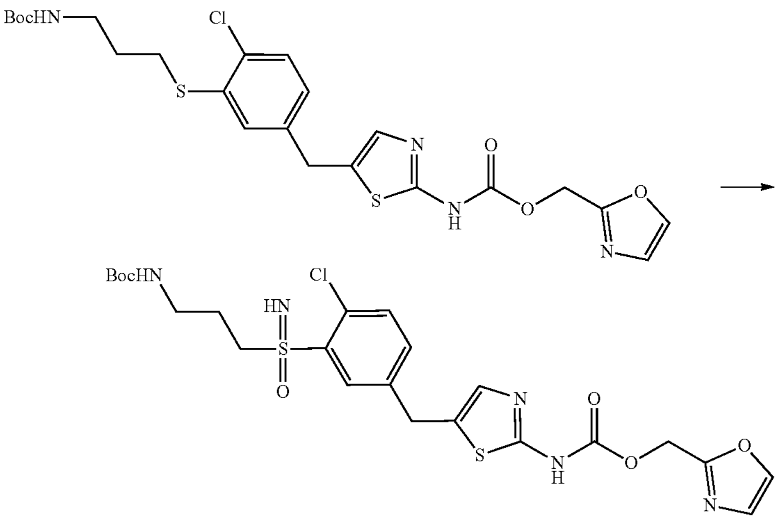

Ammonium carbonate (41 mg, 0.52 mmol) and (diacetoxyiodo)benzene (81 mg, 0.25 mmol) were added to a solution of oxazol-2-ylmethyl (5-(3-((3-((tert-butoxycarbonyl)amino)propyl)thio)-4-chlorobenzyl)thiazol-2-yl)carbamate* (50 mg, 0.09 mmol) in methanol (1 mL). The reaction mixture was stirred at 25° C. for 12 h, then concentrated in vacuo to afford oxazol-2-ylmethyl (5-(3-(3-((tert-butoxycarbonyl)amino)propylsulfonimidoyl)-4-chlorobenzyl)thiazol-2-yl)carbamate (50 mg, crude); ES-MS $[M+H]^+$: 570.3.

*see Step 5 of Example 159

Step 2

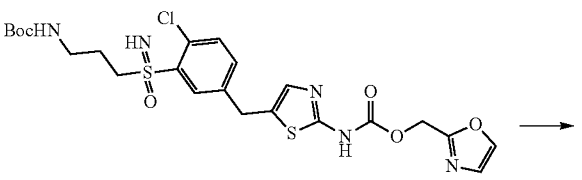

-continued

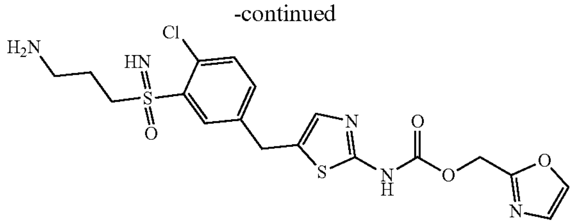

Hydrochloric acid (2.0 M in dioxane, 0.20 mL, 0.40 mmol) was added to a solution of oxazol-2-ylmethyl (5-(3-(3-((tert-butoxycarbonyl)amino)propylsulfonimidoyl)-4-chlorobenzyl)thiazol-2-yl)carbamate (40 mg, 0.070 mmol) in methanol (1 mL). The reaction mixture was stirred at 25° C. for 2 h, then concentrated in vacuo and purified by preparative HPLC (column: Phenomenex Luna 10 μm C18 150×25 mm; acetonitrile:[water (0.1% formic acid)]; gradient: 34:66→64:36) to afford oxazol-2-ylmethyl (5-(3-(3-aminopropylsulfonimidoyl)-4-chlorobenzyl)thiazol-2-yl)carbamate (8 mg, 24%) as a white solid; $\delta_H$ (400 MHz; DMSO-d6) 8.40-8.30 (1H, m), 8.06 (1H, d, J 0.7 Hz), 7.91 (1H, d, J 2.0 Hz), 7.63-7.57 (1H, m), 7.54 (1H, br d, J 2.1 Hz), 7.20 (2H, d, J 3.5 Hz), 5.24 (2H, s), 4.14 (2H, s), 3.44 (2H, m), 2.85 (2H, m), 1.90-1.75 (2H, m); ES-MS $[M+H]^+$: 470.1.

Example 161: Oxazol-2-ylmethyl (5-(4-chlorobenzyl)-4-(methoxymethyl)thiazol-2-yl)carbamate Step 1

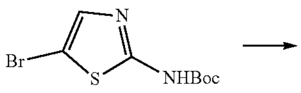

-continued

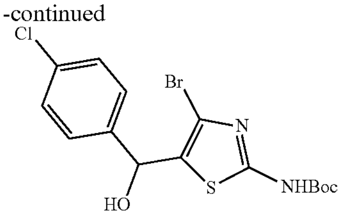

LDA (2.0 M in THF, 30.0 mL, 60.0 mmol) was added to a solution of tert-butyl (5-bromothiazol-2-yl)carbamate (45.0 g, 225 mmol) in THF (50 mL) at −70° C. and the resulting mixture was stirred for 30 min at this temperature. 4-Chlorobenzaldehyde (8.31 g, 59.1 mmol) was then added at −70° C. and stirring was continued at 25° C. for 2 h. The reaction mixture was quenched by addition of saturated aqueous ammonium chloride solution (200 mL) at 0° C. and extracted into EtOAc (3×200 mL). The combined organic extracts were dried over anhydrous sodium sulfate and concentrated in vacuo. Flash column chromatography on silica (EtOAc:PE, 1:10 to 1:1), followed by purification by preparative HPLC (column: Phenomenex Luna 15 μm C18 150×40 mm; acetonitrile:[water (0.1% formic acid)]; gradient: 60:40→90:10) afforded tert-butyl (4-bromo-5-((4-chlorophenyl)(hydroxy)methyl)thiazol-2-yl)carbamate (2.00 g, 27%) as an off-white solid; $\delta_H$ (400 MHz; $CDCl_3$) 7.45-7.39 (2H, m), 7.37-7.30 (2H, m), 6.06 (1H, s), 2.01 (1H, s), 1.52 (9H, s).

Step 2

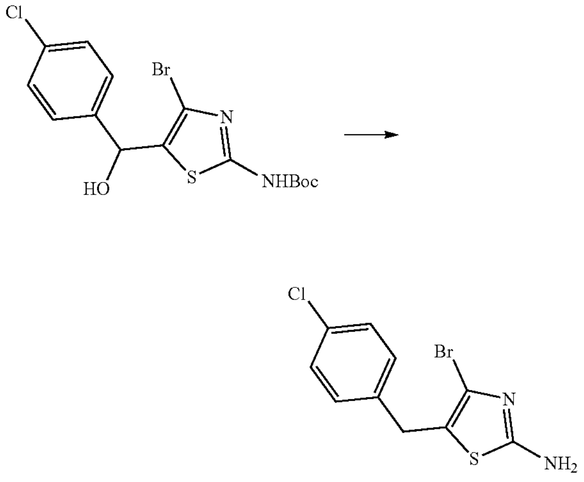

Triethylsilane (1.00 mL, 6.26 mmol) was added to a solution of tert-butyl (4-bromo-5-((4-chlorophenyl)(hydroxy)methyl)thiazol-2-yl)carbamate (200 mg, 0.48 mmol) in TFA (2 mL) and dichloromethane (2 mL). The reaction mixture was stirred at 25° C. for 1 h, then diluted with water (50 mL) and extracted into EtOAc (3×100 mL). The combined organic extracts were washed with brine (50 mL), dried over anhydrous sodium sulfate and then concentrated in vacuo. Flash column chromatography on silica (EtOAc:PE, 0:1 to 1:4) afforded 4-bromo-5-(4-chlorobenzyl)thiazol-2-amine (140 mg, 85%) as a colorless oil; ES-MS $[M+H]^+$: 305.1.

Step 3

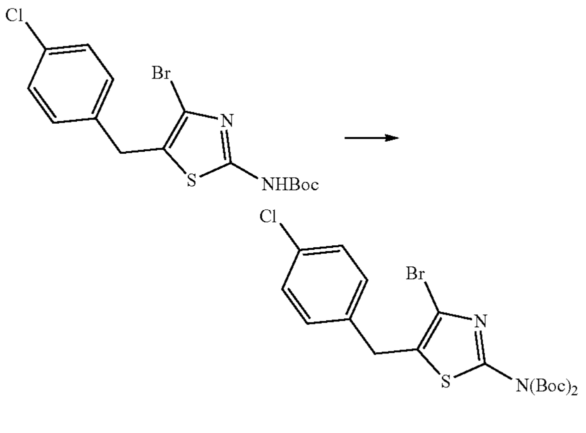

Di-tert-butyl dicarbonate (719 mg, 3.29 mmol) was added to a solution of 4-bromo-5-(4-chlorobenzyl)thiazol-2-amine (500 mg, 1.65 mmol), DMAP (20 mg, 0.16 mmol) and DIPEA (0.86 mL, 4.94 mmol) in dichloromethane (5 mL). The reaction mixture was stirred at 25° C. for 2 h, then diluted with water (50 mL) and extracted into EtOAc (3×50 mL). The combined organics were washed with brine (50 mL), dried over anhydrous sodium sulfate and then concentrated in vacuo. Flash column chromatography on silica (EtOAc:PE, 0:1 to 1:4) afforded di-tert-butyl (4-bromo-5-(4-chlorobenzyl)thiazol-2-yl)iminodicarbonate (350 mg, 42%) as a white solid; ES-MS $[M+H]^+$: 505.1.

Step 4

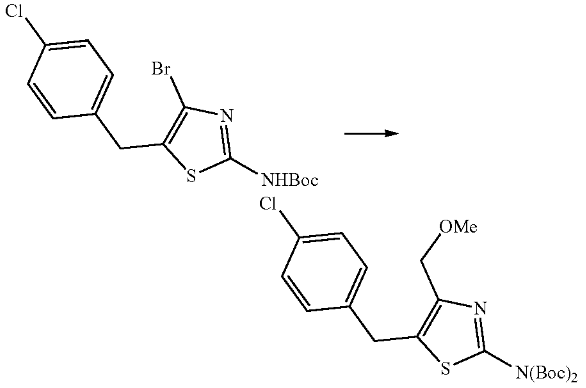

Potassium (Methoxymethyl)trifluoroborate (450 mg, 2.96 mmol) was added to a mixture of di-tert-butyl (4-bromo-5-(4-chlorobenzyl)thiazol-2-yl)iminodicarbonate (300 mg, 0.60 mmol), $Pd(dppf)Cl_2$ (60 mg, 0.08 mmol), sodium carbonate (180 mg, 1.70 mmol) and water (0.6 mL) in dioxane (3 mL). The reaction mixture was stirred at 80° C. for 3 h, then concentrated in vacuo and purified by flash column chromatography on silica (EtOAc:PE, 0:1 to 1:4) to afford di-tert-butyl (5-(4-chlorobenzyl)-4-(methoxymethyl)thiazol-2-yl)iminodicarbonate (160 mg, 36%) as a yellow oil; ES-MS $[M-Boc+H]^+$: 369.0.

Step 5

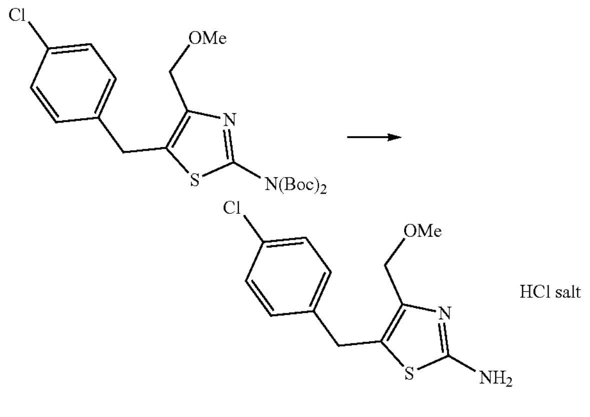

Hydrochloric acid (2.0 M, 2 mL, 4.00 mmol) was added to di-tert-butyl (5-(4-chlorobenzyl)-4-(methoxymethyl)thiazol-2-yl)iminodicarbonate (150 mg, 0.32 mmol) and the resulting mixture was stirred at 60° C. for 12 h, then concentrated in vacuo to afford 5-(4-chlorobenzyl)-4-(methoxymethyl)thiazol-2-amine HCl salt (80 mg, crude) as a yellow oil; ES-MS $[M+H]^+$: 269.1.

Step 6

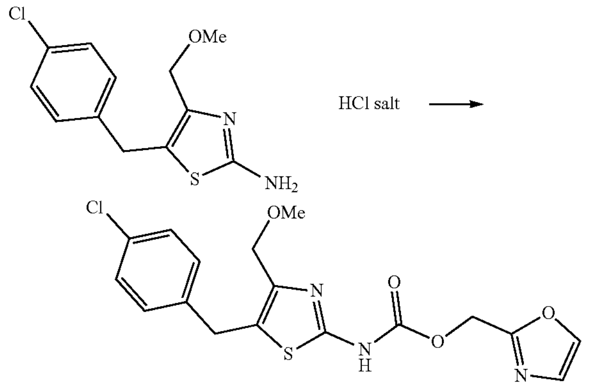

CDI (240 mg, 1.48 mmol) was added to a solution of 5-(4-chlorobenzyl)-4-(methoxymethyl)thiazol-2-amine HCl salt (80 mg, 0.30 mmol) in THF (2 mL) at 0° C. and the resulting mixture was stirred at 60° C. for 1 h. Oxazol-2-ylmethanol (140 mg, 1.41 mmol), triethylamine (0.20 mL, 1.44 mmol) and DMAP (10 mg, 0.08 mmol) were then added at 20° C. and stirring was continued at 60° C. for 2 h. The reaction mixture was diluted with water (50 mL) and extracted into EtOAc (3×50 mL). The combined organic extracts were washed with brine (3×50 mL), dried over anhydrous sodium sulfate and concentrated in vacuo. Purification by preparative HPLC (column: Phenomenex Luna 10 μm C18 150×25 mm; acetonitrile:[water (0.1% formic acid)]; gradient: 38:62→68:32) afforded oxazol-2-ylmethyl (5-(4-chlorobenzyl)-4-(methoxymethyl)thiazol-2-yl)carbamate (13 mg, 11%) as a white solid; $\delta_H$ (400 MHz; $CD_3OD$) 7.94 (1H, s), 7.33-7.27 (2H, m), 7.26-7.19 (3H, m), 5.30 (2H, s), 4.42 (2H, s), 4.11 (2H, s), 3.35 (3H, s); ES-MS $[M+H]^+$: 394.1.

Example 162: Oxazol-2-ylmethyl (5-((4-chlorophenyl)(methoxy)methyl)thiazol-2-yl)carbamate Step 1

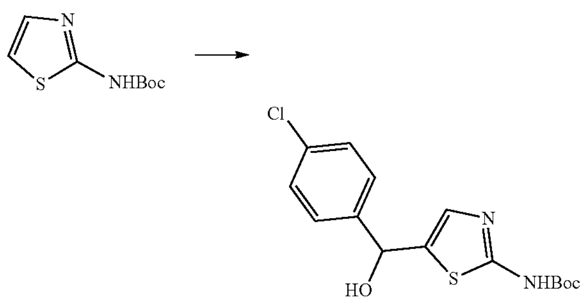

n-BuLi (2.5 M in THF, 10.0 mL, 25.0 mmol) was added dropwise to a solution of tert-butyl thiazol-2-ylcarbamate (2.00 g, 9.99 mmol) in THF (20 mL) at −60° C. and the resulting mixture was stirred at this temperature for 1 h. 4-Chlorobenzaldehyde (2.20 g, 15.7 mmol) was then added and stirring was continued at −60° C. for 1 h. The reaction mixture was quenched with saturated aqueous ammonium chloride solution (50 mL) and extracted into EtOAc (3×50 mL). The combined organic extracts were dried over anhydrous sodium sulfate and then concentrated in vacuo. Flash column chromatography on silica (EtOAc:PE, 3:7 to 1:1) afforded tert-butyl (5-((4-chlorophenyl)(hydroxy)methyl)thiazol-2-yl)carbamate (2.20 g, 65%) as a white solid; ES-MS $[M+H]^+$: 341.0.

Step 2

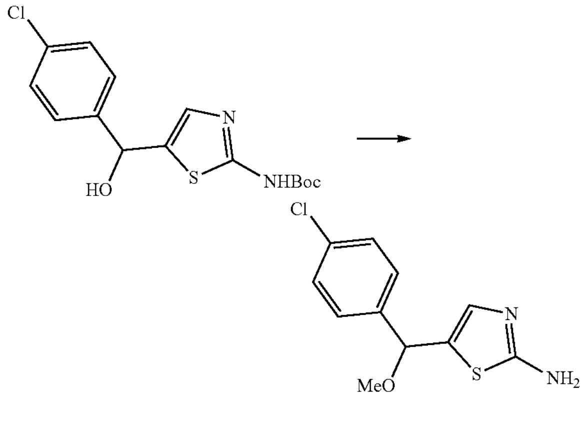

TFA (1.50 mL, 20.2 mmol) was added to a solution of tert-butyl (5-((4-chlorophenyl)(hydroxy)methyl)thiazol-2-yl)carbamate (300 mg, 0.88 mmol) in dichloromethane (1.5 mL) and the resulting mixture was stirred at 25° C. for 1 h. Methanol (1.50 mL, 37.1 mmol) was added and stirring was continued at 25° C. for another 1 h. Concentration in vacuo afforded 5-((4-chlorophenyl)(methoxy)methyl)thiazol-2-amine TFA salt (200 mg, crude) as a yellow oil; ES-MS $[M+H]^+$: 255.1.

Step 3

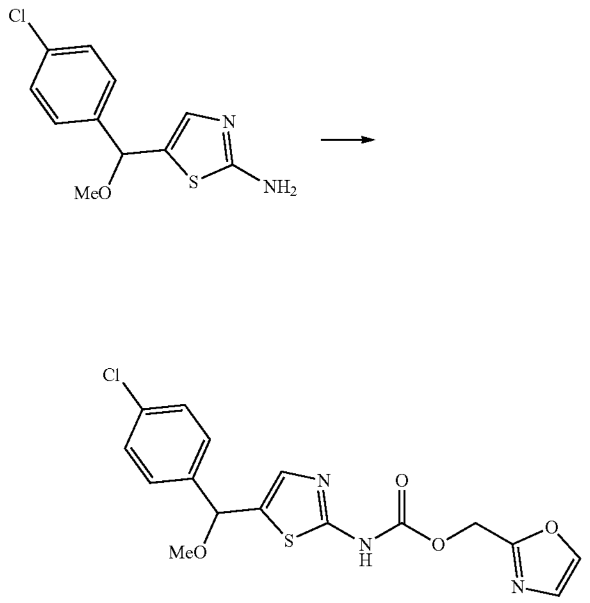

CDI (190 mg, 1.17 mmol) was added to a solution of oxazol-2-ylmethanol (120 mg, 1.21 mmol) in THF (2 mL) at 25° C. and the resulting mixture was stirred at 60° C. for 2 h. 5-((4-Chlorophenyl)(methoxy)methyl)thiazol-2-amine (100 mg, 0.39 mmol), triethylamine (0.18 mL, 1.28 mmol) and DMAP (10 mg, 0.08 mmol) were then added at 20° C. and stirring was continued at 60° C. for 12 h. The reaction mixture was concentrated in vacuo. Purification by preparative HPLC (column: Phenomenex Luna 10 μm C18 150×25 mm; acetonitrile:[water (0.1% formic acid)]; gradient: 4:6→7:3) afforded oxazol-2-ylmethyl (5-((4-chlorophenyl)(methoxy)methyl)thiazol-2-yl)carbamate (19 mg, 13%) as a white solid; $\delta_H$ (400 MHz; DMSO-d6) 12.28-11.75 (1H, m), 8.15 (1H, d, J 0.6 Hz), 7.46-7.42 (2H, m), 7.41-7.37 (2H, m), 7.26 (2H, d, J 5.9 Hz), 5.60 (1H, s), 5.28 (2H, s), 3.27 (3H, s); ES-MS $[M+H]^+$: 380.1.

Example 163: Sodium (R)-((5-(1-(4-chlorophenyl)ethyl)thiazol-2-yl)((oxazol-2-ylmethoxy)carbonyl)amino)methyl phosphate Step 1

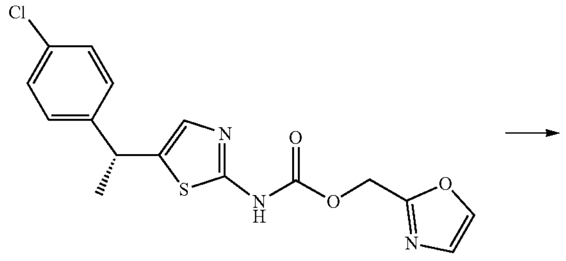

-continued

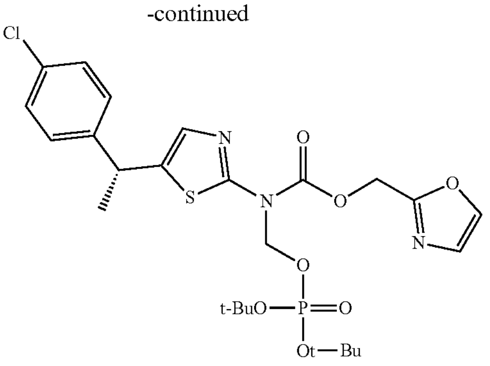

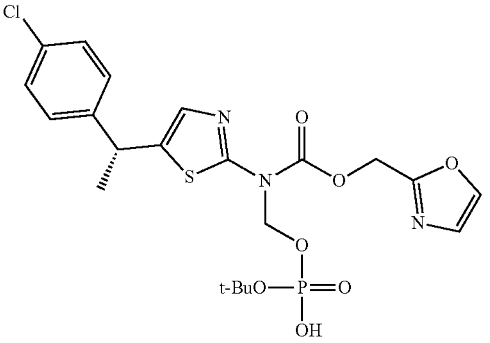

Di-tert-butyl chloromethyl phosphate (500 mg, 1.93 mmol) was added to a mixture of Example 20 (350 mg, 0.83 mmol), potassium iodide (50 mg, 0.30 mmol) and potassium carbonate (400 mg, 2.89 mmol) in DMF (10 mL). The resulting mixture was stirred at 60° C. for 4 h. Water (20 mL) was added and the mixture was extracted into EtOAc (3×20 mL). The combined organic extracts were dried over anhydrous sodium sulfate and then concentrated in vacuo. Purification by lash column chromatography on silica (EtOAc: PE, 0:1 to 1:3) afforded a mixture of oxazol-2-ylmethyl (R)-(5-(1-(4-chlorophenyl)ethyl)thiazol-2-yl)(((di-tert-butoxyphosphoryl)oxy)methyl)carbamate (150 mg, 19%); ES-MS $[M+H]^+$: 586.2; and oxazol-2-ylmethyl (((tert-butoxy(hydroxy)phosphoryl)oxy)methyl)(5-((R)-1-(4-chlorophenyl)ethyl)thiazol-2-yl)carbamate (180 mg, 25%); ES-MS $[M+H]^+$: 530.2.

Step 2

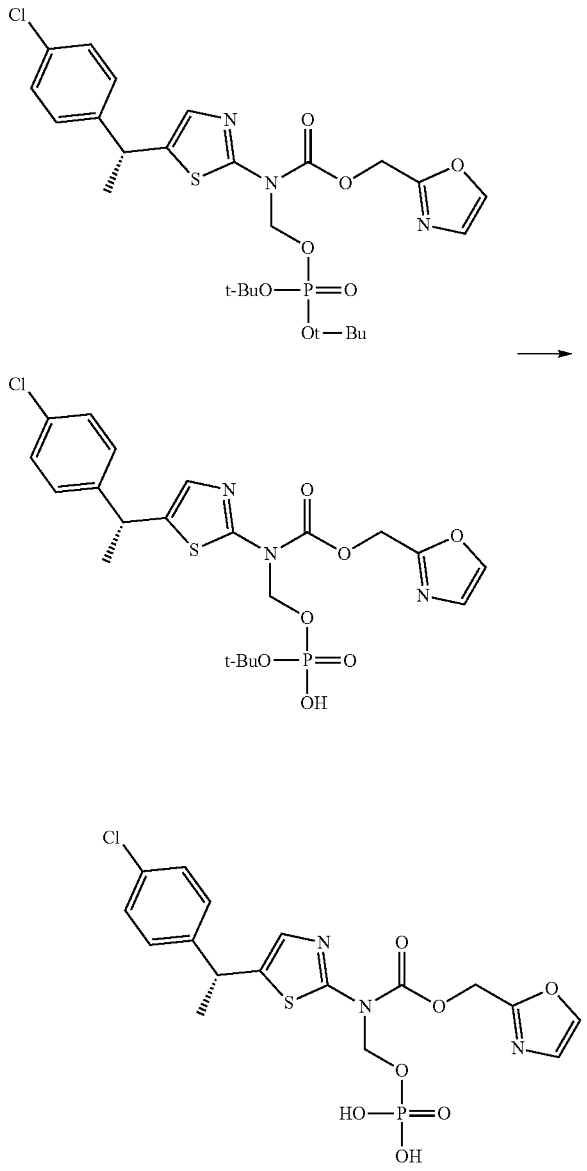

Hydrochloric acid (2.0 M in dioxane, 8 mL, 16 mmol) was added to the two products from Step 1 and the resulting mixture was stirred at 20° C. for 2 h, then concentrated in vacuo. Purification by preparative HPLC (column: Waters™ XBridge, 25 mm×150 mm, 10 μM; acetonitrile:[water (0.1% ammonium bicarbonate)]; gradient: 1:4→2:3) afforded oxazol-2-ylmethyl (R)-(5-(1-(4-chlorophenyl)ethyl)thiazol-2-yl)((phosphonooxy)methyl)carbamate (40 mg, 14%) as a white solid; $\delta_H$ (400 MHz; $CD_3OD$) 7.94 (1H, d, J 0.8 Hz), 7.33-7.25 (4H, m), 7.20 (2H, d, J 0.9 Hz), 5.88 (2H, d, J 7.6 Hz), 5.42 (2H, s), 4.32 (1H, m), 1.66 (3H, d, J 7.1 Hz).

Step 3

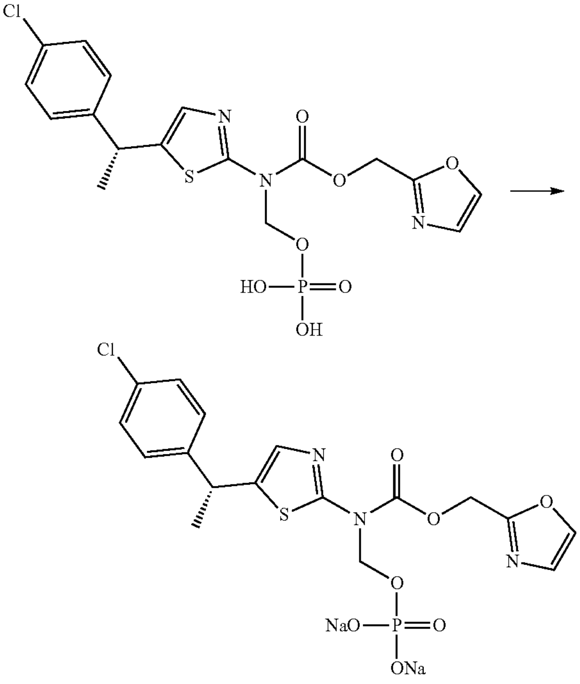

A solution of oxazol-2-ylmethyl (R)-(5-(1-(4-chlorophenyl)ethyl)thiazol-2-yl)((phosphonooxy)methyl)carbamate (40 mg, 0.044 mmol) in water (10 mL) was filtered through Dowex 50W×8 Ion Exchange Resin (sodium form, 100-200 mesh, strongly acidic, 500 mg). The filtrate was lyophilized to afford sodium (R)-((5-(1-(4-chlorophenyl)ethyl)thiazol-2-yl)((oxazol-2-ylmethoxy)carbonyl)amino)methyl phosphate (14 mg, 31%) as a white solid; $\delta_H$ (400 MHz; $D_2O$) 7.90 (1H, s), 7.41-7.37 (2H, m), 7.33 (3H, d, J 8.6 Hz), 7.22 (1H, s), 5.77 (2H, br d, J 8.3 Hz), 5.45 (2H, s), 4.43-4.36 (1H, m), 1.67 (3H, d, J 7.1 Hz); ES-MS $[M+H]^+$: 474.1.

Example 164: Oxazol-2-ylmethyl (5-(4-chlorobenzyl)-4-methylthiazol-2-yl)carbamate Step 1

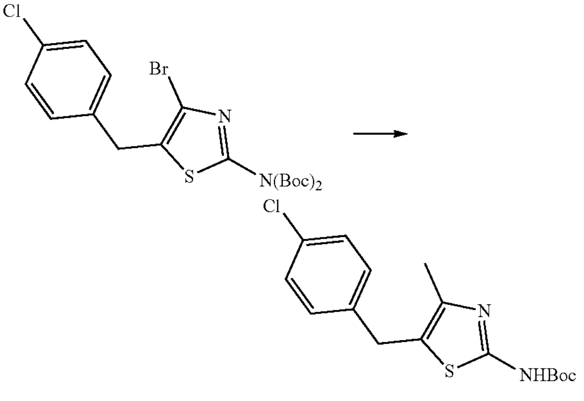

2,4,6-Trimethyl-1,3,5,2,4,6-trioxatriborinane (720 mg, 2.87 mmol) was added to a mixture of di-tert-butyl (4-bromo-5-(4-chlorobenzyl)thiazol-2-yl)iminodicarbonate (see Example 161, 200 mg, 0.40 mmol), Pd(dppf)$C_{12}$ (40 mg, 0.05 mmol), sodium carbonate (120 mg, 1.13 mmol) and water (0.3 mL) in dioxane (1.5 mL). The reaction mixture was stirred at 80° C. for 12 h, then concentrated in vacuo and purified by flash column chromatography on silica (EtOAc:PE, 0:1 to 1:4) to afford tert-butyl (5-(4-chlorobenzyl)-4-methylthiazol-2-yl)carbamate (130 mg, 97%) as a yellow oil; ES-MS $[M+H]^+$: 339.1.

Step 2

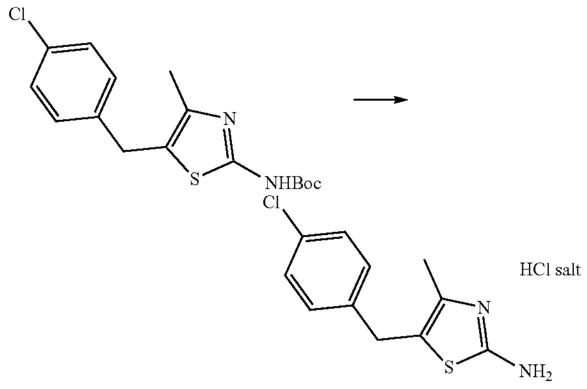

Hydrochloric acid (2.0 M, 2 mL, 4.00 mmol) was added to tert-butyl (5-(4-chlorobenzyl)-4-methylthiazol-2-yl)carbamate (130 mg, 0.38 mmol) and the resulting mixture was stirred at 60° C. for 12 h, then concentrated in vacuo to afford 5-(4-chlorobenzyl)-4-methylthiazol-2-amine HCl salt (80 mg, crude) as a yellow oil; ES-MS $[M+H]^+$: 239.1.

Step 3

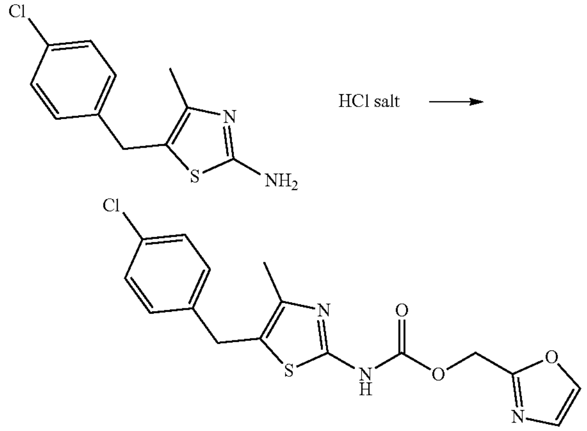

CDI (340 mg, 2.10 mmol) was added to a solution of 5-(4-chlorobenzyl)-4-methylthiazol-2-amine HCl salt (100 mg, 0.42 mmol) in THF (2 mL) at 0° C. and the resulting mixture was stirred at 60° C. for 1 h. Oxazol-2-ylmethanol (210 mg, 2.12 mmol), triethylamine (0.29 mL, 2.08 mmol) and DMAP (10 mg, 0.08 mmol) were then added at 20° C. and stirring was continued at 60° C. for 12 h. The reaction mixture was diluted with water (50 mL) and extracted into EtOAc (3×50 mL). The combined organic extracts were washed with brine (3×50 mL), dried over anhydrous sodium sulfate and concentrated in vacuo. Purification by preparative HPLC (column: Phenomenex Luna 10 μm C18 150×25 mm; acetonitrile:[water (0.1% formic acid)]; gradient: 45:55→65:35) afforded oxazol-2-ylmethyl (5-(4-chlorobenzyl)-4-methylthiazol-2-yl)carbamate (10 mg, 7%) as an off-white gum; $\delta_H$ (400 MHz; DMSO-d6) 12.00-11.51 (1H, m), 8.15 (1H, s), 7.36 (2H, d, J 8.4 Hz), 7.25 (1H, s), 7.23 (2H, d, J 8.4 Hz), 5.26 (2H, s), 3.99 (2H, s), 2.19 (3H, s); ES-MS $[M+H]^+$: 364.1.

Biological Assays

DLD-1 Cell Viability Assay

Compound cytotoxicity in DLD-1 human colorectal adenocarcinoma cells (ATCC CCL-221) was gauged using the CellTiter Glo 2.0 Luminescent Cell Viability Assay (Promega). DLD-1 cells maintained in growth medium (RPMI, 10% FBS, 1% P/S) were seeded into 1536-well black clear bottom plates (Corning 3836) at a density of 400 cells/5 μL/well ($0.08\times10^{6}$ cells/mL) and incubated overnight in a 5% $CO_2$ incubator at 37° C. Compounds in 10 point 1:3 serial dilution in DMSO (provided by compound management in 384-well Low Dead Volume Echo certified plates, Labcyte LP-0200) were stamped (15 nL) onto 1536-well plates containing DLD-1 cells (at about 30-40% cell density) for a final compound concentration ranging from 30 μM to 1.5 nM. 30 μM (final concentration) of Toxoflavin served as a low control while DMSO only served as a high control in these experiments. The final DMSO concentration in the assay plate is 0.3%. Each sample was tested in triplicate.

72 hours post compound introduction, 5 μL of CellTiter Glo 2.0 at room temperature is added to the cells in media using a multidrop combi and incubated for 30 minutes at room temperature. Luminescence from the samples is recorded with a Clariostar Plus plate reader and all data is normalized to the average of DMSO treated group and expressed as the percentage of control. $IC_{50}$ values based on curve classification for each compound were calculated from the concentration response curves (percentage inhibition) using Dotmatics data management software.

Immunofluorescence Nuclear Condensate Assay

An immunofluorescence (IF) assay was used to measure the sequestration of beta catenin into nuclear condensates. DLD-1 cells (ATCC CCL-221) were maintained in growth medium RPMI 1640 (ATCC modification) (Thermo, A1049101) supplemented with 10% fetal bovine serum (VWR, 89510-196). Twenty-four hours prior to compound treatment, cells were seeded into 1536-well black clear bottom plates (Greiner, GR 789866) at a density of 600 cells/5 μL/well and incubated overnight in a 5% $CO_2$ incubator at 37° C. for 24 hours. Compounds in 10 point 1:3 serial dilution in DMSO in 384-well Low Dead Volume Echo certified plates (Labcyte, LP-0200) were stamped (15 nL) onto 1536-well plates containing DLD-1 cells for a final compound concentration ranging from 30 μM to 1.5 nM. NCB-0846 (30 μM) (Selleck, S8392) served as a high control while DMSO served as a low control in these experiments. The final DMSO concentration in the assay plate is 0.3%. Each sample was tested in triplicate.

Twenty-four hours after compound treatment, cells were fixed with the addition of 2 μL of 12% formaldehyde (Sigma, 1.04003) at room temperature for 15 minutes, permeabilized in 0.1% Triton X-100 (Sigma, 93443) in PBS for 15 minutes, blocked in 0.2% gelatin from cold water fish (Sigma, G7765) in PBS for 1 hour, and then stained with a 1:1000 dilution of the phospho beta catenin antibody (Invitrogen, 703638) in 0.2% gelatin overnight at 4° C. followed by incubation with a 1:10000 dilution of Hoechst (Thermo, 1-13570) and with a 1:1000 dilution of secondary antibody (Thermo, A11070) for 1 hour at room temperature. Plates were then imaged (Opera Phenix, Perkin Elmer), and analyzed with the Harmony software quantitating the fraction of cells with bright phospho beta catenin depots (see FIG. 1). The data was normalized to the high (NCB-0846, 30 μM) and low (DMSO) controls. $EC_{50}$ values based on curve classification for each compound were calculated from the concentration response curves (percentage response) using Dotmatics data management software.

The data from the viability $IC_{50}$ and immunofluorescence (IF) $EC_{50}$ values are shown in the table below:

| Ex. No. | DLD-1 Cell Viability $IC_{50}$ | DLD-1 IF $EC_{50}$ |
|---|---|---|
| 1 | A | A |
| 2 | C | C |
| 3 | A | A |
| 4 | C | C |
| 5 | A | A |
| 6 | B | C |
| 7 | A | A |
| 8 | A | A |
| 9 | C | C |
| 10 | B | B |
| 11 | B | B |
| 12 | A | B |
| 13 | A | B |
| 14 | C | B |
| 15 | A | A |
| 16 | B | C |
| 17 | B | A |
| 18 | B | B |
| 19 | B | B |
| 20 | A | A |
| 21 | C | C |
| 22 | A | B |
| 23 | B | B |
| 24 | C | C |
| 25 | A | B |
| 26 | C | C |
| 27 | C | C |
| 28 | C | C |
| 29 | B | C |
| 30 | A | A |
| 31 | A | A |
| 32 | C | C |
| 33 | C | C |
| 34 | B | B |
| 35 | B | B |
| 36 | C | C |
| 37 | B | B |
| 38 | B | C |
| 39 | B | B |
| 40 | B | B |
| 41 | C | C |
| 42 | B | C |
| 43 | A | A |
| 44 | A | A |
| 45 | B | B |
| 46 | B | B |
| 47 | C | C |
| 48 | C | C |
| 49 | B | B |
| 50 | B | B |
| 51 | B | B |
| 52 | B | B |
| 53 | A | A |
| 54 | B | B |
| 55 | C | C |
| 56 | B | C |

-continued

| Ex. No. | DLD-1 Cell Viability $IC_{50}$ | DLD-1 IF $EC_{50}$ |
|---|---|---|
| 57 | C | C |
| 58 | A | B |
| 59 | C | C |
| 60 | C | C |
| 61 | C | C |
| 62 | B | B |
| 63 | B | B |
| 64 | A | A |
| 65 | A | A |
| 66 | C | C |
| 67 | C | C |
| 68 | A | A |
| 69 | C | D |
| 70 | A | A |
| 71 | B | B |
| 72 | C | C |
| 73 | A | A |
| 74 | B | B |
| 75 | C | C |
| 76 | B | B |
| 77 | A | A |
| 78 | B | B |
| 79 | B | B |
| 80 | B | C |
| 81 | A | nd |
| 82 | B | B |
| 83 | B | B |
| 84 | D | D |
| 85 | A | A |
| 86 | A | A |
| 87 | C | C |
| 88 | B | B |
| 89 | C | C |
| 90 | A | A |
| 91 | C | C |
| 92 | B | B |
| 93 | A | A |
| 94 | B | B |
| 95 | B | C |
| 96 | B | B |
| 97 | A | A |
| 98 | A | A |
| 99 | C | C |
| 100 | A | B |
| 101 | B | B |
| 102 | B | B |
| 103 | C | C |
| 104 | B | B |
| 105 | A | A |
| 106 | A | A |
| 107 | A | A |
| 108 | A | A |
| 109 | C | C |
| 110 | B | B |
| 111 | C | C |
| 112 | C | C |
| 113 | C | C |
| 114 | B | B |
| 115 | B | C |
| 116 | A | A |
| 117 | A | A |
| 118 | B | B |
| 119 | A | A |
| 120 | C | C |
| 121 | C | C |
| 122 | C | C |
| 123 | B | B |
| 124 | A | A |
| 125 | C | C |
| 126 | B | B |
| 127 | B | B |
| 128 | B | B |
| 129 | A | A |
| 130 | A | A |
| 131 | C | C |

-continued

| Ex. No. | DLD-1 Cell Viability $IC_{50}$ | DLD-1 IF $EC_{50}$ |
|---|---|---|
| 132 | C | C |
| 133 | C | C |
| 134 | B | B |
| 135 | B | B |
| 136 | C | C |
| 137 | C | D |
| 138 | B | B |
| 139 | B | B |
| 140 | C | C |
| 141 | C | C |
| 142 | B | B |
| 143 | C | D |
| 144 | C | D |
| 145 | B | B |
| 146 | C | C |
| 147 | B | B |
| 148 | A | A |
| 149 | A | B |
| 150 | B | B |
| 151 | B | B |
| 152 | C | C |
| 153 | B | B |
| 154 | B | B |
| 155 | B | B |
| 156 | B | B |
| 157 | C | C |
| 158 | B | B |
| 159 | C | D |
| 160 | C | D |
| 161 | C | D |
| 162 | B | B |
| 163 | A | A |
| 164 | C | C |

A: $IC_{50}$ or $EC_{50}$<0.1 μM
B: $IC_{50}$ or $EC_{50}$≥0.1 and <1 μM
C: $IC_{50}$ or $EC_{50}$≥1 and <10 μM
D: $IC_{50}$ or $EC_{50}$≥10 μM
nd: not determined Mouse Pharmacokinetic Study Example 1 was formulated in DMSO:PEG400:water (1:4:5) for IV dosing and Cremophor® RH 40:20% HP-β-CD (1:19) for PO dosing. Three female BALB/c mice were dosed IV (1 mg/kg) and serial bleed time-points were taken at 0 min, 5 min, 15 min, 30 min, 1 h, 2 h, 4 h, 8 h and 24 h. Ten female BALB/c mice were dosed PO (10 mg/kg) and bleeds were taken at 0 min, 30 min, 1 h, 2 h, 4 h, 8 h and 24 h across the group (maximum two samples per mouse). Samples were prepared by protein precipitation with acetonitrile and analyzed by quantitative LC/MS using a AB API 5500 LC/MS/MS. PK parameters were estimated by non-compartmental model using WinNonlin 8.3. The PK data for Example 1 is shown in the table below:

| Route of administration | Dose | Parameter | Value |
|---|---|---|---|
| PO | 10 mg/kg | $T_{1/2}$ | 2.96 h |
| | | Cmax | 4.45 μM |
| | | $AUC_{last}$ | 12.3 h * μM |
| | | F % | >99% |
| IV | 1 mg/kg | Cl | 32.4 mL/min/kg |
| | | $V_{ss}$ | 1.34 L/kg |

Colorectal Cancer Cell-Line Derived Xenograft Study

Figure 2:
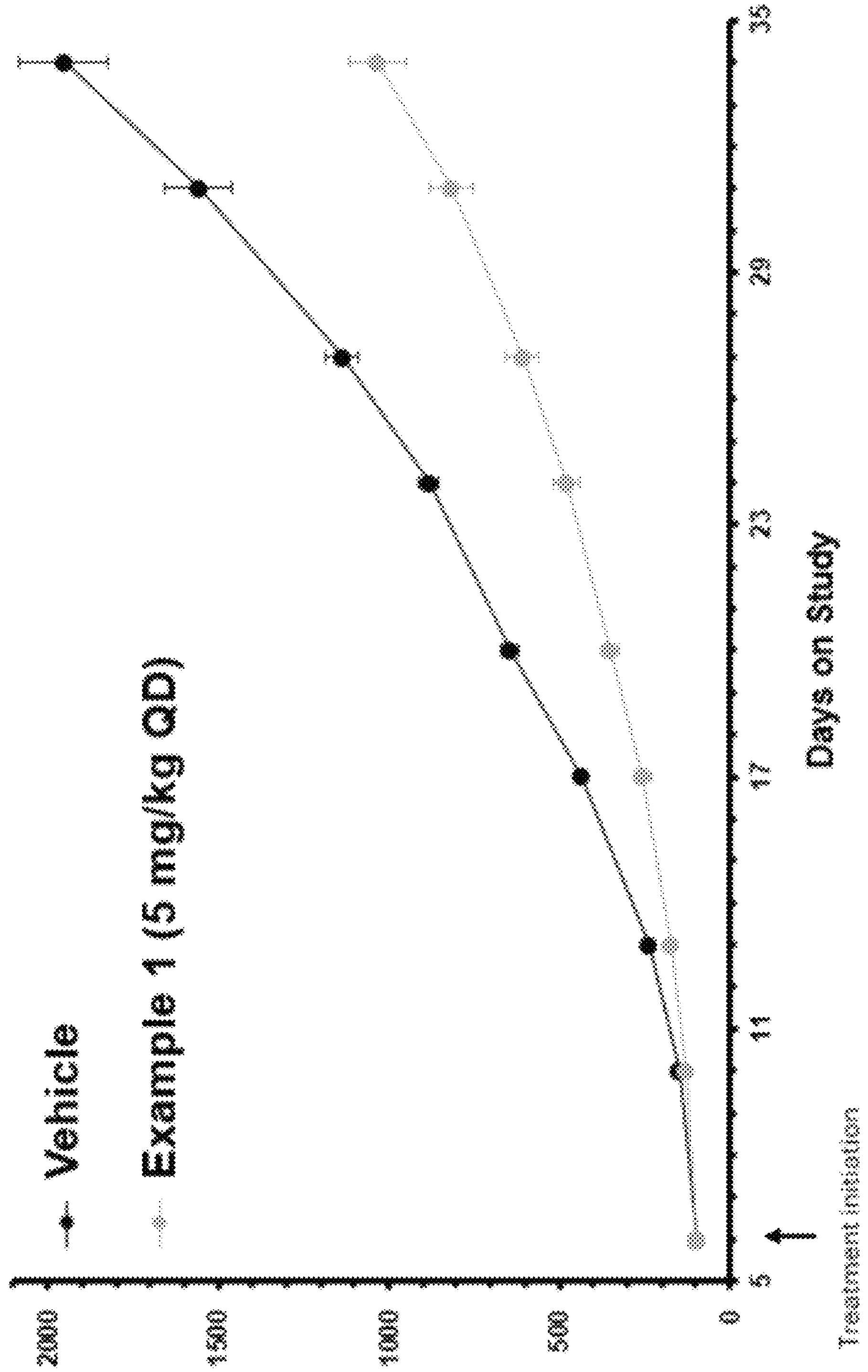
FIG. 2 shows tumor volumes for mice treated with Example 1 and mice provided vehicle.

HCT-116 cells (ATCC CCL-247) were cultured in McCoy's % A media until sufficient cell numbers for implantation into mice were obtained. Cells were harvested and inoculated ($5\times10^6$ in 100 μL in McCoy's 5a medium) subcutaneously into the right flank of nude mice and tumor growth was monitored by caliper measurement. When tumors reached ~70-100 $mm^3$, mice were randomized into treatment groups (5 groups, n=10/group) and treatment was initiated. Example 1, formulated in Cremophor® RH 40:20% HP-β-CD (1:19) for PO dosing, was administered as follows: Vehicle; Example 1-50 mg/kg QD. Tumor volume measurements were captured twice weekly using digital calipers and the data is represented as the mean group tumor volume+/−S.E.M. FIG. 2 shows the tumor volumes for mice treated with Example 1 and mice provided with vehicle.

qPCR Assay

Figure 3:
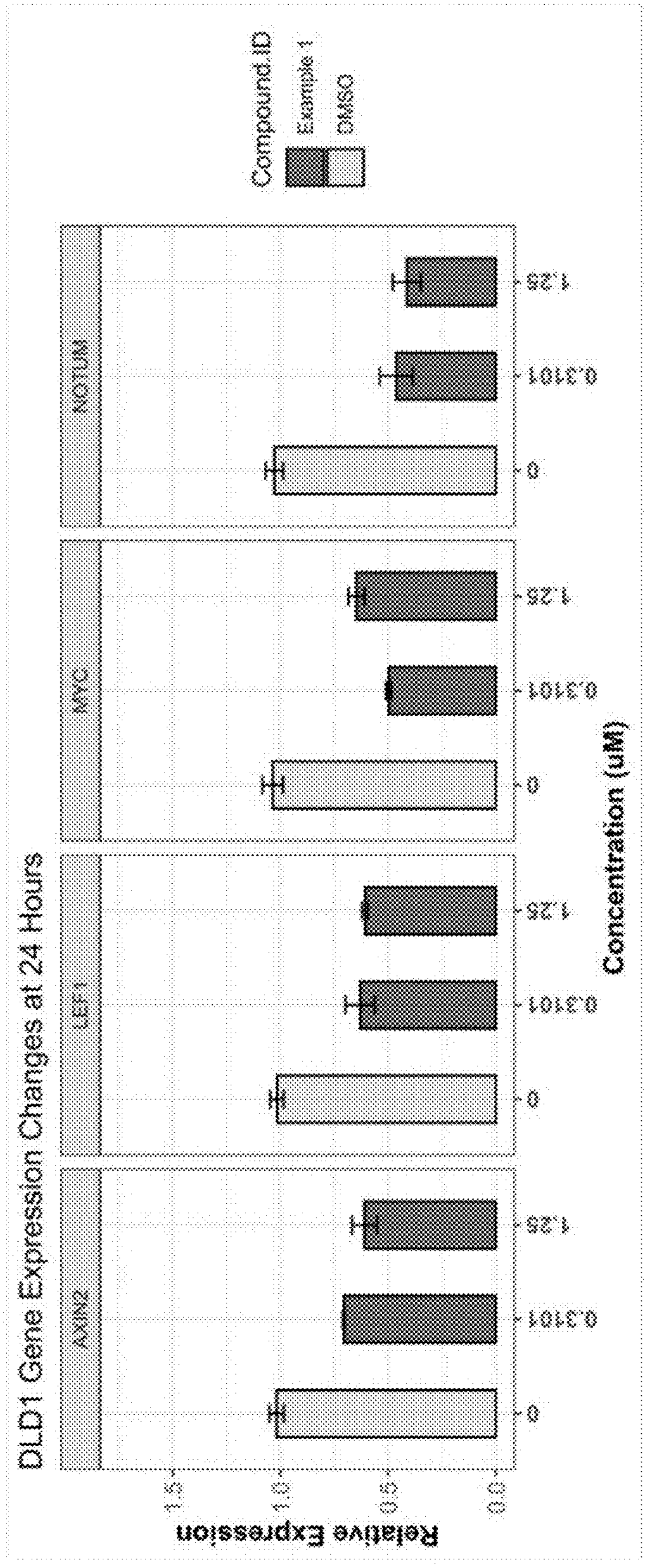
FIG. 3 shows the gene expression changes in DLD-1 cells treated with Example 1 or DMSO.

Gene expression of beta catenin target genes was measured by duplexed Real-Time quantitative Polymerase Chain Reaction (RT-qPCR) in DLD-1 human colorectal adenocarcinoma cells (ATCC CCL-221). DLD-1 cells maintained in growth medium (RPMI ATCC formulation, 10% FBS) were seeded in 384-well black clear bottom plates (Revvity, Phenoplate) at a density of 2000 cells/40 μL/well ($5.0\times10^4$ cells/mL) and incubated overnight at 37° C. with 5% $CO_2$. The example compound diluted in DMSO at the indicated concentrations was added to the cells. The final DMSO concentration in each well was 0.1%. 24 hours after compound addition, cells were washed once with 1× Phosphate Buffered Saline (PBS) and lysed using 30 μL of cell lysis buffer (ThermoFisher #4391851C). Cell lysis occurs over an 8-minute period at room temperature while shaking the plate on a platform shaker. After cell lysis, 3 μL of stop solution (ThermoFisher #4391851C) was added. 4 μL of cell lysate was then transferred to 384-well qPCR-compatible plates (ThermoFisher #4483285). qPCR Master Mix (ThermoFisher #A15299) containing target and housekeeping TaqMan probes is then dispensed, and each reaction was assembled according to the manufacturer's instructions. Transcript abundance was measured by qPCR using a Quantstudio 7 Flex thermocycler. Each sample was tested in duplicate across 4 beta catenin target genes: Axin2 (ThermoFisher Hs00610344_m1), Lef1 (ThermoFisher Hs01547250_m1), Myc (ThermoFisher Hs00153408_m1), and Notum (ThermoFisher Hs00394510_m1). The housekeeping control gene, RNase P, was duplexed with one target gene per well. Quantification was performed by calculating the ΔΔCt and relative quantification ($2^{-\Delta\Delta Ct}$) values. FIG. 3 shows the gene expression changes in DLD-1 cells treated with Example 1 or DMSO.

What is claimed is:

1. A compound, wherein the compound is:

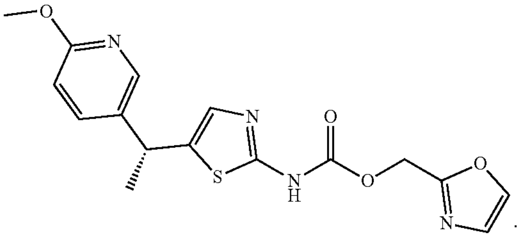 [SMILES: COc1ccc([C@@H](C)c2cnc(NC(=O)OCc3ncco3)s2)cn1]

2. A pharmaceutical composition comprising a compound according to claim 1 and a pharmaceutically acceptable carrier.

3. A compound, wherein the compound is:
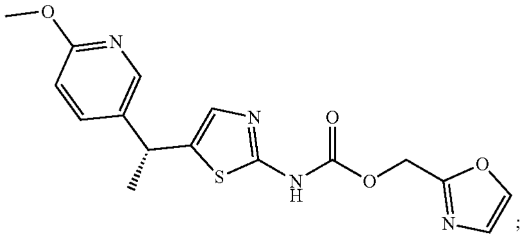 [SMILES: COc1ccc([C@@H](C)c2cnc(NC(=O)OCc3ncco3)s2)cn1]
;
or a pharmaceutically acceptable salt thereof.
4. A pharmaceutical composition comprising a compound according to claim 3, or a pharmaceutically acceptable salt thereof, and a pharmaceutically acceptable carrier.
* * * * *